US009045467B2

(12) United States Patent
Chobanian et al.

(10) Patent No.: US 9,045,467 B2
(45) Date of Patent: Jun. 2, 2015

(54) OXAZOLE DERIVATIVES USEFUL AS INHIBITORS OF FAAH

(71) Applicant: Merck Sharp & Dohme Corp., Rahway, NJ (US)

(72) Inventors: Harry Chobanian, Aberdeen, NJ (US); Linus S. Lin, Westfield, NJ (US); Ping Liu, Westfield, NJ (US); Marc D. Chioda, Metuchen, NJ (US); Robert J. DeVita, Westfield, NJ (US); Ravi P. Nargund, Westfield, NJ (US); Yan Guo, Westfield, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/099,142

(22) Filed: Dec. 6, 2013

(65) Prior Publication Data
US 2014/0171437 A1    Jun. 19, 2014

Related U.S. Application Data

(62) Division of application No. 13/057,415, filed as application No. PCT/US2009/052171 on Jul. 30, 2009, now Pat. No. 8,673,941.

(60) Provisional application No. 61/137,892, filed on Aug. 4, 2008.

(51) Int. Cl.
| A01N 43/40 | (2006.01) |
| A61K 31/44 | (2006.01) |
| C07D 413/14 | (2006.01) |
| C07D 263/46 | (2006.01) |
| C07D 413/04 | (2006.01) |
| C07D 413/10 | (2006.01) |
| C07D 417/04 | (2006.01) |
| C07D 417/14 | (2006.01) |
| C07D 271/06 | (2006.01) |
| C07D 271/10 | (2006.01) |

(52) U.S. Cl.
CPC ............ *C07D 413/14* (2013.01); *C07D 263/46* (2013.01); *C07D 413/04* (2013.01); *C07D 413/10* (2013.01); *C07D 417/04* (2013.01); *C07D 417/14* (2013.01); *C07D 271/06* (2013.01); *C07D 271/10* (2013.01)

(58) Field of Classification Search
USPC ........ 514/340; 544/238, 405, 333; 546/271.4, 546/256; 548/225
See application file for complete search history.

(56) References Cited

U.S. PATENT DOCUMENTS

| 8,673,941 B2 * | 3/2014 | Chobanian et al. ............ 514/340 |
| 2011/0021531 A1 * | 1/2011 | Chobanian et al. ...... 514/252.03 |
| 2013/0018048 A1 * | 1/2013 | Yang et al. ................. 514/227.8 |
| 2013/0030000 A1 * | 1/2013 | Chobanian et al. ...... 514/252.03 |

FOREIGN PATENT DOCUMENTS

| WO | WO97/03688 | 2/1997 |
| WO | WO 9703688 A1 * | 2/1997 |
| WO | WO2004/033652 | 4/2004 |
| WO | WO2011/094209 | 8/2011 |
| WO | WO 2011094209 A1 * | 8/2011 |
| WO | WO2011/126960 | 10/2011 |
| WO | WO 2011126960 A1 * | 10/2011 |

OTHER PUBLICATIONS

J.E. Schlosburg et al., II The AAPS Journal, 39-44 (2009).*
D. Richardson, 10 Arthritis Research & Therapy 1-14 (2008).*
Pil'O, S.G. et al., Synthesis of New 5-Mercapto-1,3-oxazole Derivatives on the Basis of 2-Acylamino-3,3-Dichloroacrylonitriles and Their Analogs, Russian Journal of General Chemistry, Pleiades Publishing Ltd. 2002, pp. 1714-1723, vol. 72, No. 11.
Kreisberg, J.D. et al., "Pummerer Reaction Methodology for the Synthesis of 5-Thiophenyl Substituted Oxazoles", Tetrahedron Letters, 2002, pp. 7393-7396, No. 43.
Du, W. et al., "Heterocyclic Sulfonxide and Sulfone Inhibitors of Fatty Acid Amide Hydrolase", Bioorganic & Medicinal Chemistry Letters, 2005, pp. 103-106, No. 15.
Liu, X.H. et al., "Novel 2,4,5-Trisubstituted Oxazole Derivatives: Synthesis and Antiproliferative Activity", European Journal of Medicinal Chemistry, 2009, pp. 3930-3935, No. 44.
International Preliminary Report on Patentability, PCT/US09/52171 (Feb. 8, 2011).

* cited by examiner

*Primary Examiner* — Alexander R Pagano
(74) *Attorney, Agent, or Firm* — Matthew A. Leff; John C. Todaro

(57) ABSTRACT

The present invention is directed to certain oxazole derivatives which are useful as inhibitors of Fatty Acid Amide Hydrolase (FAAH). The invention is also concerned with pharmaceutical formulations comprising these compounds as active ingredients and the use of the compounds and their formulations in the treatment of certain disorders, including osteoarthritis, rheumatoid arthritis, diabetic neuropathy, postherpetic neuralgia, skeletomuscular pain, and fibromyalgia, as well as acute pain, migraine, sleep disorder, Alzheimer Disease, and Parkinson's Disease.

19 Claims, No Drawings

OXAZOLE DERIVATIVES USEFUL AS INHIBITORS OF FAAH

CROSS REFERENCE TO RELATED APPLICATIONS

This application is a divisional application of U.S. Ser. No. 13/057,415, Feb. 3, 2011, which is a U.S. National Phase application under 35 U.S.C. §371 of PCT Application No. PCT/US2009/052171, filed Jul. 30, 2009, which claims priority under 35 U.S.C. §119(e) from U.S. Provisional Application Ser. No. 61/137,892, filed Aug. 4, 2008.

REFERENCE TO A SEQUENCE LISTING SUBMITTED AS A TEXT FILE VIA EFS-WEB

The Sequence Listing is submitted as a text file via EFS-Web with a file name of MRLBRE00006USDIV_SeqList_25Feb2014.txt, a creation date of Feb. 25, 2014, and a size of 1.0 kilobyte. The Sequence Listing filed via EFS-Web is part of the specification and is hereby incorporated in its entirety by reference herein.

BACKGROUND OF THE INVENTION

Disclosed herein are compounds that inhibit the activity of fatty acid amide hydrolase (FAAH), compositions that include the compounds, and methods of their use. Compounds disclosed herein as inhibitors of fatty acid amide hydrolase (FAAH) are useful in the treatment of diseases, disorders, or conditions that would benefit from the inhibition of fatty acid amide hydrolase and increases in endogenous fatty acid amides.

Fatty acid amide hydrolase (FAAH) is an enzyme that is abundantly expressed throughout the CNS (Freund et al. Physiol. Rev. 2003; 83:1017-1066) as well as in peripheral tissues, such as, for example, in the pancreas, brain, kidney, skeletal muscle, placenta, and liver (Giang, D. K. et al., Proc. Natl. Acad. Sci. U.S.A. 1997, 94, 2238-2242; Cravatt et al. Proc. Natl. Acad. Sci. U.S.A. 2004, 101, 29, 10821-10826). FAAH hydrolyzes the fatty acid amide (FAA) family of endogenous signaling lipids. General classes of fatty acid amides include the N-acylethanolamides (NAEs) and fatty acid primary amides (FAPAs). Examples of NAEs include anandamide (AEA), palmitoylethanolamide (PEA) and oleoylethanolamide (OEA). An example of FAPAs includes 9-Z-octadecenamide or oleamide. (McKinney M K. and Cravatt B F. 2005. Annu Rev Biochem 74:411-32). Another class of fatty acid amide family of endogenous signaling lipids is N-acyl taurines that have also been shown to be elevated upon FAAH deletion or inhibition and appear to act on transient receptor potential (TRP) family of calcium channels, although the functional consequences are not yet clear (Saghatelian A, et al. Biochemistry. 2004, 43:14332-9, Saghatelian A, et al. Biochemistry, 2006, 45:9007-9015). In addition to fatty acid amides, FAAH can also hydrolyze certain fatty acid esters, such as, for example, 2-arachidonylglycerol (2-AG) another endocannabinoid (Mechoulam et al. Biochem. Pharmacol. 1995; 50:83-90; Stella et al. Nature, 1997; 388:773-778; Suguria et al. Biochem. Biophys. Res. Commun. 1995; 215:89-97).

Inhibition of FAAH is expected to lead to an increase in the level of anandamide and other fatty acid amides. This increase in fatty acid amides leads to an increase in the noiceptive threshold. Thus, inhibitors of FAAH are useful in the treatment of pain (Cravatt, B F; Lichtman, A H Current Opinion in Chemical Biology 2003, 7, 469-475). Such inhibitors are useful in the treatment of other disorders that can be treated using fatty acid amides or modulators of cannabinoid receptors, such as, for example, anxiety, sleep disorder, Alzheimer disease, and Parkinson's disease, eating disorders, metabolic disorders, cardiovascular disorders, and inflammation (Simon et al Archives of Gen. Psychiatry, 2006, 63, 824-830. Kunos, G et al. *Pharmacol Rev* 2006, 58, 389-462). In some embodiments, FAAH inhibitor compounds may be peripherally restricted and may not substantially affect neural disorders, such as, for example, depression and anxiety. Finally, agonism of cannabinoid receptors has also been shown to reduce the progression of atherosclerosis in animal models (see Steffens et al. Nature, 2005, 434, 782-786; and Steffens et al., Curr Opin. Lipid., 2006, 17, 519-526). Thus, increasing the level of endogenous cannabinergic fatty acid amides (e.g., anandamide) is expected to effectively treat or reduce the risk of developing atherosclerosis.

Inhibition of FAAH also leads to elevation of palmitoylethanolamide which is thought to work, in part, through activation of the peroxisome proliferator-activated receptor α (PPAR-α) to regulate multiple pathways including, for example, pain perception in neuropathic and inflammatory conditions such as convulsions, neurotoxicity, spacticity and to reduce inflammation, for example, in atopic eczema and arthritis (LoVerme J et al. The nuclear receptor peroxisome proliferator-activated receptor-alpha mediates the anti-inflammatory actions of palmitoylethanolamide. *Mol Pharmacol* 2005, 67, 15-19; LoVerme J et al. The search for the palmitoylethanolamide receptor. *Life Sci* 2005, 77: 1685-1698. Lambert D M et al. The palmitoylethanolamide family: a new class of anti-inflammatory agents? *Curr Med Chem* 2002, 9: 663-674; Eberlein B, et al. Adjuvant treatment of atopic eczema: assessment of an emollient containing N-palmitoylethanolamine (ATOPA study). J Eur Acad Dermatol Venereol. 2008, 22:73-82. Re G, et al. Palmitoylethanolamide, endocannabinoids and related cannabimimetic compounds in protection against tissue inflammation and pain: potential use in companion animals. Vet J. 2007 173: 21-30). Thus, inhibition of FAAH is useful for the treatment of various pain and inflammatory conditions, such as osteoarthritis, rheumatoid arthritis, diabetic neuropathy, postherpetic neuralgia, skeletomuscular pain, and fibromyalgia.

It is also thought that certain fatty acid amides, such as, for example, OEA, act through the peroxisome proliferator-activated receptor α (PPAR-α) to regulate diverse physiological processes, including, e.g., feeding and lipolysis. Consistent with this, human adipose tissue has been shown to bind and metabolize endocannabinoids such as anandamide and 2-arachidonylglycerol (see Spoto et al., Biochimie 2006, 88, 1889-1897; and Matias et al., J. Clin. Endocrin. & Met., 2006, 91, 3171-3180). Thus, inhibiting FAAH activity in vivo leads to reduced body fat, body weight, caloric intake, and liver triglyceride levels. However, unlike other anti-lipidemic agents that act through. PPAR-α, e.g., fibrates, FAAH inhibitors do not cause adverse side effects such as rash, fatigue, headache, erectile dysfunction, and, more rarely, anemia, leukopenia, angioedema, and hepatitis (see, e.g., Muscari et al. Cardiology, 2002, 97: 115-121).

Many fatty acid amides are produced on demand and rapidly degraded by FAAH. As a result, hydrolysis by FAAH is considered to be one of the essential steps in the regulation of fatty acid amide levels in the central nervous system as well as in peripheral tissues and fluids. The broad distribution of FAAH combined with the broad array of biological effects of fatty acid amides (both endocannabinoid and non-endocannabinoid mechanisms) suggests that inhibition of FAAH leads to altered levels of fatty acid amides in many tissues and fluids and may be useful to treat many different conditions. FAAH inhibitors increase the levels of endogenous fatty acid amides. FAAH inhibitors block the degradation of endocannabinoids and increase the tissue levels of these endogenous substances. FAAH inhibitors can be used in this respect in the prevention and treatment of pathologies in which endogenous cannabinoids and or any other substrates metabolized by the FAAH enzyme are involved.

The various fatty acid ethanolamides have important and diverse physiological functions. As a result, inhibitor molecules that selectively inhibit FAAH enzymatic activity would allow a corresponding selective modulation of the cellular and extra-cellular concentrations of a FAAH substrate. FAAH inhibitors that are biologically compatible could be effective pharmaceutical compounds when formulated as therapeutic agents for any clinical indication where FAAH enzymatic inhibition is desired. In some embodiments, FAAH activity in peripheral tissues can be preferentially inhibited. In some embodiments, FAAH inhibitors that do substantially cross the blood-brain-barrier can be used to preferentially inhibit FAAH activity in peripheral tissues. In some embodiments, FAAH inhibitors that preferentially inhibit FAAH activity in peripheral tissues can minimize the effects of FAAH inhibition in the central nervous system. In some embodiments, it is preferred to inhibit FAAH activity in peripheral tissues and minimize FAAH inhibition in the central nervous system.

SUMMARY OF THE INVENTION

The present invention is directed to certain oxazole derivatives which are useful as inhibitors of Fatty Acid Amide Hydrolase (FAAH). The invention is also concerned with pharmaceutical formulations comprising these compounds as active ingredients and the use of the compounds and their formulations in the treatment of certain disorders, including osteoarthritis, rheumatoid arthritis, diabetic neuropathy, postherpetic neuralgia, skeletomuscular pain, and fibromyalgia, as well as acute pain, migraine, sleep disorder, Alzheimer disease, and Parkinson's disease.

DETAILED DESCRIPTION OF THE INVENTION

In one aspect the invention is directed to compounds of formula I:

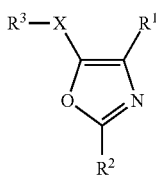

I or a pharmaceutically acceptable salt thereof wherein:
X is S or SO;
n is 0, 1 or 2;
$R^1$ is selected from the group consisting of:
(1) aryl, and
(2) $HET^1$,
wherein $R^1$ is optionally mono or di-substituted with substituents $R^4$ and $R^5$; and wherein $R^4$ and $R^5$ are independently selected from the group consisting of:
(a) halo,
(h) —CN,
(c) mono, di or tri-halo $C_{1-4}$ alkyl,
(d) mono, di or tri-halo $OC_{1-4}$ alkyl,
(d) —$OC_{1-4}$ alkyl, optionally substituted with hydroxyl, halo or amino,
(e) —$C_{1-4}$alkyl optionally substituted with one or two substituents selected from hydroxyl, CN, —$CHF_2$ and —$CF_3$,
(f) —$C_{1-2}$alkyl-$C_{3-6}$cycloalkyl optionally substituted with hydroxy, halo or CN,
(g) —$S(O)_nC_{1-4}$alkyl,
(h) —$S(O)_nNR^6R^7$,
(i) —C(O)—NH—$NR^8R^9$,
(j) —C(O)—OH,
(k) —C(O)—$OC_{1-4}$alkyl, optionally substituted with halo or hydroxy,
(l) —C(O)—$NR^{10}R^{11}$,
(m) —C(O)—$C_{1-4}$alkyl optionally mono, di or tri substituted with halo,
(o) —$C(NR^{12})$—$NR^{13}R^{14}$,
(p) $HET^4$,
(q) aryl,
(r) —C(O)—NH—NH—C(O)H,
(s) —$CH_2$—C(O)—O—$C_{1-4}$alkyl, whereas the $CH_2$ may be optionally substituted with $C_{1-4}$alkyl or OH
(t) —$CH_2$—$C(O)NR^{15}R^{16}$, whereas the $CH_2$ may be optionally substituted with $C_{1-4}$alkyl or OH, and
(u) —$NR^{17}R^{18}$,
wherein choices (p) and (q) are each optionally mono or di-substituted with substituents selected from
(1) halo,
(2) —CN,
(3) —OH,
(4) —$C_{1-4}$alkyl optionally substituted with hydroxy, halo or cyano,
(5) —$CF_3$,
(6) —$OC_{1-4}$alkyl optionally substituted with hydroxyl or halo,
(7) —C(O)OH, and
(8) —C(O)O—$C_{1-3}$alkyl;
(9) —C(O)—$NR^{19}R^{20}$,
(10) —$NH_2$,
(11) Oxo,
(12) =S,
with the proviso that the substituent on choice (q) is other than oxo or =S,
wherein $R^6, R^7, R^8, R^9, R^{10}, R^{11}, R^{12}, R^{13}, R^{14}, R^{15}, R^{16}, R^{17}, R^{18}, R^{19}$ and $R^{20}$, are each independently selected from H and $C_{1-4}$alkyl,
or
$R^6$ and $R^7$ or $R^8$ and $R^9$ or $R^{10}$ and $R^{11}$ or $R^{13}$ and $R^{14}$ or $R^{15}$ and $R^{16}$ or $R^{17}$ and $R^{18}$ or $R^{19}$ and $R^{20}$ are joined together to form a ring with the atoms to which they are attached there is formed a 5-membered heterocyclic ring of 4 to 7 atoms, said ring containing 1, 2, 3 or 4 heteroatoms selected from N, O and S, said ring being optionally mono or di-substituted with substituents independently selected from halo, hydroxyl, oxo, $C_{1-4}$alkyl, hydroxy$C_{1-4}$alkyl, halo$C_{1-4}$alkyl, —C(O)—$C_{1-4}$alkyl and —$S(O)nC_{1-4}$alkyl;
$R^2$ is selected from the group consisting of:
(1) aryl,
(2) $HET^3$,
(3) —$CH_2$-aryl,
(4) —$CH_2$—$HET^3$,
(5) —$C_{1-6}$alkyl, and
(6) —$C_{3-6}$cycloalkyl,
wherein $R^2$ is optionally mono or di-substituted with substituents independently selected from the group consisting of (a) halo,
(b) —CN,
(c) —OH,
(d) —C$_{1-4}$alkyl optionally substituted with hydroxy, halo or cyano,
(e) —CF$_3$,
(f) —OC$_{1-4}$alkyl optionally substituted with hydroxyl or halo,
(g) —C(O)O—C$_{1-3}$alkyl and
(h) —S-aryl, optionally substituted with halo, C$_{1-4}$alkyl or —OC$_{1-4}$alkyl;

R$^3$ is selected from the group consisting of:
(1) aryl,
(2) HET$^5$, and
(3) C$_{3-6}$cycloalkyl,
wherein R$^3$ is optionally mono or di-substituted with substituents independently selected from the group consisting of
(a) hydroxy,
(b) halo,
(c) —C$_{3-6}$cycloalkyl,
(d) —OC$_{3-5}$cycloalkyl,
(e) —C$_{1-4}$ alkyl,
(f) —OC$_{1-4}$ alkyl,
(g) —C(O)CH$_3$
(h) mono, di or tri-halo C$_{1-4}$ alkyl,
(i) mono, di or tri-halo —OC$_{1-4}$ alkyl, and
(j) —S(O)$_n$—C$_{1-4}$ alkyl;
wherein aryl is as a mono- or bi-cyclic aromatic ring system; and HET$^1$, HET$^2$, HET$^3$, HET$^4$ and HET$^5$ are each independently a 5 to 10-membered aromatic, partially aromatic or non-aromatic mono- or bicyclic ring, or N-oxide thereof, said containing 1 to 4 heteroatoms selected from O, S and N, and optionally substituted with 1 to 2 oxo groups.

Within this aspect there is a genus wherein:
R$^1$ is selected from the group consisting of:
(1) phenyl,
(2) pyridyl,
(3) pyridazinyl,
(4) pyrimidyl,
(5) pyrazinyl,
(6) thiazolyl,
(7) thienyl,
(8) pyrrolyl,
(9) oxazolyl, and
(10) oxadiazole;
wherein R$^1$ is optionally mono or di-substituted with substituents R$^4$ and R$^5$, wherein R$^4$ and R$^5$ are independently selected from the group consisting of:
(a) halo,
(b) —CN,
(c) mono, di or tri-halo C$_{1-4}$ alkyl,
(d) —O—C$_{1-4}$alkyl, optionally substituted with hydroxyl, halo or amino
(e) —C$_{1-4}$alkyl optionally substituted with hydroxyl or CN,
(f) —C$_{1-2}$alkyl-C$_{3-6}$cycloalkyl optionally substituted with hydroxy,
(h) —S(O)$_n$C$_{1-4}$alkyl wherein n is 0, 1 or 2,
(i) —S(O)$_n$NR$^6$R$^7$,
(j) —C(O)—NR$^{10}$R$^{11}$,
(k) HET$^4$,
(l) aryl, and
wherein choices (k) and (l) are each optionally mono or di-substituted with substituents selected from
(1) halo,
(2) —CN,
(3) —OH,
(4) —C$_{1-4}$alkyl optionally substituted with hydroxy, halo or cyano,
(5) —CF$_3$,
(6) —OC$_{1-4}$alkyl optionally substituted with hydroxyl or halo,
(7) —C(O)OH,
(8) —C(O)O—C$_{1-3}$alkyl, and
(9) —C(O)—NR$^{19}$R$^{20}$,
wherein R$^6$, R$^7$, R$^{10}$, R$^{11}$, R$^{19}$ and R$^{20}$ are each independently selected from H and C$_{1-4}$alkyl.

Within this genus there is a sub-genus wherein:
R$^1$ is selected from the group consisting of:
(1) phenyl,
(2) pyridyl,
(3) pyrimidyl,
(4) pyrazinyl,
(5) pyridazinyl,
(6) 1,2,4-oxadiazolyl, and
(7) 1,3,4-oxadiazolyl,
optionally mono or di-substituted with substituents R$^4$ and R$^5$, which are independently selected from the group consisting of
(a) —C$_{1-4}$alkyl optionally substituted with hydroxy,
(b) —S(O)$_n$C$_{1-4}$alkyl,
(c) —C(O)—NR$^{10}$R$^{11}$,
(d) HET$^4$, and
(e) halo,
wherein HET$^4$ is optionally mono or di-substituted with substituents selected from:
(1) halo,
(2) —CN,
(3) —OH,
(4) —C$_{1-4}$alkyl optionally substituted with hydroxy, halo or cyano,
(5) —CF$_3$,
(6) —OC$_{1-4}$alkyl optionally substituted with hydroxyl or halo,
(7) —C(O)OH, and
(8) —C(O)O—C$_{1-3}$alkyl, and
(9) —C(O)—NR$^{19}$R$^{20}$,
wherein R$^{10}$, R$^{11}$, R$^{19}$ and R$^{20}$ are each independently selected from H and C$_{1-4}$alkyl.

Within this aspect there is a genus wherein:
R$^2$ is selected from the group consisting of:
(1) aryl,
(2) HET$^3$,
(3) —CH$_2$aryl, and
(4) —CH$_2$HET$^3$,
wherein R$^2$ is optionally mono or di-substituted with substituents independently selected from the group consisting of:
(a) halo,
(b) —CN,
(c) —OH,
(d) —Hydroxy C$_{1-4}$alkyl,
(e) —C$_{1-4}$alkyl,
(f) —C$_{1-4}$haloalkyl, and
(g) —OC$_{1-4}$alkyl, optionally substituted with halo or hydroxyl.

Within this genus there is a sub-genus wherein:
R$^2$ is selected from the group consisting of:
(1) aryl, and
(2) HET$^3$,
wherein R$^2$ is optionally mono or di-substituted with substituents independently selected from the group consisting of
(a) halo,
(b) —CN,
(c) —OH, (d) -hydroxy $C_{1-4}$alkyl,
(e) —$CH_3$,
(f) —$CF_3$, and
(g) —$OCH_3$.

Within this sub-genus there is a class wherein:
$R^2$ is selected from the group consisting of:
(1) phenyl,
(2) pyridyl,
(3) pyridazinyl,
(4) pyrimidyl,
(5) pyrazinyl,
(6) thiazolyl,
(7) oxazolyl,
(8) pyrazolyl,
(9) 1,2,4-oxadiazolyl, and
(10) 1,3,4-oxadiazolyl,
wherein $R^2$ is optionally mono or di-substituted with halo, $OC_{1-4}$alkyl optimally substituted with halogen, —$C_{1-4}$haloalkyl, hydroxyl and CN.

Within this aspect there is a genus wherein:
$R^3$ is selected from the group consisting of:
(1) aryl, and
(2) $HET^5$,
wherein choice (1) and (2) are each optionally mono or di-substituted with substituents independently selected from the group consisting of:
(a) halo,
(b) —$C_{3-6}$cycloalkyl,
(c) —$OC_{1-4}$ alkyl,
(d) mono, di or tri-halo $C_{1-4}$ alkyl, and
(e) mono, di or tri-halo —$OC_{1-4}$ alkyl.

Within this genus there is a sub-genus wherein:
$R^3$ is selected from the group consisting of:
(1) phenyl,
(2) pyrimidyl,
(3) pyridyl,
wherein $R^3$ is optionally mono or di-substituted with halo, halo$C_{1-4}$alkyl, or —$OC_{1-4}$alkyl optionally substituted with halo.

Within this aspect there is a genus wherein X is S.
Within this aspect there is a genus of the Formula

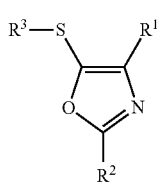

Ia wherein
$R^1$ is selected from the group consisting of:
(1) phenyl,
(2) pyridyl,
(3) pyridazinyl,
(4) pyrimidyl,
(5) pyrazinyl,
(6) thiazolyl,
(7) thienyl,
(8) pyrrolyl,
(9) oxazolyl, and
(10) oxadiazole;
wherein $R^1$ is optionally mono or di-substituted with substituents $R^4$ and $R^5$, which are independently selected from the group consisting of (a) halo,
(b) —CN,
(c) mono, di or tri-halo $C_{1-4}$ alkyl,
(d) —O—$C_{1-4}$alkyl, optionally substituted with hydroxyl, halo or amino
(e) —$C_{1-4}$alkyl optionally substituted with hydroxyl or CN,
(f) —$C_{1-2}$alkyl-$C_{3-6}$cycloalkyl optionally substituted with hydroxy,
(h) —$S(O)_nC_{1-4}$alkyl wherein n is 0, 1 or 2,
(i) —$S(O)_nNR^6R^7$,
(j) —$C(O)$—$NR^{10}R^{11}$,
(k) $HET^4$,
(l) aryl, and
wherein choices (k) and (l) are each optionally mono or di-substituted with substituents selected from
(1) halo,
(2) —CN,
(3) —OH,
(4) —$C_{1-4}$alkyl optionally substituted with hydroxy, halo or cyano,
(5) —$CF_3$,
(6) —$OC_{2-4}$alkyl optionally substituted with hydroxyl or halo,
(7) —C(O)OH,
(8) —C(O)O—$C_{1-3}$alkyl, and
(9) —C(O)—$NR^{19}R^{20}$,
wherein $R^6, R^7, R^{10}, R^{11}, R^{19}$ and $R^{20}$, are each independently selected from H and $C_{1-4}$alkyl; $R^2$ is selected from the group consisting of:
(1) aryl,
(2) $HET^3$,
(3) —$C_{1-6}$alkyl, and
(4) —$C_{3-6}$cycloalkyl,
wherein choice $R^2$ is optionally mono or di-substituted with substituents independently selected from the group consisting of
(a) halo,
(b) —CN,
(c) —OH,
(d) -hydroxy $C_{1-4}$alkyl,
(e) —$C_{1-4}$alkyl,
(f) —$C_{1-4}$haloalkyl, and
(g) —$OC_{1-4}$alkyl, optionally substituted with halo or hydroxyl; and
$R^3$ is selected from the group consisting of:
(1) aryl, and
(2) $HET^5$,
wherein choice (1) and (2) are each optionally mono or di-substituted with substituents independently selected from the group consisting of
(a) halo,
(b) —$C_{3-6}$cycloalkyl,
(c) —$C_{1-4}$ alkyl,
(d) —$OC_{1-4}$ alkyl,
(e) mono, di or tri-halo $C_{1-4}$ alkyl, and
(f) mono, di or tri-halo —$OC_{1-4}$ alkyl.

Within this genus there is a sub-genus wherein:
$R^1$ is selected from the group consisting of:
(1) phenyl,
(2) pyridinyl,
(3) pyrimidinyl,
(4) pyrazinyl,
(5) pyridazinyl,
(6) 1,2,4-oxadiazolyl, and
(7) 1,3,4-oxadiazolyl, optionally mono or di-substituted with substituents $R^4$ and $R^5$, which are independently selected from the group consisting of
(a) —$C_{1-4}$alkyl optionally substituted with hydroxy,
(b) —$S(O)_nC_{1-4}$alkyl,
(c) —$C(O)$—$NR^{10}R^{11}$,
(d) $HET^4$, and
(e) halo,
wherein $HET^4$ is optionally mono or di-substituted with substituents selected from:
(1) halo,
(2) —CN,
(3) —OH,
(4) —$C_{1-4}$alkyl optionally substituted with hydroxy, halo or cyano,
(5) —$CF_3$,
(6) —$OC_{1-4}$alkyl optionally substituted with hydroxyl or halo,
(7) —C(O)OH, and
(8) —$C(O)O$—$C_{1-3}$alkyl, and
(9) —$C(O)$—$NR^{19}R^{20}$,
wherein $R^{10}$, $R^{11}$, $R^{19}$ and $R^{20}$ are each independently selected from H and $C_{1-4}$alkyl. $R^2$ is selected from the group consisting of:
(1) phenyl,
(2) pyridyl,
(3) pyridazinyl,
(4) pyrimidyl,
(5) pyrazinyl,
(6) thiazolyl,
(7) oxazolyl,
(8) pyrazolyl,
(9) 1,2,4-oxadiazolyl, and
(10) 1,3,4-oxadiazolyl,
wherein $R^2$ is optionally mono or di-substituted with halo, $OC_{1-4}$alkyl optionally substituted with halogen, —$C_{1-4}$haloalkyl, hydroxyl and CN; and
$R^3$ is selected from the group consisting of:
(1) phenyl,
(2) pyrimidyl,
(3) pyridyl,
wherein $R^3$ is optionally mono or di-substituted with halo, halo$C_{1-4}$alkyl, or —$OC_{1-4}$alkyl optionally substituted with halo.

Within this genus there is a sub-genus of the Formula

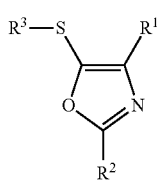

Ia wherein:
$R^1$ is selected from the group consisting of:
(1) phenyl,
(2) pyridyl,
(3) pyridazinyl,
(4) pyrimidyl,
(5) pyrazinyl,
wherein $R^1$ is optionally mono or di-substituted with substituents $R^4$ and $R^5$, which are independently selected from the group consisting of (a) halo,
(b) —CN,
(c) mono, di or tri-halo $C_{1-4}$ alkyl,
(d) —O—$C_{1-4}$alkyl, optionally substituted with hydroxyl, halo or amino
(e) —$C(CH_3)_2$—OH;
$R^2$ is selected from the group consisting of:
(1) phenyl,
(2) pyridyl,
(3) pyridazinyl,
(4) pyrimidyl,
(5) pyrazinyl,
(6) pyrazolyl,
wherein $R^2$ is optionally mono or di-substituted with halo, $OC_{1-4}$alkyl optionally substituted with halogen, —$C_{1-4}$haloalkyl, hydroxyl and CN; and
$R^3$ is selected from the group consisting of:
(1) phenyl,
(2) pyrimidyl,
(3) pyridyl,
wherein $R^3$ is optionally mono or di-substituted with halo, halo$C_{1-4}$alkyl, or —$OC_{1-4}$alkyl optionally substituted with halo.

Within this sub-genus there is a class wherein:
13. A compound of Claim 12 wherein:
$R^1$ is selected from the group consisting of:
(1) phenyl,
(2) pyridyl,
(3) pyrazinyl,
wherein $R^1$ is optionally mono or di-substituted with substituents $R^4$ and $R^5$, which are independently selected from the group consisting of:
(a) halo,
(b) —CN,
(c) mono, di or tri-halo $C_{1-4}$ alkyl,
(d) —O—$C_{1-4}$alkyl, optionally substituted with hydroxyl, halo or amino
(e) —$C(CH_3)_2$—OH;
$R^2$ is selected from the group consisting of:
(1) phenyl,
(2) pyridyl,
wherein $R^2$ is optionally mono or di-substituted with halo, $OC_{1-4}$alkyl optionally substituted with halogen, —$C_{1-4}$haloalkyl, hydroxyl and CN; and
$R^3$ is selected from the group consisting of:
(1) phenyl,
(2) pyrimidyl,
(3) pyridyl,
wherein $R^3$ is optionally mono or di-substituted with halo, halo$C_{1-4}$alkyl, or —$OC_{1-4}$alkyl optionally substituted with halo.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

The invention is described using the following definitions unless otherwise indicated.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkylthio" means alkylthio groups having the indicated number of carbon atoms of a straight, branched or cyclic configuration. $C_{1-6}$alkylthio, for example, includes methylthio, propylthio, isopropylthio, and the like.

The term "alkenyl" means linear or branched structures and combinations thereof, of the indicated number of carbon atoms, having at least one carbon-to-carbon double bond, wherein any hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes propynyl, 1-methylethynyl, butynyl and the like.

The term "cycloalkyl" means mono-, bi- or tri-cyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "aryl" is defined as a mono- or bi-cyclic aromatic ring system and includes, for example, phenyl, naphthyl, and the like.

The term "aralkyl" means an alkyl group as defined above of 1 to 6 carbon atoms with an aryl group as defined above substituted for one of the alkyl hydrogen atoms, for example, benzyl and the like.

The term "aryloxy" means an aryl group as defined above attached to a molecule by an oxygen atom (aryl-O) and includes, for example, phenoxy, naphthoxy and the like.

The term "aralkoxy" means an aralkyl group as defined above attached to a molecule by an oxygen atom (aralkyl-O) and includes, for example, benzyloxy, and the like.

The term "arylthio" is defined as an aryl group as defined above attached to a molecule by a sulfur atom (aryl-S) and includes, for example, thiophenyoxy, thionaphthoxy and the like.

The term "aroyl" means an aryl group as defined above attached to a molecule by an carbonyl group (aryl-C(O)—) and includes, for example, benzoyl, naphthoyl and the like.

The term "aroyloxy" means an aroyl group as defined above attached to a molecule by an oxygen atom (aroyl-O) and includes, for example, benzoyloxy or benzoxy, naphthoyloxy and the like.

The term "HET", such as in "$HET^1$", "$HET^2$", "$HET^3$", "$HET^4$", and "$HET^5$" is defined as a 5- to 10-membered aromatic, partially aromatic or non-aromatic mono- or bicyclic ring, containing 1-4 heteroatoms selected from O, S and N, and optionally substituted with 1-2 oxo groups. Where applicable, the Het group shall be defined to include the N-oxide. Preferably, "HET" is a 5- or 6-membered aromatic or non-aromatic monocyclic ring containing 1-3 heteroatoms selected from O, S and N, for example, pyridine, pyrimidine, pyridazine, furan, thiophene, thiazole, oxazole, isooxazole and the like, or HET is a 9- or 10-membered aromatic or partially aromatic bicyclic ring containing 1-3 heteroatoms selected from O, S, and N, for example, benzofuran, benzothiophene, indole, pyranopyrrole, benzopyran, quionoline, benzocyclohexyl, naphtyridine and the like. "HET" also includes the following: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl. In one aspect "HET" is selected from pyridyl, pyridazinyl, pyrimidinyl, pyrazinyl, thiazolyl, thienyl, pyrrolyl, oxazolyl, and oxadiazole;

For all of the above definitions, each reference to a group is independent of all other references to the same group when referred to in the Specification. For example, if both $R^1$ and $R^2$ are HET, the definitions of HET are independent of each other and $R^1$ and $R^2$ may be different HET groups, for example furan and thiophene.

The ability of the compounds of Formula I to selectively inhibit FAAH makes them useful for treating, preventing or reversing the progression of a variety of inflammatory and non-inflammatory diseases and conditions.

Diseases, disorders, syndromes and/or conditions, that would benefit from inhibition of FAAH enzymatic activity include, for example, Alzheimer's Disease, schizophrenia, depression, alcoholism, addiction, suicide, Parkinson's disease, Huntington's disease, stroke, emesis, miscarriage, embryo implantation, endotoxic shock, liver cirrhosis, atherosclerosis, cancer, traumatic head injury, glaucoma, and bone cement implantation syndrome.

Other diseases, disorders, syndromes and/or conditions that would benefit from inhibition of FAAH activity, include, for example, multiple sclerosis, retinitis, amyotrophic lateral sclerosis, immunodeficiency virus-induced encephalitis, attention-deficit hyperactivity disorder, pain, nociceptive pain, neuropathic pain, inflammatory pain, noninflammatory pain, painful hemorrhagic cystitis, obesity, hyperlipidemia, metabolic disorders, feeding and fasting, alteration of appetite, stress, memory, aging, hypertension, septic shock, cardiogenic shock, intestinal inflammation and motility, irritable bowel syndrome, colitis, diarrhea, ileitis, ischemia, cerebral ischemia, hepatic ischemia, myocardial infarction, cerebral excitotoxicity, seizures, febrile seizures, neurotoxicity, neuropathies, sleep, induction of sleep, prolongation of sleep, insomnia, and inflammatory diseases. Neurological and psychological disorders that would benefit from inhibition of FAAH activity include, for example, pain, depression, anxiety, generalized anxiety disorder (GAD), obsessive compulsive disorders, stress, stress urinary incontinence, attention deficit hyperactivity disorders, schizophrenia, psychosis, Parkinson's disease, muscle spasticity, epilepsy, diskenesia, seizure disorders, jet lag, and insomnia.

FAAH inhibitors can also be used in the treatment of a variety of metabolic syndromes, diseases, disorders and/or conditions, including but not limited to, insulin resistance syndrome, diabetes, hyperlipidemia, fatty liver disease, obesity, atherosclerosis and arteriosclerosis. FAAH inhibitors are useful in the treatment of a variety of painful syndromes, diseases, disorders and/or conditions, including but not limited to those characterized by non-inflammatory pain, inflammatory pain, peripheral neuropathic pain, central pain, deafferentiation pain, chronic nociceptive pain, stimulus of nociceptive receptors, phantom and transient acute pain.

Inhibition of FAAH activity can also be used in the treatment of a variety of conditions involving inflammation. These conditions include, but are not limited to arthritis (such as rheumatoid arthritis, shoulder tendonitis or bursitis, gouty arthritis, and aolymyalgia rheumatica), organ-specific inflammatory diseases (such as thyroiditis, hepatitis, inflammatory bowel diseases), asthma, other autoimmune diseases (such as multiple sclerosis), chronic obstructive pulmonary disease (COPD), allergic rhinitis, and cardiovascular diseases.

In some cases, FAAH inhibitors are useful in preventing neurodegeneration or for neuroprotection.

In addition, it has been shown that when FAAH activity is reduced or absent, one of its substrates, anandamide, acts as a substrate for COX-2, which converts anandamide to prostamides (Weber et al J Lipid. Res. 2004; 45:757). Concentrations of certain prostamides may be elevated in the presence of a FAAH inhibitor. Certain prostamides are associated with reduced intraocular pressure and ocular hypotensivity. Thus, in one embodiment, FAAH inhibitors may be useful for treating glaucoma.

In some embodiments, FAAH inhibitors can be used to treat or reduce the risk of EMDs, which include, but are not limited to, obesity, appetite disorders, overweight, cellulite, Type I and Type I1 diabetes, hyperglycemia, dyslipidemia, steatohepatitis, liver steatosis, non-alcoholic steatohepatitis, Syndrome X, insulin resistance, diabetic dyslipidemia, anorexia, bulimia, anorexia nervosa, hyperlipidemia, hypertriglyceridemia, atherosclerosis, arteriosclerosis, inflammatory disorders or conditions, Alzheimer's disease, Crohn's disease, vascular inflammation, inflammatory bowel disorders, rheumatoid arthritis, asthma, thrombosis, or cachexia.

In other embodiments, FAAH inhibitors can be used to treat or reduce the risk of insulin resistance syndrome and diabetes, i.e., both primary essential diabetes such as Type I Diabetes or Type I1 Diabetes and secondary nonessential diabetes. Administering a composition containing a therapeutically effective amount of an in vivo FAAH inhibitor reduces the severity of a symptom of diabetes or the risk of developing a symptom of diabetes, such as atherosclerosis, hypertension, hyperlipidemia, liver steatosis, nephropathy, neuropathy, retinopathy, foot ulceration, or cataracts.

In another embodiment, FAAH inhibitors can be used to treat food abuse behaviors, especially those liable to cause excess weight, e.g., bulimia, appetite for sugars or fats, and non-insulin-dependent diabetes.

In some embodiments, FAAH inhibitors can be used to treat a subject suffering from an EMD and also suffers from a depressive disorder or from an anxiety disorder. Preferably, the subject is diagnosed as suffering from the depressive or psychiatric disorder prior to administration of the FAAH inhibitor composition. Thus, a dose of a FAAH inhibitor that is therapeutically effective for both the EMD and the depressive or anxiety disorder is administered to the subject.

Preferably, the subject to be treated is human. However, the methods can also be used to treat non-human mammals. Animal models of EMDs such as those described in, e.g., U.S. Pat. No. 6,946,491 are particularly useful.

FAAH inhibitor compositions can also be used to decrease body-weight in individuals wishing to decrease their body weight for cosmetic, but not necessarily medical considerations.

A FAAH inhibitor composition can be administered in combination with a drug for lowering circulating cholesterol levels (e.g., statins, niacin, fibric acid derivatives, or bile acid binding resins). FAAH inhibitor compositions can also be used in combination with a weight loss drug, e.g., orlistat or an appetite suppressant such as diethylpropion, mazindole, orlistat, phendimetrazine, phentermine, or sibutramine.

The term "treating" encompasses not only treating a patient to relieve the patient of the signs and symptoms of the disease or condition but also prophylactically treating an asymptomatic patient to prevent the onset of the disease or condition or preventing, slowing or reversing the progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The term "treating" encompasses not only treating a patient to relieve the patient of the signs and symptoms of the disease or condition but also prophylactically treating an asymptomatic patient to prevent the onset of the disease or condition or preventing, slowing or reversing the progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The following abbreviations have the indicated meanings:
AIBN=2.2'-azobisisobutyronitrile
B.P.=benzoyl peroxide
Bn=benzyl
$CCl_4$=carbon tetrachloride
D=—O$(CH_2)_3$O
DAST=diethylamine sulfur trifluoride
DCC=dicyclohexyl carbodiimide
DCI=1-(3-dimethylaminopropyl)-3-ethyl carbodiimide
DEAD=diethyl azodicarboxylate
DIBAL=diisobutyl aluminum hydride
DME=ethylene glycol dimethylether
DMAP=4-(dimethylamino)pyridine
DMF=N,N-dimethylformamide
DMSO=dimethyl sulfoxide
$Et_3N$=triethylamine
LDA=lithium diisopropylamide
m-CPBA=metachloroperbenzoic acid
NBS=N-bromosuccinimide
NSAID=non-steroidal anti-inflammatory drug
PCC=pyridinium chlorochromate
PDC=pyridinium dichromate
Ph=phenyl
1,2-Ph=1,2-benzenediyl
Pyr=pyridinediyl
Qn=7-chloroquinolin-2-yl
$R^S$=—$CH_2SCH_2CH_2$Ph
r.t.=room temperature
rac.=racemic
THF=tetrahydrofuran
THP=tetrahydropyran-2-yl Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for oral administration to humans may contain from about 0.5 mg to about 5 g of active agent compounded with an appropriate and convenient amount of carrier material which may vary from about 5 to about 95 percent of the total composition. Dosage unit forms will generally contain from about 1 mg to about 2 g of an active ingredient, typically 25 mg, 50 mg, 100 mg, 200 mg, 300 mg, 400 mg, 500 mg, 600 mg, 800 mg, or 1000 mg.

For the treatment of FAAH mediated diseases the compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, solutions, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGS and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing a compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Assays

The following assays illustrate the utility of the invention:

The compounds of the invention underwent pharmacological evaluations to determine their inhibitory effect on the enzyme FAAH (Fatty Acid Amide Hydrolase).

To assist in assay development stable cell lines for human, murine and rat full length FAAH were developed. Human FAAH cDNA (Acccssion No: NM_001441.1) was purchased from Origene (Rockville, Md.). The full length FAAH was subcloned into the mammalian expression vector, pcDEF.neo, using XbaI and EcoRI restriction sites and used for stable cell line generation.

| Construct | Primer | Sequence |
|---|---|---|
| Full length rodent FAAH | 1 | (SEQ ID NO: 1) CAAGGTACCGCCACCATGGTGCTGAGCGAAGTGTGG |
| Full length | 2 | (SEQ ID NO: 2) CCGGAATTCTCAAGATGGCCGCTTTTCAGG |

-continued

| Construct | Primer | Sequence |
|---|---|---|
| murine FAAH | | |
| Full length rat FAAH | 3 | CCGGAATTCTCACGATGGCTGCTTTTGAGG (SEQ ID NO: 3) |

Murine (accession number NM_010173) and Rat FAAH (accession number NM_024132) was amplified by reverse transcriptase polymerase chain reaction (RT-PCR) from brain cDNA (BD Biosciences, San Jose, Calif.) using primers 1 and 2 or primers 1 and 3 respectively (see Table). The resulting PCR product was ligated into pCR4 TOPO and DNA sequence confirmed. The full length murine FAAH was subcloned into the mammalian expression vector, pcDEFneo using either EcoRI (murine) or KpnI and EcoRI (rat) restriction sites. Chinese hamster ovary cells (CHO) were transfected following manufacturers protocol (AMAXA). Forty eight hours post transfection, cells were trypsinized and transferred to 96 well plates in Iscove's DMEM media supplemented with 2 mM Glutamine, 10% fetal calf serum, 1 mg/ml geneticin and HT Supplement (0.1 mM sodium hypoxanthine, 0.016 mM thymidine) in order to isolate single clones. Following selection in geneticin, individual clones were selected and FAAH activity was assessed using a whole cell fluorescent anandamide assay, modified from Ramarao et al (2005). Following removal of tissue culture media cells were dislodged following addition of Cellstripper (Mediatech, Inc. Manassas, Va.) and transferred to 96 well black clear bottom assay plate, centrifuged at 1,000 rpm for 3 mins and media removed and replaced with assay buffer (50 mM Tris pH8.0, 1 mM EDTA, 0.1% fatty acid free BSA). The reaction was initiated by addition of fluorescent substrate, AMC Arachidonoyl Amide (Cayman Chemical, Ann Arbor, Mich.) to 1 µM and reaction allowed to proceed for 2 hours at room temperature. Release of fluorescence was monitored in a CytoFluor Multiplate Reader. Cells expressing the highest amount of FAAH activity were selected for study with FAAH inhibitors.

Preparation of Lysate and Microsomes

CHO cells expressing FAAH were used to prepare either crude cell lysate or microsome fractions. To harvest cells, tissue culture media was decanted, the monolayer washed three times with $Ca^{++}Mg^{++}$ free PBS and cells recovered after 15 min in enzyme free dissociation media (Millipore Corp, Billerica, Mass.). Cells were collected by centrifuging at 2000 rpm for 15 min. and the cell pellet re-suspended with 50 mM HEPES (pH 7.4) containing 1 mM EDTA and the protease inhibitors aprotinin (1 mg/ml) and leupeptin (100 µM). The suspension was sonicated at 4° C. and the cell lysate recovered after centrifuging at 12,000×g (14,600 rpm, SS34 rotor) for 20 min at 4° C. to form a crude pellet of cell debris, nuclei, peroxisomes, lysosomes, and mitochondria; the supernatant or cell lysate was used for FAAH enzyme assay. In some cases, microsomes fractions enriched in FAAH were prepared by centrifuging the cell lysate further at 27,000 rpm (100,000×g) in SW28 rotor for 50 minutes at 4° C. The pellet containing FAAH-enriched microsomes was re-suspend in 50 mM HEPES, (pH 7.4) 1 mM EDTA, and any remaining DNA sheared by passage of material through a 23 gauge needle and aliquots of enzyme were store at −80° C. prior to use.

FAAH Assays

Several assays have been used to demonstrate the inhibitory activity. Enzyme activity was demonstrated in a radioenzymatic test based on measuring the product of hydrolysis (ethanolamine [$^3$H]) of anandamide [ethanolamine 1-.sup.3H](American Radiolabeled Chemicals; 1 mCi/ml) with FAAH (Life Sciences (1995), 56, 1999-2005 and Journal of Pharmacology and Experimented Therapeutics (1997), 283, 729-734), Analytical. Biochemistry (2003), 318, 270-5. In addition, routine assays were performed monitoring hydrolysis of arachidonyl-7-amino-4-methylcoumarin amide (AAMCA) by following increase in fluorescence upon release of 7-amino-4-methyl coumarin ($\lambda_{EX}$=355 nm, $\lambda_{EM}$=460 nm). Analytical. Biochemistry (2005). 343, 143-51

Assays are performed on either cell lysate or microsome fractions prepared as described or in whole cell format employing either the fluorescent substrate AAMCA (Cayman chemical, Ann Arbor, Mich.,) or $^3$H-anandmaide ([ETHANOLAMINE-1-3H]American Radiolabeled Chemicals; 1 mCi/ml). The cell lysate or microsome assay is performed in Costar black wall, clear bottom plates by adding FAAH_CHO (whole cell, cell lysate or microsome) in assay buffer (50 mM Phosphate, pH 8.0, 1 mM EDTA, 200 mM KCl, 0.2% glycerol, 0.1% fatty acid free BSA) to each well, followed by either DMSO or compound and allowed to incubate at 22-25° C. for fifteen minutes. AAMCA substrate was used to achieve a final concentration of 1 µM and reaction allowed to proceed at room temperature for 1-3 hours. Fluorescent release as a measure of FAAH activity was monitored by reading the plate in a CytoFluor Multiplate Reader (Ex: 360/40 nM; Em: 460/40 nM). Whole cell assay is conducted with cells harvested after rinsing tissue culture flasks three times with $Ca^{++}Mg^{++}$ free PBS, incubating for 10 min in Enzyme free dissociation media and centrifuging for 5 minutes at 1,000 rpm in table top centrifuge. Cells are resuspended in assay buffer at desired cell number in ($4\times10^4$ cells/assay in 96-well format; $1\times10^4$ cells/assay in 384-well format) and assayed as described.

Alternatively, assays are performed using anandamide [ethanolamine 1-.sup.3H] (specific activity of 10 Ci/mmol) diluted with cold anandamide to achieve a final assay concentration of 1 µM anandamide (~50,000 cpm). Enzyme (CHO cell lysate, brain or liver homogenate) is incubated in assay buffer (50 mM Phosphate, pH 8.0, 1 mM EDTA, 200 mM KCl, 0.2% glycerol, 0.1% fatty acid free BSA) with inhibitor at 25° C. for 30 minutes. The reaction was terminated by addition of 2 volumes of chloroform:methanol (1:1) and mixed by vortexing. Following a centrifugation step, 2000 rpm for 10 min. at room temperature, the aqueous phase containing the released $^3$H-ethanolamide was recovered and quantitated by liquid scintillation as a reflection of FAAH enzyme activity.

Ramarao M. K., et al. A fluorescence-based assay for fatty acid amide hydrolase compatible with high-throughput screening. Anal Biochem. 343:143-51 (2005)

Wilson S. J. et 1. A high-throughput-compatible assay for determining the activity of fatty acid amide hydrolase. Anal Biochem. 318:270-5 (2003).

Each of Examples 1 through 56 was tested and found to demonstrate biological activity. Results for specific Examples are provided below. Each of Examples 1 through 56 was found to have and IC50 of 3 µM or lower in these assays.

| Example | Human Lysate IC50 (nM) | Human whole cell IC50 (nM) | Rat whole cell IC50 (nM) |
|---------|------------------------|----------------------------|--------------------------|
| Ex 3    | 23                     | 71                         | 44                       |
| Ex 12   | 19                     | 25                         | 13                       |
| Ex 19   | 38                     | 78                         | 18                       |
| Ex 20   | 43                     | 59                         | 29                       |
| Ex 35   | 27                     | 37                         | 21                       |
| Ex 37   | 13                     | 40                         | 15                       |
| Ex 46   | 17                     | 39                         | 10                       |
| Ex 48   | 9                      | 77                         | 8                        |
| Ex 51   | 26                     | 148                        | 107                      |
| Ex 56   | 15                     | 114                        | 16                       |

PREPARATION OF THE COMPOUNDS OF THE INVENTION

The compounds of the present invention can be prepared according to the procedures denoted in the following reaction Schemes and Examples or modifications thereof using readily available starting materials, reagents, and conventional procedures thereof well-known to a practioner of ordinary skill in the art of synthetic organic chemistry. Specific definitions of variables in the Schemes are given for illustrative purposes only and are not intended to limit the procedures described.

General Scheme

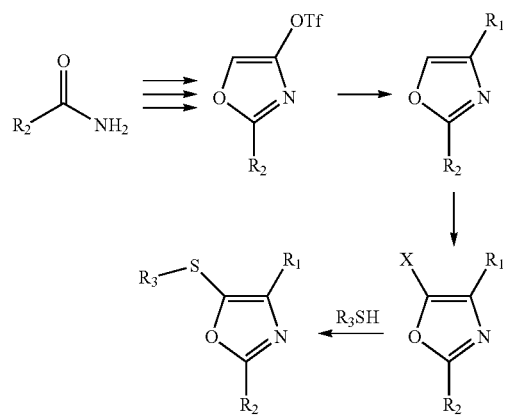

Intermediate 1

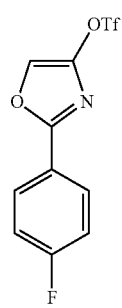 [SMILES: O=S(=O)(Oc1coc(-c2ccc(F)cc2)n1)C(F)(F)F]

2-(4-Fluorophenyl)-1,3-oxazol-4-yl trifluoromethanesulfonate

The title compound was prepared using the procedure described by Langille, N. F.; Dakin, L. A.; Panek, J. S. *Org. Lett.* 2002, 4, 2485.

Intermediate 2

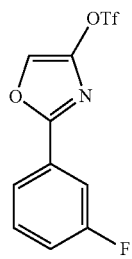 [SMILES: O=S(=O)(Oc1coc(-c2cccc(F)c2)n1)C(F)(F)F]

2-(3-Fluorophenyl)-1,3-oxazol-4-yl trifluoromethanesulfonate

The title compound was prepared using the procedure described by Langille, N. F.; Dakin, L. A.; Panek, J. S. *Org. Lett.* 2002, 4, 2485.

Intermediate 3

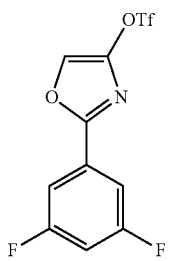 [SMILES: O=S(=O)(Oc1coc(-c2cc(F)cc(F)c2)n1)C(F)(F)F]

2-(3,5-Difluorophenyl-1,3-oxazol-4-yl trifluoromethanesulfonate

The title compound was prepared using the procedure described by Langille, N. F.; Dakin, L. A.; Panek, J. S. *Org. Lett.* 2002, 4, 2485.

Intermediate 4

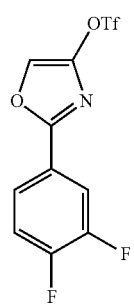 [SMILES: O=S(=O)(Oc1coc(-c2ccc(F)c(F)c2)n1)C(F)(F)F]

2-(3,4-Difluorophenyl)-1,3-oxazol-4-yl trifluoromethanesulfonate

The title compound was prepared using the procedure described by Langille, N. F.; Dakin, L. A.; Panck, J. S. *Org. Lett.* 2002, 4, 2485.

Intermediate 5

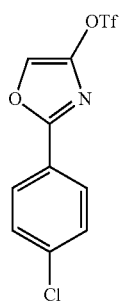 [SMILES: O=S(=O)(Oc1coc(-c2ccc(Cl)cc2)n1)C(F)(F)F]

2-(4-Chlorophenyl-1,3-oxazol-4-yl trifluoromethanesulfonate

The title compound was prepared using the procedure described by Langille, N. F.; Dakin, L. A.; Panek, J. S. *Org. Lett.* 2002, 4, 2485.

Intermediate 6

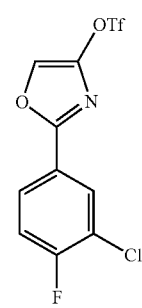 [SMILES: O=S(=O)(Oc1coc(-c2ccc(F)c(Cl)c2)n1)C(F)(F)F]

2-(3-Chloro-4-fluorophenyl)-1,3-oxazol-4-yl trifluoromethanesulfonate

The title compound was prepared using the procedure described by Langille, N. F.; Dakin, L. A.; Panek, J. S. *Org. Lett.* 2002, 4, 2485.

Intermediate 7

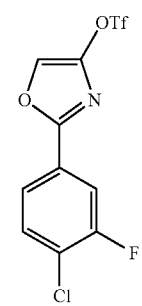 [SMILES: O=S(=O)(Oc1coc(-c2ccc(Cl)c(F)c2)n1)C(F)(F)F]

2-(4-Chloro-3-fluorophenyl)-1,3-oxazol-4-yl trifluoromethanesulfonate

The title compound was prepared using the procedure described by Langille, N. F.; Dakin, L. A.; Panek, J. S. *Org. Lett.* 2002, 4, 2485.

Intermediate 8

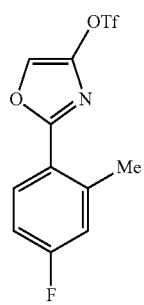 [SMILES: Cc1cc(F)ccc1-c1nc(OS(=O)(=O)C(F)(F)F)co1]

2-(4-Fluoro-2-methylphenyl)-1,3-oxazol-4-yl trifluoromethanesulfonate

The title compound was prepared using the procedure described by Langille, N. F.; Dakin, L. A.; Panek, J. S. *Org. Lett.* 2002, 4, 2485.

Intermediate 9

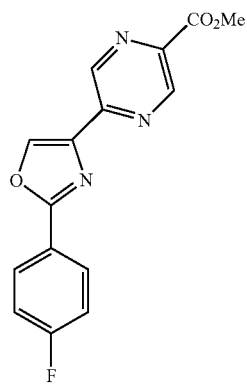

Methyl 5-[2-(4-fluorophenyl)-1,3-oxazol-4-yl]pyrazine-2-carboxylate

Step A

A solution of intermediate 1 (2.66 g, 8.55 mmol), bis-pinacolatodiboron (2.60 g, 10.3 mmol), KOAc (1.68 g, 17.1 mmol), and Pd(dppf)Cl$_1$ (0.70 g, 0.86 mmol) in 1,4-dioxane (25 mL) were heated to 140° C. for 30 min. Upon completion of the reaction as judged by TLC analysis, the solution was concentrated to dryness and purified on silica gel to afford the corresponding boronic acid intermediate which was taken on immediately.

Step B

The boronic acid prepared in Step A (1.00 g, 4.80 mmol), methyl 5-chloropyrazine-2-carboxylate (1.70 g, 10.0 mmol), Pd(PPh$_3$)$_4$ (558 mg, 0.48 mmol), K$_2$CO$_3$ (2.00 g, 14.5 mmol) were dissolved in toluene (10 mL) and H$_2$O (1 mL) and degassed for 5 min. After which, the solution was heated in the microwave reactor to 120° C. for 30 min. Upon completion of the reaction as judged by TLC analysis, the solution was diluted with dist H$_2$O and extracted with EtOAc. The organic layer was removed, dried over MgSO$_4$, filtered and concentrated giving rise to an oil. The oil was purified on silica gel to afford the title compound (290 mg). LC/MS: m/e 300.1 (M+H).

Intermediate 10

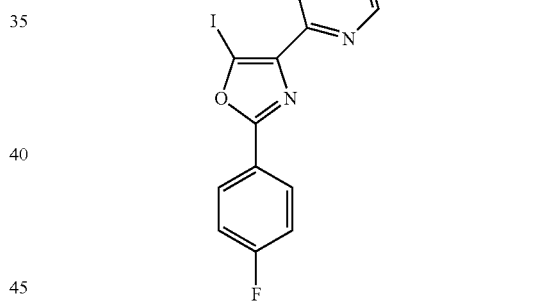

2-Pyrazinecarboxylic acid, 5-[2-(4-fluorophenyl)-5-iodo-4-oxazolyl]-methyl ester A solution of Intermediate 9 (1.40 g, 4.70 mmol), NIS (1.30 g, 5.60 mmol), TFA (0.40 mL) in CH$_3$CN (100 mL) was stirred at rt for 12 h. Upon completion of the reaction, the solution was diluted with sat aq Na$_2$S$_2$O$_3$ and extracted with EtOAc. The organic layer was removed, dried over MgSO$_4$, filtered and concentrated giving rise to an oil. The oil was purified on silica gel to afford the title compound (684 mg).

LC/MS: m/e 425.9 (M+H)+. 1H NMR (500 MHz, Acetone-d6): δ 4.01 (s, 3H), 7.41 (t, J=8.8 Hz, 2H), 8.20-8.25 (m, 2H), 9.28 (s, 1H), 9.39 (s, 1H).

Intermediate 11

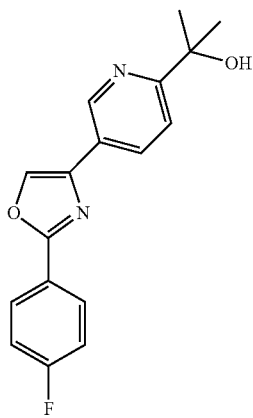

2-{5-[2-(4-Fluorophenyl)-1,3-oxazol-4-yl]pyridin-2-yl}propan-2-ol

A solution of Intermediate 1 (60 g, 0.20 mol), bis-pinacolatodiboron (500 g, 0.25 mol), KOAc (57.0, 0.58 mol), Pd(dppf)Cl₂ (7.90 g, 9.60 mmol), and dppf (5.34 g, 9.60 mmol) in 1,4-dioxane (1.6 L) were heated to 101° C. for 3 h. Upon completion of the reaction as judged by TLC analysis, the reaction was allowed to cool to 65° C. At which point, 2-(5-bromopyridin-2-yl)propan-2-ol (62.6 g, 0.30 mol) and Pd(PPh₃)₂Cl₂ (13.6 g, 0.02 mol) were added followed by dropwise addition of aqueous Na₂CO₃ (193 mL, 0.40 mol, 2 M). The solution was heated to 91° C. for 12 h. Upon completion of the reaction as judged by LC/MS analysis, the solution was diluted with dist H₂O and extracted with EtOAc (2×). The combined organic layers were removed, dried over MgSO₄, filtered and concentrated giving rise to an oil. The oil was purified on silica gel to give afford the title compound (38.50 g). LC/MS: m/e 299.1 (M+H).

Intermediate 12

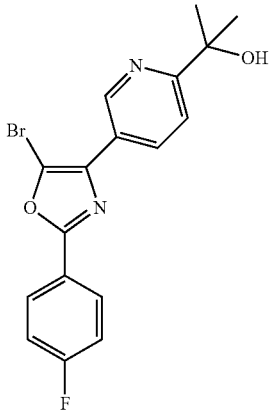

2-{5-[5-Bromo-2-(4-fluorophenyl)-1,3-oxazol-4-yl]pyridin-2-yl}propan-2-ol

A solution of Intermediate 11 (38.5 g, 0.13 mol) and NBS (28.0 g, 0.16 mol) in CH₂Cl₂ (1340 mL) was stirred at rt for 12 h. Upon completion of the reaction, the solution was diluted with sat aq NaS₂O₃ solution. The organic layer was removed, dried over MgSO₄, filtered and concentrated giving rise to an oil. The oil was purified on silica gel to afford the title compound (31.97 g). LC/MS: m/e 377.0 (M+H)+.

Intermediate 13

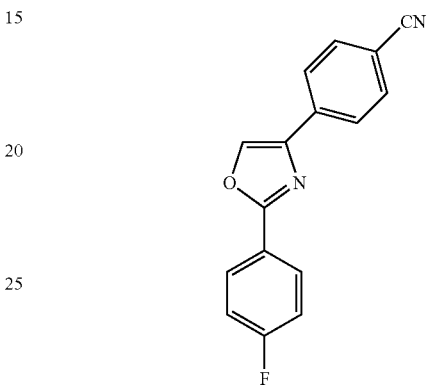

4-[2-(4-Fluorophenyl)-1,3-oxazol-4-yl]benzonitrile

A solution of Intermediate 1 (560 mg, 1.80 mol), (4-cyanophenyl)boronic acid (291 mg, 2.00 mmol), K₂CO₃ (497 mg, 3.60 mmol) and Pd(PPh₃)₄ (104 mg, 0.09 mmol) in 1,4-dioxane (10 mL) were heated to 110° C. for 20 min. Upon completion of the reaction as judged by TLC analysis, the reaction was concentrated to dryness and purified on silica gel to afford the title compound (470 mg). LC/MS: m/e 265.2 (M+H).

Intermediate 14

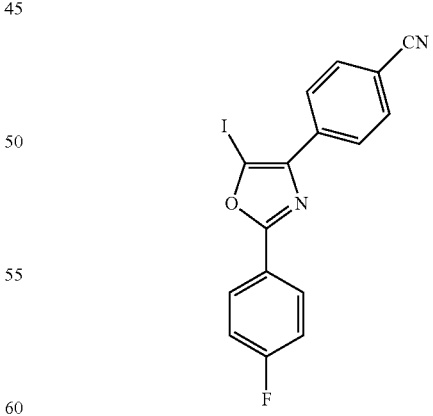

4-[2-(4-Fluorophenyl)-5-iodo-1,3-oxazol-4-yl]benzonitrile

A solution of Intermediate 13 (476 mg, 1.80 mmol), NIS (608 mg, 2.70 mmol), TFA (0.14 mL) in CH₂Cl₂ (15 mL) was stirred at rt for 12 h. Upon completion of the reaction, the solution was diluted with sat aq Na$_2$S$_2$O$_3$ and extracted with EtOAc. The organic layer was removed, dried over MgSO$_4$, filtered and concentrated giving rise to an oil. The oil was purified on silica gel to afford the title compound (700 mg). LC/MS: m/e 391.1 (M+H)$^+$. $^1$H NMR (500 MHz, Acetone-d6): δ 7.41 (t, 2H), 7.94 (d, 2H), 8.20 (m, 2H), 8.36 (d, 2H).

Intermediate 15

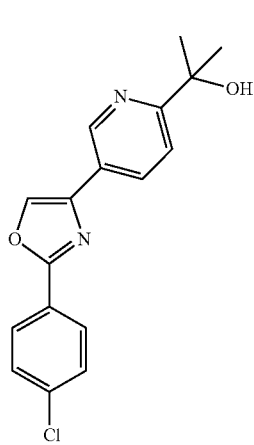

2-{5-[2-(4-Chlorophenyl)-1,3-oxazol-4-yl]pyridin-2-yl}propan-2-ol

The target compound was prepared in an analogous manner to Intermediate 11 except that Intermediate 5 was coupled with 2-(5-bromopyridin-2-yl)propan-2-ol (XXX g). LC/MS: m/e 315.1 (M+H).

Intermediate 16

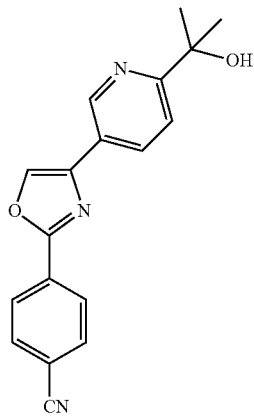 [SMILES: CC(C)(O)c1ccc(-c2coc(-c3ccc(Cl)cc3)n2)cn1]

4-{4-[6-(1-Hydroxy-1-methylethyl)pyridin-3-yl]-1,3-oxazol-2-yl}benzonitrile

A solution of Intermediate 15 (200 mg, 0.60 mmol), Pd$_2$dba$_3$ (93 mg, 0.10 mmol), S-Phos (104 mg, 0.25 mmol) and Zn(CN)$_2$ (112 mg, 0.90 mmol) in 10 mL of 99:1 v:v DMF:H$_2$O were heated to 180° C. for 30 min in the microwave reactor. Upon completion of the reaction as judged by LC/MS analysis, the solution was diluted with dist H$_2$O and extracted with EtOAc (2×). The combined organic layers were removed, dried over MgSO$_4$, filtered and concentrated giving rise to an oil. The oil was purified on silica gel to afford the title compound (194 mg). LC/MS: m/e 306.1 (M+H).

Intermediate 17

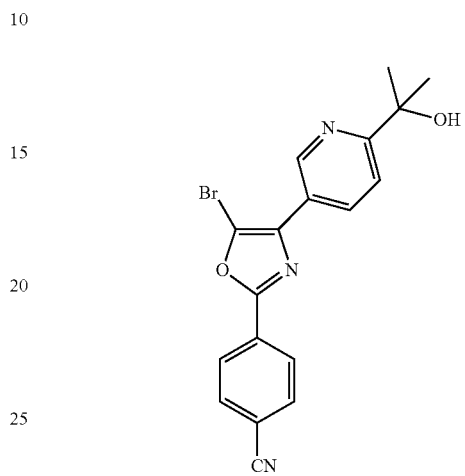

4-{5-Bromo-4-[6-(1-hydroxy-1-methylethyl)pyridin-3-yl]-1,3-oxazol-2-yl}benzonitrile A solution of Intermediate 16 (476 mg, 1.80 mmol) and NBS (608 mg, 2.70 mmol) in CH$_2$Cl$_2$ (15 mL) was stirred at rt for 12 h. Upon completion of the reaction, the solution was diluted with sat aq Na$_2$S$_2$O$_3$ and extracted with EtOAc. The organic layer was removed, dried over MgSO$_4$, filtered and concentrated giving rise to an oil. The oil was purified on silica gel to afford the title compound (43.7 mg). LC/MS: m/e 384.0 (M+H)$^+$.

Example 1

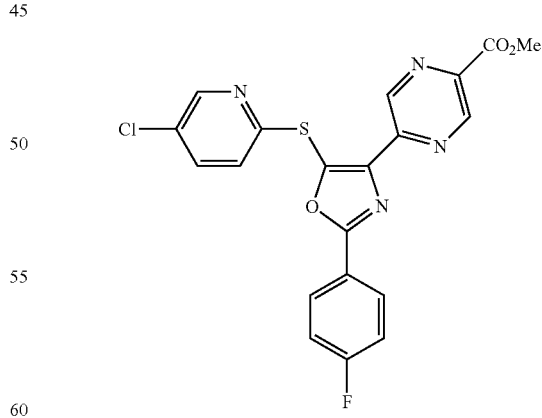

Methyl-5-[5-[(5-chloropyridin-2-yl)thio]-2-(4-fluorophenyl)-1,3-oxazol-4-yl]pyrazine-2-carboxylate A solution of 5-chloropyridine-2-thiol (305 mg, 2.10 mmol) dissolved in 18 mL of NMP was treated with NaH (84 mg, 2.10 mmol). The resulting solution was stirred for 30 min at rt before Intermediate 10 (684 mg, 1.60 mmol) and CuI (306 mg, 1.60 mmol) were added to the solution. The resulting dark solution was heated to 120° C. for 2 h. After which point, the solution was poured into a rapidly stirred solution of 9:1 NH$_4$Cl:NH$_4$OH and EtOAc. Upon clarification of the organic layer, removal of the organic layer was followed by drying over MgSO$_4$, filtration and concentration giving rise to an oil. The oil was purified on silica gel to afford the title compound (410 mg). LC/MS: m/e 443.0 (M+H)$^+$. $^1$H NMR (500 MHz, Acetone-d6): δ 4.01 (s, 3H), 7.37-7.41 (m, 2H), 8.04 (m, 2H), 8.70 (s, 1H), 9.28 (d, J=1.5 Hz, 1H), 9.44 (d, J=1.0 Hz, 1H).

The compounds in Table 1 were prepared from the appropriate starting materials using the procedure for Example 1.

treated with methylmagnesium bromide (3.1 mL, 9.3 mmol, 3.0 M in THF) at rt. Upon completion of the reaction as judged by TLC analysis, the solution was diluted with saturated aq NH$_4$Cl solution and extracted with EtOAc. The organic layer was removed, dried over MgSO$_4$, filtered and concentrated giving rise to an oil. The oil was purified on silica gel to afford the title compound (90 mg). LC/MS: m/e 442.9 (M+H)$^+$. $^1$H NMR (500 MHz, Acetone-d6): δ 1.58 (s, 6H), 4.58 (s, 1H), 7.42 (m, 3H), 7.76 (dd, J=2.6, 8.8 Hz, 2H), 8.32 (m, 2H), 8.43 (d, J=2.7 Hz, 1H), 8.96 (s, 1H), 9.19 (s, 1H).

The compounds in Table 2 were prepared from the appropriate starting materials using the procedure for Example 3.

TABLE 1

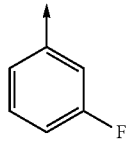

| Example | R$_2$ | R$_3$ | LCMS: found m/e (M + H) |
|---|---|---|---|
| 2 | 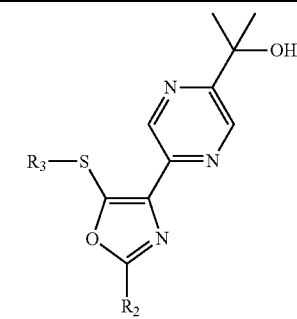 | 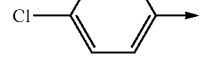 | 442.9 |

Example 3

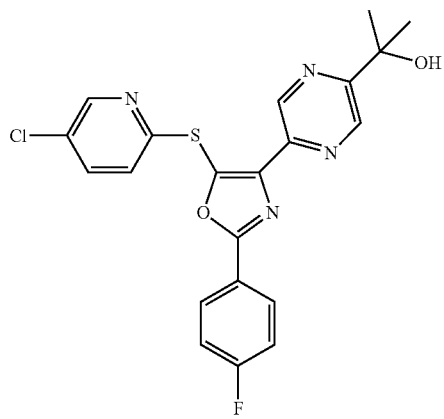 [SMILES: CC(C)(O)c1cnc(-c2nc(-c3ccc(F)cc3)oc2Sc2ccc(Cl)cn2)cn1]

2-{5-[5-[(5-Chloropyridin-2-yl)thio]-2-(4-fluorophenyl)-1,3-oxazol-4-yl]pyrazin-2-yl}propan-2-o A solution of methyl-5-[5-[(5-chloropyridin-2-yl)thio]-2-(4-fluorophenyl)-1,3-oxazol-4-yl]pyrazine-2-carboxylate (Example 1) (410 mg, 0.93 mmol) in THF (20 mL) was

TABLE 2

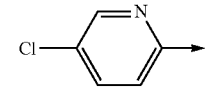

| Example | R$_2$ | R$_3$ | LCMS: found m/e (M + H) |
|---|---|---|---|
| 4 | 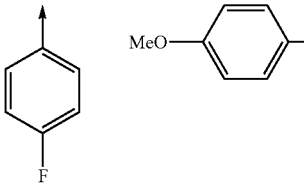 | 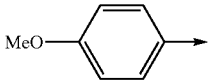 | 441.9 |
| 5 | 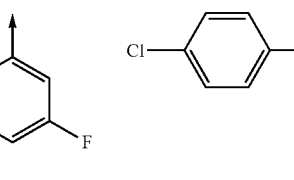 | 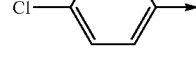 | 438.2 |
| 6 | 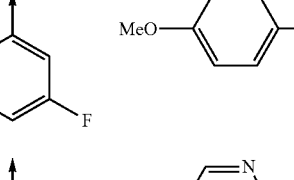 | 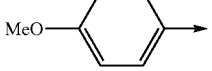 | 441.9 |
| 7 | 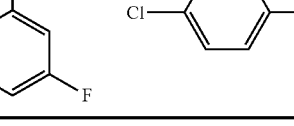 | 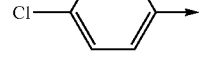 | 438.0 |
| 8 |  |  | 442.9 |

Example 9

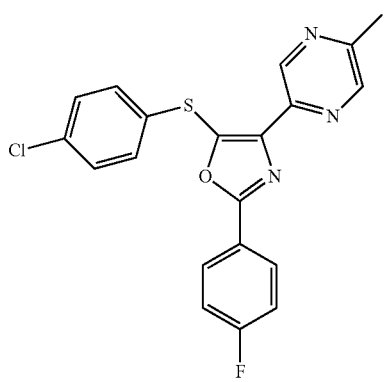 [SMILES: Cc1cnc(-c2nc(-c3ccc(F)cc3)oc2Sc2ccc(Cl)cc2)cn1]

2-[5-[(4-Chlorophenyl)thio]-2-(4-fluorophenyl)-1,3-oxazol-4-yl]-5-methylpyrazin

A solution of methyl-5-[5-[(4-chlorophenyl)thio]-2-(4-fluorophenyl)-1,3-oxazol-4-yl]pyrazine-2-carboxylate (Example 1) (24 mg, 0.05 mmol) in THF (5 mL) was treated with methylmagnesium bromide (0.2 mL, 0.5 mmol, 3.0 M in THF) at rt. Upon completion of the reaction as judged by TLC analysis, the solution was diluted with saturated aq NH$_4$Cl solution and extracted with EtOAc. The organic layer was removed, dried over MgSO$_4$, filtered and concentrated giving rise to an oil. The oil was purified on silica gel to afford the title compound (6.3 mg). LC/MS: m/e 397.0 (M+H)$^+$. $^1$H NMR (500 MHz, Acetone-d6): δ 2.55 (s, 3H), 7.46 (m, 5H), 8.06 (m, 2H), 8.50 (s, 1H), 8.55 (s, 1H), 9.10 (d, J=1.1 Hz, 1H).

The compounds in Table 3 were prepared from the appropriate starting materials using the procedure for Example 9.

TABLE 3

| Example | R$_2$ | R$_3$ | LCMS: found m/e (M + H) |
|---|---|---|---|
| 10 | 3-fluorophenyl | 4-methoxyphenyl | 394.1 |
| 11 | 3-fluorophenyl | 4-chlorophenyl | 397.9 |

Example 12

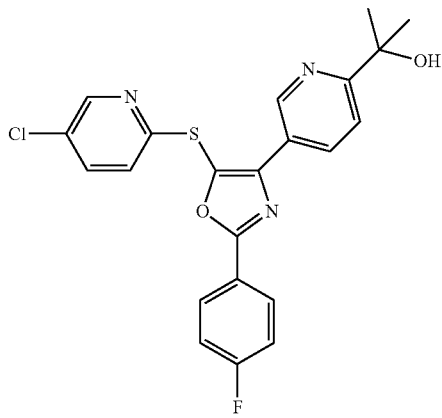

2-{5-[5-[(5-Chloropyridin-2-yl)thio]-2-(4-fluorophenyl)-1,3-oxazol-4-yl]pyridin-2-yl}propan-2-ol A solution of 5-chloropyridine-2-thiol (27.3 g, 0.20 mol) dissolved in 200 mL of NMP was treated with NaH (7.7 g, 0.20 mol). The resulting solution was stirred for 30 min at rt before Intermediate 12 (31.9 g, 0.08 mol) dissolved in 200 mL of NMP was added by addition funnel. Lastly, CuI (16.3 g, 0.08 mol) was added to the solution. The resulting dark solution was heated to 120° C. for 2 h. After which point, the solution was cooled to rt. Once at rt, the solution poured into a rapidly stirred solution of 9:1 NH$_4$Cl:NH$_4$OH and EtOAc. Upon clarification, the organic layer was removed followed by drying over MgSO$_4$, filtration and concentration giving rise to an oil. The oil was purified on silica gel to afford the title compound (31.87 g). LC/MS: m/e 442.1 (M+H)$^+$. $^1$H NMR (500 MHz, Acetone-d6): δ 1.76 (s, 6H), 5.01 (s, 1H), 7.40 (m, 3H), 7.80 (m, 2H), 8.25 (m, 2H), 8.44 (dd, J=2.3, 8.2 Hz, 1H), 8.44 (d, J=2.3 Hz, 1H), 9.20 (d, J=1.4 Hz, 1H).

Example 12[a]

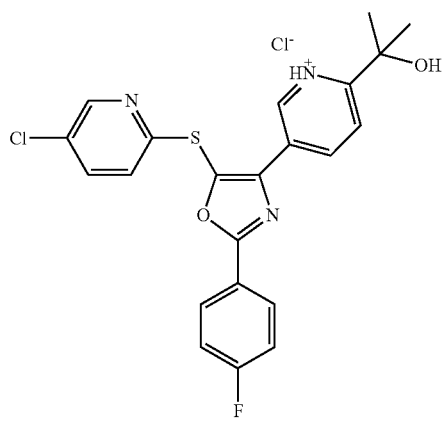 [SMILES: CC(C)(O)c1ccc(-c2nc(-c3ccc(F)cc3)oc2Sc2ccc(Cl)cn2)cn1 ; [Cl-]]

2-{5-[5-[(5-Chloropyridin-2-yl)thio]-2-(4-fluorophenyl)-1,3-oxazol-4-yl]pyridin-2-yl}propan-2-ol, hydrogen chloride salt A solution of Example 12 (138 mg, 0.31 mmol) was taken up in 7 mL of IPAC and heated to 65° C. Upon complete dissolution, HCL (78 μl, 0.31 mmol, 4N in dioxane) was added dropwise. The resulting slurry was maintained at 65° C. for 2 h before being allowed to cool to rt. The slurry was filtered giving rise to a white solid (100.7 mg). LC/MS: m/e 442.1 (M+H)+

The compounds in Table 4 were prepared from the appropriate starting materials using the procedure for Example 12.

TABLE 4

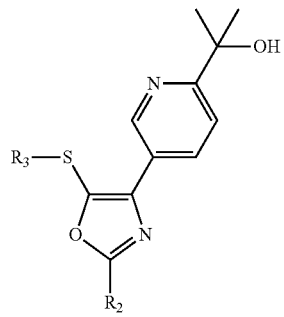

| Example | R₂ | R₃ | LCMS: found m/e (M + H) |
|---|---|---|---|
| 13 | 4-F-C₆H₄ | 4-Cl-C₆H₄ | 441.0 |
| 14 | 4-F-C₆H₄ | 4-MeO-C₆H₄ | 437.0 |
| 15 | 4-F-C₆H₄ | 2,4-diF-C₆H₃ | 443.0 |
| 16 | 4-F-C₆H₄ | 2-F-4-Cl-C₆H₃ | 459.0 |
| 17 | 4-F-C₆H₄ | 3,4-diF-C₆H₃ | 443.0 |
| 18 | 4-F-C₆H₄ | 3-F-4-MeO-C₆H₃ | 445.0 |
| 19 | 4-F-C₆H₄ | 5-F-pyridin-2-yl | 426.1 |

TABLE 4-continued

| Example | R₂ | R₃ | LCMS: found m/e (M + H) |
|---|---|---|---|
| 20 | 4-F-phenyl | 5-Cl-pyrimidin-2-yl | 442.9 |
| 21 | 4-F-phenyl | 6-MeO-pyridin-3-yl | 438.1 |
| 22 | 4-F-phenyl | 5-F-pyrimidin-2-yl | 427.0 |
| 23 | 4-F-phenyl | 5-MeO-pyrimidin-2-yl | 439.0 |
| 24 | 4-F-phenyl | 2-MeO-pyrimidin-5-yl | 439.0 |
| 25 | 4-F-phenyl | 5-Me-pyridin-2-yl | 422.1 |
| 26 | 4-F-phenyl | 5-cyclopropyl-pyridin-2-yl | 448.1 |
| 27 | 4-F-phenyl | 2,4,5-trifluorophenyl | 461.3 |
| 28 | 4-F-phenyl | 4-Cl-3-F-phenyl | 459.3 |
| 29 | 3-F-phenyl | 4-Cl-phenyl | 440.9 |
| 30 | 3-F-phenyl | 4-MeO-phenyl | 437.0 |
| 31 | 3-F-phenyl | 5-Cl-pyridin-2-yl | 442.0 |
| 32 | 3,5-diF-phenyl | 5-Cl-pyridin-2-yl | 459.9 |

TABLE 4-continued
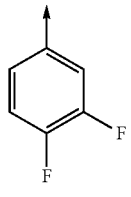
| Example | R₂ | R₃ | LCMS: found m/e (M + H) |
|---|---|---|---|
| 33 | 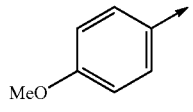 | 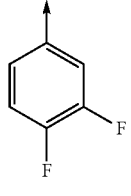 | 455.0 |
| 34 | 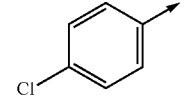 | 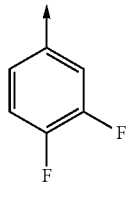 | 459.0 |
| 35 | 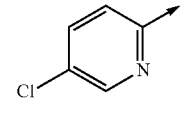 |  | 460.0 |
| 36 | 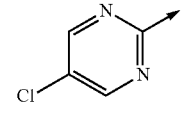 | 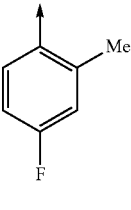 | 461.3 |
| 37 | 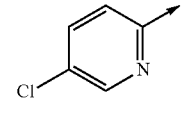 | 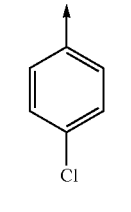 | 456.6 |
| 38 | 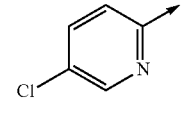 | 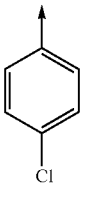 | 457.9 |
TABLE 4-continued
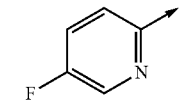
| Example | R₂ | R₃ | LCMS: found m/e (M + H) |
|---|---|---|---|
| 39 | 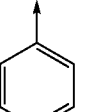 | 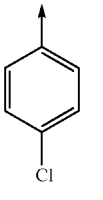 | 442.0 |
| 40 | 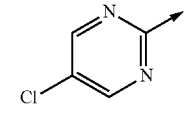 | 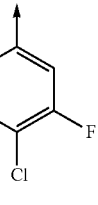 | 459.0 |
| 41 | 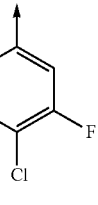 | 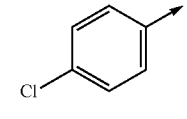 | 475.0 |
| 42 | 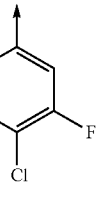 | 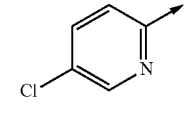 | 476.0 |
| 43 | 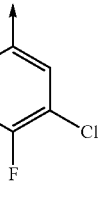 | 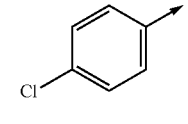 | 475.0 |
| 44 | 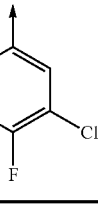 | 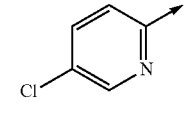 | 476.0 |

Example 45

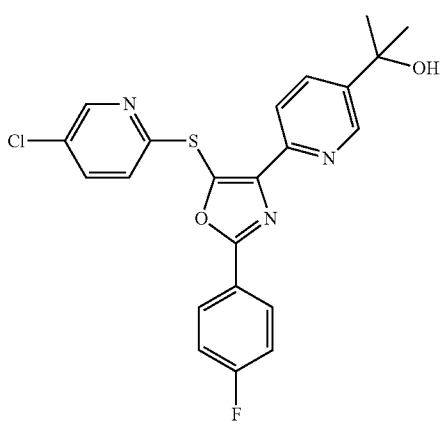

2-{6-[5-[(5-Chloropyridin-2-yl)thio]-2-(4-fluorophenyl)-1,3-oxazol-4-yl]pyridin-3-yl}propan-2-ol The title compound was prepared following the procedure described for Example 12, substituting 2-(5-bromopyridin-2-yl)propan-2-ol with 2-(6-bromopyridin-3-yl)propan-2-ol. The oil was purified on silica gel to afford the title compound (74 mg). LC/MS: m/e 442.0 (M+H)+. 1H NMR (500 MHz, Acetone-d6): δ 1.59 (s, 6H), 4.42 (s, 1H), 7.36 (m, 3H), 7.75 (dd, J=2.6, 8.6 Hz, 1H), 8.06 (m, 2H), 8.21 (m, 2H), 8.43 (d, J=2.5 Hz, 1H), 8.77 (s, 1H).

The compounds in Table 5 were prepared from the appropriate starting materials using the procedure for Example 45.

TABLE 5

| Example | R2 | R3 | LCMS: found m/e (M + H) |
|---|---|---|---|
| 46 | 4-fluorophenyl | 4-chlorophenyl | 441.0 |

Example 47

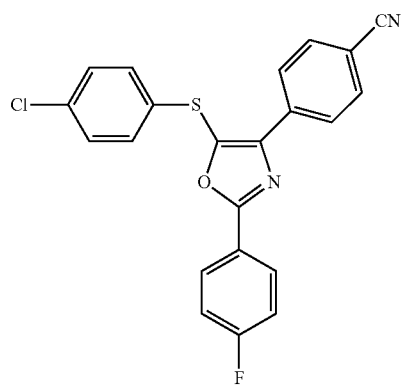 [SMILES: N#Cc1ccc(-c2nc(-c3ccc(F)cc3)oc2Sc2ccc(Cl)cc2)cc1]

4-[5-[(4-Chlorophenyl)thio]-2-(4-fluorophenyl)-1,3-oxazol-4-yl]benzonitrile

A solution of 4-chlorobenzenethiol (389 mg, 2.70 mmol) dissolved in 5 mL of NMP was treated with NaH (108 mg, 2.70 mmol). The resulting solution was stirred for 30 min at rt before Intermediate 14 (700 mg, 1.80 mmol) and CuI (342 mg, 1.80 mmol) were added to the solution. The resulting dark solution was heated to 120° C. for 2 h. After which point, the solution was poured into a rapidly stirred solution of 9:1 NH4Cl:NH4OH and EtOAc. Upon clarification of the organic layer, removal of the organic layer was followed by drying over MgSO4, filtration and concentration giving rise to an oil. The oil was purified on silica gel to afford the title compound. LC/MS: m/e 407.8 (M+H)+.

Example 48

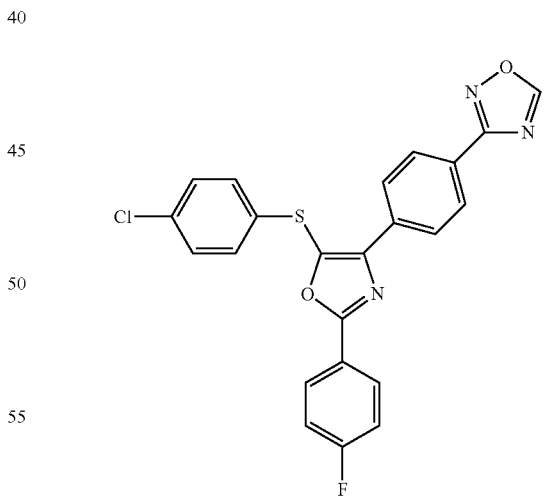

3-{4-[5-[(4-Chlorophenyl)thio]-2-(4-fluorophenyl)-1,3-oxazol-4-yl]phenyl}-1,2,4-oxadiazole To Example 47 (100 mg, 0.25 mmol) in 10 mL EtOH was added 1.0 mL of 50 wt % aqueous NH2OH and 15 mg of K2CO3. The reaction was heated to 120° C. for 5 min via microwave irradiation. The reaction mixture was concentrated to dryness and the residue was dissolved in 5 mL triethylorthoformate, 10 mL EtOH and 1 mL of TFA. The reaction was heated to 100° C. for 10 min via microwave irradiation. The volatiles were removed and the residue was purified on silica gel to afford the title compound (111 mg). LC/MS: m/e 450.0 (M+H)⁺. ¹H NMR (500 MHz, Acetone-d6): δ 7.37-7.41 (m, 6H), 8.21 (m, 4H), 8.40 (m, 2H), 9.41 (s, 1H).

Example 49

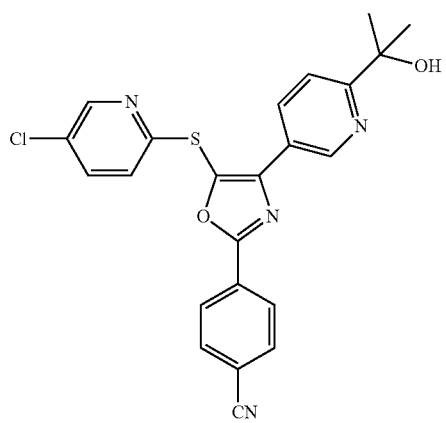 [SMILES: CC(C)(O)c1ccc(-c2nc(-c3ccc(C#N)cc3)oc2Sc2ccc(Cl)cn2)cn1]

4-{5-[(5-Chloropyridin-2-yl)thio]-4-[6-(1-hydroxy-1-methylethyl)pyridin-3-yl]-1,3-oxazol-2-yl}benzonitrile The title compound was prepared following the procedure described for Example 12 using Intermediate 17 (42 mg, 0.10 mmol) and 5-chloropyridine-2-thiol (35.0 mg, 0.24 mmol). The oil was purified on silica gel to afford the title compound (44.6 mg). LC/MS: m/e 449.0 (M+H)⁺. ¹H NMR (500 MHz, Acetone-d6): δ 1.53 (s, 6H), 4.61 (s, 1H), 7.44 (d, J=8.7 Hz, 1H), 7.80 (m, 2H), 8.03 (d, J=8.5 Hz, 2H), 8.36 (d, J=8.5 Hz, 2H), 8.43 (d, J=2.5 Hz, 1H), 8.45 (t, J=2.5 Hz, 1H), 9.20 (d, J=2.1 Hz, 1H).

Example 50

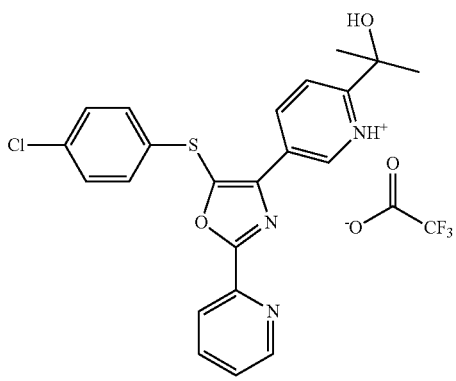

2-(5-{5-[(4-chlorophenyl)thio]-2-pyridin-2-yl-1,3-oxazol-4-yl}pyridin-2-yl)propan-2-ol, trifluoroacetic acid salt

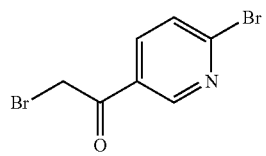 [SMILES: O=C(CBr)c1ccc(Br)nc1]

2-bromo-1-(6-bromopyridin-3-yl)ethanone

Step A

To a solution of 1-(6-bromo-pyridin-3-yl)-ethanone (20.3 g, 101 mmol) and aluminum chloride (200 mg, 1.5 mmol) in chloroform (288 mL) was added bromine (5.23 mL, 101 mmol). The mixture was stirred at rt for 16 h. Upon completion of the reaction as judged by LC/MS analysis, the solution was diluted with sat aq NaHCO₃ and extracted with DCM. The organic layer was removed, dried over MgSO₄, filtered and concentrated giving rise to 31 g 2-bromo-1-(6-bromopyridin-3-yl)ethanone, which was taken on immediately. LC/MS: m/e 277.9 (M+H).

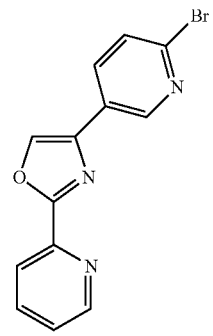 [SMILES: Brc1ccc(-c2coc(-c3ccccn3)n2)cn1]

2-bromo-5-(2-pyridin-2-yl-1,3-oxazole-4-yl)pyridine

Step B

A mixture of 2-bromo-1-(6-bromopyridin-3-yl)ethanone from Step A (2.3 g, 8.25 mmol) and pyridine-2-carboxamide (1 g, 8.25 mmol) was melted at 85°. Heating was continued until the mixture reached 140° at which point the product solidified. Ice, EtOAc and sat aq NaHCO₃ were added. The aqueous layer was then back extracted with EtOAc/THF (3:1).

Pooled organics were dried over MgSO₄, filtered, concentrated, and purified on silica gel to afford 250 mg (10% yield) of 2-bromo-5-(2-pyridin-2-yl-1,3-oxazole-4-yl)pyridine. LC/MS: m/e 302.0 (M+H).

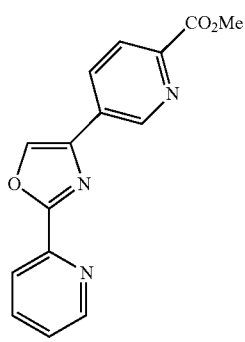 [SMILES: COC(=O)c1ccc(-c2coc(-c3ccccn3)n2)cn1]

methyl 5-(2-pyridin-2-yl-1,3-oxazol-4-yl)pyridine-2-carboxylate

Step C

A mixture of 2-bromo-5-(2-pyridin-2-yl-1,3-oxazole-4-yl)pyridine from Step B (250 mg, 0.827 mmol), dppf (92 mg, 0.166 mmol), Pd(OAc)$_2$ (19 mg, 0.0826 mmol), TEA (0.137 mL, 0.993 mmol) in MeOH (1.4 mL) and DMF (1.4 mL) was bubbled with carbon monoxide for 15 min. The mixture was then placed under a balloon filled with carbon monoxide and stirred at rt for 0.5 h before heating to 75° for 16 h. Upon completion of the reaction as judged by LCMS analysis, the solution was diluted with dist H$_2$O and extracted with EtOAc. The organic layer was removed, dried over MgSO$_4$, filtered through a pad of Celite, concentrated, and purified on silica gel giving rise to 200 mg (86% yield) of methyl 5-(2-pyridin-2-yl-1,3-oxazol-4-yl)pyridine-2-carboxylate. LCMS: m/e 282.1 (M+H).

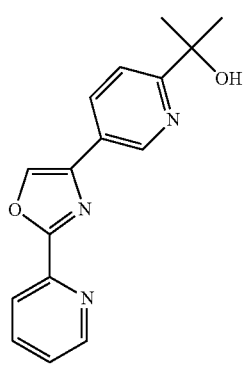 [SMILES: CC(C)(O)c1ccc(-c2coc(-c3ccccn3)n2)cn1]

2-[5-(2-pyridin-2-yl-1,3-oxazol-4-yl)pyridin-2-yl]propan-2-ol

Step D

To a solution of methyl 5-(2-pyridin-2-yl-1,3-oxazol-4-yl)pyridine-2-carboxylate from Step C. (75 mg, 0.267 mmol) in THF (1 mL) at 0° was added a 3 M solution of methylmagnesium bromide in diethyl ether (0.533 mL, 1.6 mmol). The ice bath was removed and the reaction mixture was stirred for 1 h under an atmosphere of nitrogen. Upon completion of the reaction as judged by LCMS analysis, the solution was diluted with sat aq NH$_4$Cl and extracted with EtOAc. The organic layer was removed, dried over MgSO$_4$, filtered and concentrated giving rise to 2-[5-(2-pyridin-2-yl-1,3-oxazol-4-yl)pyridin-2-yl]propan-2-ol, which was taken on immediately. LC/MS: m/e 282.1 (M+H).

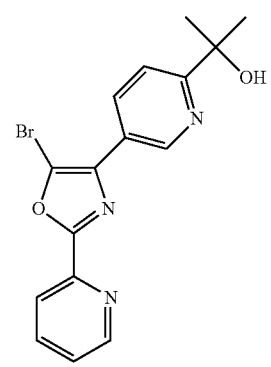 [SMILES: CC(C)(O)c1ccc(-c2nc(-c3ccccn3)oc2Br)cn1]

2-[5-(5-bromo-2-pyridin-2-yl-1,3-oxazol-4-yl)pyridin-2-yl]propan-2-ol

Step E

To a solution of 2-[5-(2-pyridin-2-yl-1,3-oxazol-4-yl)pyridin-2-yl]propan-2-ol from Step D (75 mg, 0.267 mmol) in DCM (1 mL) was added NBS (62 mg, 0.347 mmol). The reaction mixture was stirred at rt for 16 h. Water was added and the mixture extracted with DCM. The organics were dried (MgSO$_4$), and concentrated to afford 2-[5-(5-bromo-2-pyridin-2-yl-1,3-oxazol-4-yl)pyridin-2-yl]propan-2-ol, which was used without further purification LCMS: m/z 360.0 (M+H)$^+$.

Step F

To a solution of 4-chloro thiophenol (38 mg, 0.264 mmol) in NMP (0.5 mL) was added NaH (11 mg, 0.264 mmol) and stirred at rt for 0.5 h under an atmosphere of nitrogen. To the resulting sodium salt was added a solution of 2-[5-(5-bromo-2-pyridin-2-yl-1,3-oxazol-4-yl)pyridin-2-yl]propan-2-ol from Step E (38 mg, 0.105 mmol) in NMP (0.5 mL) followed by CuI (20 mg, 0.105 mmol). The mixture was then heated at 120° for 2 h under an atmosphere of nitrogen. Saturated aqueous ammonium chloride (4.5 mL) and ammonium hydroxide (0.5 mL) were added and the mixture stirred at rt for 0.5 h. The mixture was extracted 3 times with EtOAc. Combined organics were dried (MgSO$_4$), concentrated, and purified by reverse phase HPLC to afford 20 mg (35% yield over 3 steps) of the title compound as the TFA salt. LCMS: m/z 424.1 (M+H)$^+$. $^1$H NMR (500 MHz, CO(CD$_3$)$_2$: δ 9.25

(1H, s), 8.75 (1H, m), 8.50 (1H, m), 8.32 (1H, d), 8.06 (1H, m), 7.82 (1H, m), 7.60 (1H, m), 7.43 (4H, br), 1.55 (6H, s).

Example 51

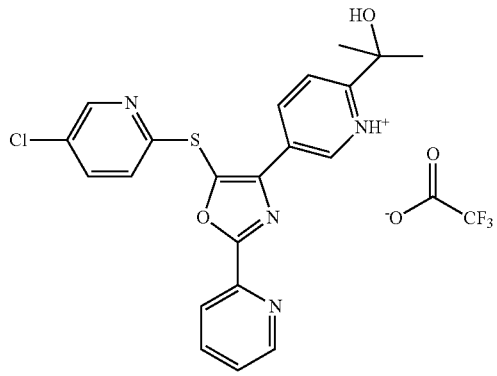

2-(5-{5-[(5-chloropyridin-2-yl)thio]-2-pyridin-2-yl-1,3-oxazol-4-yl}pyridin-2-yl)propan-2-ol, trifluoroacetic acid salt To a solution of 5-chloropyridine-2-thiol (38 mg, 0.264 mmol) in NMP (0.5 mL) was added NaH (11 mg, 0.264 mmol) and stirred at rt for 0.5 h under an atmosphere of nitrogen. To the resulting sodium salt was added a solution of 2-[5-(5-bromo-2-pyridin-2-yl-1,3-oxazol-4-yl)pyridin-2-yl]propan-2-ol (38 mg, 0.105 mmol) in NMP (0.5 mL) followed by CuI (20 mg, 0.105 mmol). The mixture was then heated at 120° for 2 h under an atmosphere of nitrogen. Saturated aqueous ammonium chloride (4.5 mL) and ammonium hydroxide (0.5 mL) were added and the mixture stirred at rt for 0.5 h. The mixture was extracted 3 times with EtOAc. Combined organics were dried (MgSO$_4$), concentrated, and purified by reverse phase HPLC to afford 18 mg (32% yield over 3 steps) the title compound as the TFA salt. LCMS: m/z 425.1 (M+H)$^+$. $^1$H NMR (500 MHz, CO(CD$_3$)$_2$: δ 9.22 (1H, s), 8.77 (1H, s), 8.55 (2H, br), 8.34 (1H, m), 8.07 (1H, m), 7.81 (2H, br), 7.61 (1H, m), 7.42 (1H, d) 1.54 (6H, s).

Example 52

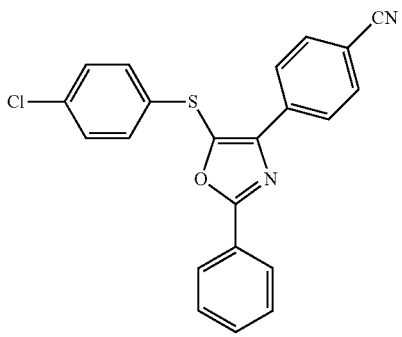 [SMILES: N#Cc1ccc(-c2nc(-c3ccccc3)oc2Sc2ccc(Cl)cc2)cc1]

5-[(4-chlorophenyl)-thio]-4-(4-cyanophenyl)-2-phenyl-1,3-oxazole

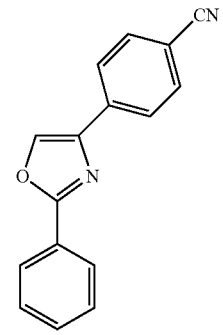 [SMILES: N#Cc1ccc(-c2coc(-c3ccccc3)n2)cc1]

4-(2-phenyl-1,3-oxazol-4-yl)benzonitrile

Step A

The mixture of the 2-bromo-1-(4-cyanophenyl)ethanone (4 g, 17.85 mmol) and benzamide (5.41 g, 44.6 mmol) was heated to 135° C. for 3 hours. Then the reaction mixture was cooled, and partitioned between diethyl ether and water. The aqueous layer was extracted with ether twice, and the combined organic layers were washed with 1N NaOH, 1N HCl, water, and brine, dried over MgSO$_4$. After concentration, the solid residue was dissolved in CHCl3. The insoluable solid was filtered through a frits funnel and discarded. The CHCl3 solution was filtered through a pad of silica and evaporate to dryness to give 2.9 g (66% yield) of 4-(2-phenyl-1,3-oxazol-4-yl)benzonitrile. LCMS: m/z 247.1 (M+H)$^+$.

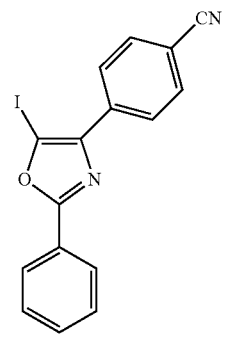 [SMILES: N#Cc1ccc(-c2nc(-c3ccccc3)oc2I)cc1]

4-(5-iodo-2-phenyl-1,3-oxazol-4-yl)benzonitrile

Step B

The product of Step A (140 mg, 0.57 mmol) was dissolved in 2 mL of chloroform, to which was added NIS (282 mg, 1.35 mmol) and 2 drops of TFA. After stirring at rt for two days, the reaction was diluted with dichloromethane, washed with aq NaHCO$_3$, aq Na$_2$S$_2$O$_3$, water, and brine. The organic layer was dried over MgSO$_4$, filtered, and concentrated to give 186 mg (88% yield) of 4-(5-iodo-2-phenyl-1,3-oxazol-4-yl)benzonitrile. LCMS: m/z 373.0 (M+H)$^+$.

Step C

CuI (4.8 mg, 0.025 mmol), K$_2$CO$_3$ (138 mg, 1 mmol), the product of Step B (186 mg, 0.5 mmol), and 4-chlorobenzenethiol (72 mg, 0.5 mmol) were added to a flask, which was evacuated and backfilled with N$_2$ (3 cycles). 2-Propanol (2 mL) and ethylene glycol (0.056 mL, 1 mmol) were added by syringe at rt. The reaction mixture was heated at 80° C. for 18 hours. Then the reaction was diluted with EtOAc, filtered, concentrated, and the residue was subject to silica column (0-20% EtOAc in hexanes) to give the title compound. 1H NMR (500 MHz, (CDCl$_3$): 8.38 (d, 2H), 8.19 (d, 2H), 7.78 (d, 2H), 7.57 (m, 3H), 7.31 (d, 2H), 7.25 (d, 2H). LCMS: m/z 389.0 (M+H)$^+$.

Example 53

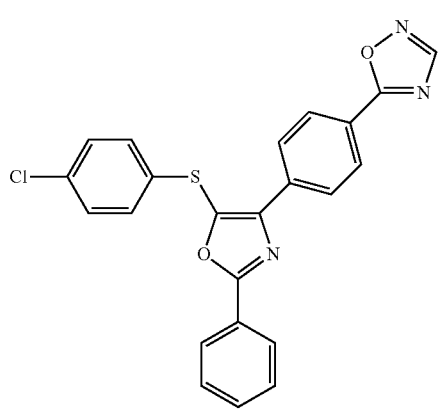 [SMILES: Clc1ccc(Sc2oc(-c3ccccc3)nc2-c2ccc(-c3ncno3)cc2)cc1]

3-(4-{5-[(4-Chlorophenyl)thio]-2-phenyl-1,3oxazol-4-yl}phenyl)-1,2,4oxadiazole

To 3-(4-{5-[(4-chlorophenyl)thio]-2-phenyl-1,3oxazol-4-yl}benzonitrile (30 mg, 0.075 mmol) in 2 mL EtOH was added 0.25 mL of 50% aqueous NH$_2$OH and catalytic amount of K$_2$CO$_3$. The reaction was heated at 120° C. for 1 h via microwave irradiation. The reaction mixture was concentrated to dryness and the residue was dissolved in 5 mL triethylorthoformate. A catalytic amount of TFA was added, and the reaction was heated at 130° C. for 3 h. The volatiles were removed and the residue was purified by reverse phase HPLC to afford 12 mg (37% yield) of the title compound: m/z 432.1 (M+H)$^+$. $^1$H NMR (500 MHz, CDCl$_3$: 8.8 (1H, s), 8.39 (2H, d), 8.21 (2H, d), 8.19 (1H, m), 7.59 (4H, br), 7.24 (4H, br).

Example 54

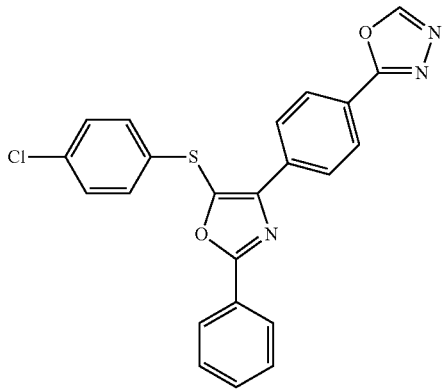 [SMILES: Clc1ccc(Sc2oc(-c3ccccc3)nc2-c2ccc(-c3nnco3)cc2)cc1]

2-(4-{5-[(4-Chlorophenyl)thio]-2-phenyl-1,3oxazol-4-yl}phenyl)-1,3,4oxadiazole

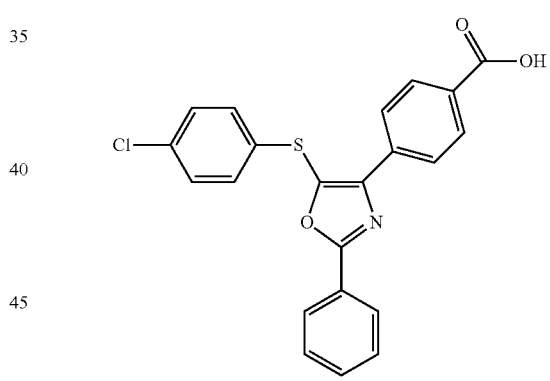

4-{5-[(4-chlorophenyl)thio]-2-phenyl-1,3-oxazol-4-yl}benzoic acid

Step A

A solution of 3-(4-{5-[(4-chlorophenyl)thio]-2-phenyl-1,3oxazol-4-yl}benzonitrile (30 mg, 0.077 mmol) in ethanol (1 mL) and 2N NaOH (1 mL) was heated to reflux for 16 h. EtOAc was added followed by saturated aqueous ammonium chloride. The organics were dried (MgSO$_4$) and concentrated to afford 4-{5-[(4-chlorophenyl)thio]-2-phenyl-1,3-oxazol-4-yl}benzoic acid, which was used with out further purification. LCMS: m/z 407.1 (M+H)$^+$.

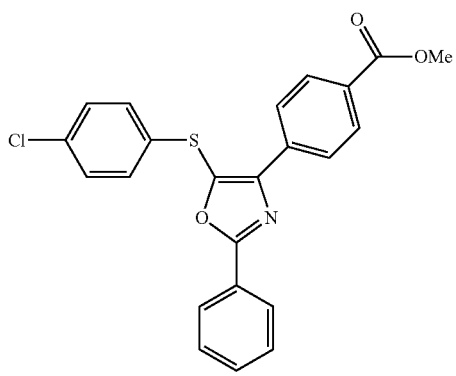 [SMILES: COC(=O)c1ccc(-c2nc(-c3ccccc3)oc2Sc2ccc(Cl)cc2)cc1]

methyl 4-{5-[(4-chlorophenyl)thio]-2-phenyl-1,3-oxazol-4-yl}benzoate

Step B

4-{5-[(4-chlorophenyl)thio]-2-phenyl-1,3-oxazol-4-yl}benzoic acid from Step A (32 mg, 0.077 mmol) was dissolved in MeOH (0.5 mL) and DCM (0.5 mL). Trimethylsilyl diazomethane (2.0 M in ether) was slowly added at 0° C. until a yellow color persisted. The volatiles were evaporated to give methyl 4-{5-[(4-chlorophenyl)thio]-2-phenyl-1,3-oxazol-4-yl}benzoate which was used without further purification. LCMS: m/z 421.1 (M+H)$^+$.

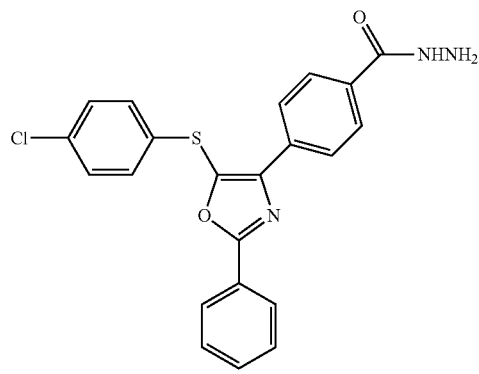 [SMILES: NNC(=O)c1ccc(-c2nc(-c3ccccc3)oc2Sc2ccc(Cl)cc2)cc1]

4-{5-[(4-chlorophenyl)thio]-2-phenyl-1,3-oxazol-4-yl}benzohydrazide

Step C

Methyl 4-{5-[(4-chlorophenyl)thio]-2-phenyl-1,3-oxazol-4-yl}benzoate from Step B (33 mg, 0.077 mmol) was suspended in 1 mL of EtOH and 0.5 mL of anhydrous hydrazine, and heated to reflux for 2 h. EtOAc was added and washed with water 3 times. The organics were dried (MgSO$_4$), and concentrated to afford 4-{5-[(4-chlorophenyl)thio]-2-phenyl-1,3-oxazol-4-yl}benzohydrazide which was used without further purification. LCMS: m/z 421.1 (M+H)$^+$.

Step D

4-{5-[(4-chlorophenyl)thio]-2-phenyl-1,3-oxazol-4-yl}benzohydrazide from Step C (33 mg, 0.077 mmol) was dissolved in 5 mL triethylorthoformate. A catalytic amount of TFA was added and the reaction was heated at 130° C. for 2 h. The volatiles were removed and the residue was purified by reverse phase HPLC to afford 12 mg (36% over 4 steps) of the title compound 2-(4-{5-[(4-chlorophenyl)thio]-2-phenyl-1,3oxazol-4-yl}phenyl)-1,3,4-oxadiazole. LCMS: m/z 432.1 (M+H)$^+$. $^1$H NMR (500 MHz, CDCl$_3$: δ 8.55 (1H, s), 8.40 (2H, d), 8.19 (4H, br), 7.55 (3H, br), 7.30 (4H, br).

Example 55

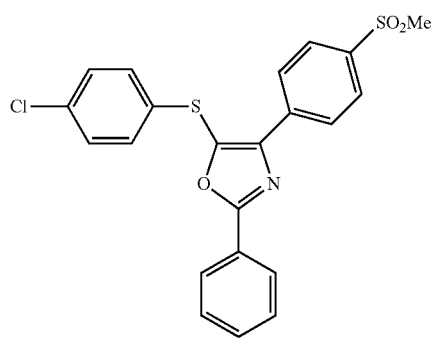 [SMILES: CS(=O)(=O)c1ccc(-c2nc(-c3ccccc3)oc2Sc2ccc(Cl)cc2)cc1]

5-[(4-chlorophenyl)thio]-4-[4-(methylsulfonylphenyl-2-phenyl]-1,3-oxazole

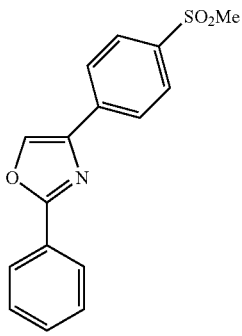 [SMILES: CS(=O)(=O)c1ccc(-c2coc(-c3ccccc3)n2)cc1]

4-[4-(methylsulfonyl)phenyl]-2-phenyl-1,3-oxazole

Step A

The mixture of the 2-bromo-1-[4-(methylsulfonyl)phenyl] ethanone (2 g, 7.2 mmol) and benzamide (0.87 g, 7.2 mmol) was heated to 140~180° C. for 4 hours. When TLC showed that the reaction had completed, the mixture was cooled, and partitioned between EtOAc and water. The aqueous layer was extracted with EtOAc twice, and the combined organic layers were washed with water and brine, dried over MgSO$_4$. After concentration, the residue was purified by column (eluted by PE:EA=10:1) to afford 0.6 g (yield 30%) of 4-[4-(methylsulfonyl)phenyl]-2-phenyl-1,3-oxazole.

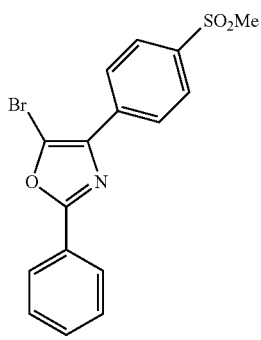 [SMILES: CS(=O)(=O)c1ccc(-c2nc(-c3ccccc3)oc2Br)cc1]

5-bromo-4-[4-(methylsulfonyl)phenyl]-2-phenyl-1,3-oxazole

Step B

To a solution of Step A product (0.7 g, 2.34 mmol) in AcOH (20 ml) and CHCl₃ (30 ml) was added dropwise Br₂ (0.41 g) at rt, and the mixture was stirred for 2 hours. The reaction mixture was poured into water, and extracted with EtOAc three times. The combined organic layers were washed with aqueous NaHCO₃ and brine, dried over Na₂SO₄. After concentration, the residue was purified by column (PE:EA=4:1) to afford 0.7 g (yield 80%) of 5-bromo-4-[4-(methylsulfonyl)phenyl]-2-phenyl-1,3-oxazole.

Step C

To a solution of Step B product (0.2 g, 0.53 mmol) and 4-chlorbenzenethiol (0.076 g, 0.53 mmol) in ethanol was added KOH (34 mg, 0.6 mmol) at rt under N₂, then the mixture was heated to reflux overnight. After cooling, the precipitate was collected by suction, and the filter cake was washed with ethanol. After drying, 200 mg (yield 80%) of the title compound was obtained. ¹H-NMR (400 MHz, DMSO) δ 8.30 (d, 2H, Ar—H), 8.06 (m, 4H, Ar—H), 7.60 (m, 3H, Ar—H), 7.40 (m, 4H, Ar—H), 3.26 (s, 3H, CH₃).

Example 56

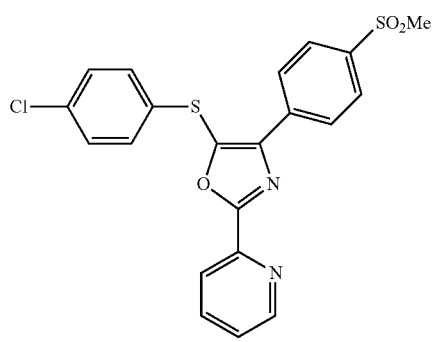 [SMILES: CS(=O)(=O)c1ccc(-c2nc(-c3ccccn3)oc2Sc2ccc(Cl)cc2)cc1]

2-{5-[(4-chlorophenyl)thio]-4-(methylsulfonyl)phenyl]-1,3-oxazol-2-yl}pyridine

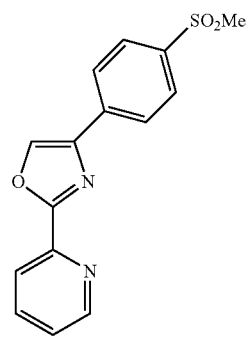 [SMILES: CS(=O)(=O)c1ccc(-c2coc(-c3ccccn3)n2)cc1]

2-{4-[4-(methylsulfonyl)phenyl]-1,3-oxazol-2-yl}pyridin

Step A

The mixture of the 2-bromo-1-[4-(methylsulfonyl)phenyl]ethanone (500 mg, 1.8 mmol) and pyridine 2-carboxamide (551 mg, 4.51 mmol) was heated to 150° C. for 1 hour. Then the reaction mixture was cooled, and partitioned between ethyl acetate and water. The aqueous layer was extracted with ethyl acetate twice, and the combined organic layers were washed with water and brine, dried over MgSO₄. After concentration, the solid residue was dissolved in methanol and subject to mass-directed HPLC purification to give 21 mg of 2-{4-[4-(methylsulfonyl)phenyl]-1,3-oxazol-2-yl}pyridine. LCMS: m/z 301.0 (M+H)⁺.

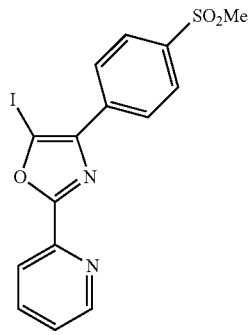 [SMILES: CS(=O)(=O)c1ccc(-c2nc(-c3ccccn3)oc2I)cc1]

2-{5-iodo-4-[4-(methylsulfonyl)phenyl]-1,3-oxazol-2-yl}pyridine

Step B

The product of Step A (20 mg, 0.067 mmol) was dissolved in 1 mL of chloroform, to which was added NIS (22.5 mg, 0.1 mmol) and 1 drop of TFA. After stirring at rt for 2 hours, the reaction was diluted with dichloromethane, washed with aq NaHCO₃, aq Na₂S₂O₃, water, and brine. The organic layer was dried over MgSO₄, filtered, and concentrated to give 2-{5-iodo-4-[4-(methylsulfonyl)phenyl]-1,3-oxazol-2-yl}pyridine. LCMS: m/z 427.0 (M+H)⁺.

Step C

CuI (2 mg, 0.01 mmol), K$_2$CO$_3$ (6.5 mg, 0.05 mmol), the product of Step B (10 mg, 0.023 mmol), and 4-chlorobenzenethiol (3.4 mg, 0.023 mmol) were added to a flask, which was evacuated and backfilled with N$_2$ (3 cycles). 2-Propanol (0.5 mL) and 0.01 mL of ethylene glycol were added by syringe at rt. The reaction mixture was heated at 80° C. for 18 hours. Then the reaction was diluted with acetonitrile and filtered through Celite. The filtrate was subjected to mass-directed HPLC to give the title compound. 1H NMR (500 MHz, (CDCl$_3$): 8.82 (broad s, 1H), 8.47 (d, 2H), 8.23 (d, 1H), 8.05 (d, 2H), 7.91 (t, 1H), 7.46 (t, 1H), 7.23 (AB quartet, 4H), 3.11 (s, 3H). LCMS: m/z 443.0 (M+H)$^+$.

| Example | Human Lysate IC50 (nM) | Human whole cell IC50 (nM) | Rat whole cell IC50 (nM) |
|---|---|---|---|
| Ex 58 | 37 | 112 | 74 |
| Ex 59 | 20 | 67 | 40 |
| Ex 62 | 23 | 41 | 29 |
| Ex 65 | 27 | 29 | 21 |
| Ex 68 | 15 | 100 | 83 |
| Ex 71 | 10 | 30 | 14 |
| Ex 74 | 8 | 37 | 34 |
| Ex 78 | 28 | 69 | 39 |
| Ex 80 | 35 | 67 | 25 |
| Ex 90 | 46 | 1002 | 247 |
| Ex 96 | 17 | 133 | 63 |
| Ex 97 | 20 | NA | 10 |
| Ex 98 | 44 | 222 | 35 |
| Ex 100 | 161 | 337 | 39 |
| Ex 102 | 12 | 35 | 17 |
| Ex 107 | 24 | 91 | 11 |
| Ex 108 | 5 | 20 | 17 |
| Ex 111 | 11 | 64 | 24 |
| Ex 119 | 28 | 47 | 20 |
| Ex 122 | 161 | 474 | 146 |
| Ex 123 | 74 | 510 | 286 |
| Ex 124 | 11 | 98 | 16 |
| Ex 125 | 93 | 2291 | 680 |
| Ex 131 | 140 | 1119 | 782 |

Intermediate 18

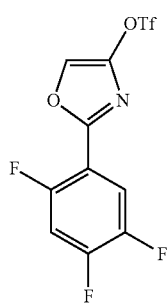 [SMILES: O=S(=O)(Oc1coc(-c2cc(F)c(F)cc2F)n1)C(F)(F)F]

2-(2,4,5-Trifluorophenyl)-1,3-oxazol-4-yl trifluoromethanesulfonate

The title compound was prepared using the procedure described by Langille, N. F.; Dakin, L. A.; Panek, J. S. *Org. Lett.* 2002, 4, 2485.

Intermediate 19

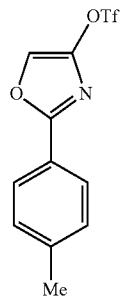 [SMILES: Cc1ccc(-c2nc(OS(=O)(=O)C(F)(F)F)co2)cc1]

2-(4-Methylphenyl)-1,3-oxazol-4-yl trifluoromethanesulfonate

The title compound was prepared using the procedure described by Langille, N. F.; Dakin, L. A.; Panek, J. S. *Org. Lett.* 2002, 4, 2485.

Intermediate 20

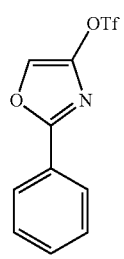 [SMILES: O=S(=O)(Oc1coc(-c2ccccc2)n1)C(F)(F)F]

2-Phenyl-1,3-oxazol-4-yl trifluoromethanesulfonate

The title compound was prepared using the procedure described by Langille, N. F.; Dakin, L. A.; Panek, J. S. *Org. Lett.* 2002, 4, 2485.

Intermediate 21

2-[4-Trifluoromethoxy)phenyl]-1,3-oxazol-4-yltrifluoromethanesulfonate

The title compound was prepared using the procedure described by Langille, N. F.; Dakin, L. A.; Panek, J. S. *Org. Lett.* 2002, 4, 2485.

Intermediate 22

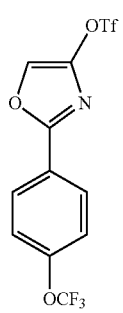

2-(4-Methoxyphenyl-1,3-oxazol-4-yl trifluoromethanesulfonate

The title compound was prepared using the procedure described by Langille, N. F.; Dakin, L. A.; Panek, J. S. *Org. Lett.* 2002, 4, 2485.

Intermediate 23

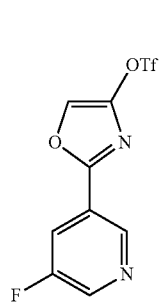

2-(5-Fluoropyridin-3-yl-1,3-oxazol-4-yl trifluoromethanesulfonate

The title compound was prepared using the procedure described by Langille, N. F.; Dakin, L. A.; Panek, J. S. *Org. Lett.* 2002, 4, 2485.

Intermediate 24

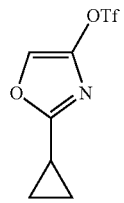 [SMILES: O=S(=O)(Oc1coc(C2CC2)n1)C(F)(F)F]

2-Cyclopropyl-1,3-oxazol-4-yl trifluoromethanesulfonate

The title compound was prepared using the procedure described by Langille, N. F.; Dakin, L. A.; Panek, J. S. *Org. Lett.* 2002, 4, 2485.

Intermediate 25

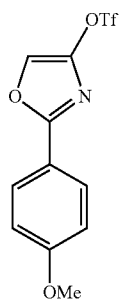

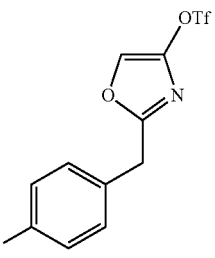

2-(4-Fluorobenzyl)-1,3-oxazol-4-yl trifluoromethanesulfonate

A. To a stirred solution of 4-fluorophenylacetyl chloride (2.0 g, 12.0 mmol) in 25 mL of $CH_2Cl_2$ was added 1.7 g (12.0 mmol) of silver cyanate. The resulting slurry was stirred for 3 h at rt. After which point, the solution was filtered through Celite and the filtrate was then taken on to the next step crude.

B. The acyl isocyanate dissolved in DCM was cooled to 0° C. and treated with TMS Diazomethane (6.9 mL, 14.0 mmol, 2.0 M solution in $Et_2O$). The resulting yellow solution was allowed to warm to rt and stirred for 1 h. Upon completion of the reaction as judged by TLC analysis, the solution was concentrated to dryness and purified on silica gel giving 1.3 g of oxazolidinone intermediate which was taken on directly to triflation.

C. The oxazolidinone (1.3 g, 7 mmol) was treated with $Tf_2O$ (1.7 mL, 10.0 mmol) and TEA (2.0 mL, 14.0 mmol) at −78° C. After 1 h, the solution was diluted with sat aqueous NaCl solution and allowed to warm to rt. The organic layer was removed, dried over $MgSO_4$, filtered and concentrated to dryness giving rise to an oil. The oil was purified on silica gel giving rise to the title compound (768 mg). $^1H$ NMR (500 MHz, Acetone-d6): δ 4.21 (s, 2H), 7.16 (m, 2H), 7.40 (m, 2H), 8.23 (s, 1H).

Intermediate 26

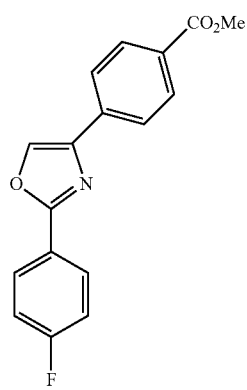 [SMILES: COC(=O)c1ccc(-c2coc(-c3ccc(F)cc3)n2)cc1]

Methyl 4-[2-(4-fluorophenyl)-1,3-oxazol-4-yl]benzoate

A solution of Intermediate 1 (3.09 g, 9.9 mmol), 4-[(methoxycarbonyl)phenyl]boronic acid (2.1 g, 12.0 mmol), Pd(dppf)$Cl_2$, (405 mg, 0.5 mmol), and CsF (3.0 g, 19.9 mmol) were dissolved in dioxane (150 mL) and heated to 100° C. for 12 h. Upon completion of the reaction as judged by TLC analysis, the solution was concentrated to dryness and purified on silica gel to afford the title compound (2.50 g). LC/MS: m/e 395.8 (M+H).

Intermediate 27

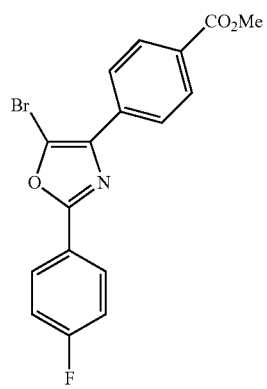

A solution of Intermediate 26 (1.06 g, 3.6 mmol) and NBS (952 mg, 5.4 mmol) in $CH_2Cl_2$ (50 mL) was stirred at rt for 12 h. Upon completion of the reaction, the solution was diluted with sat aq $NaS_2O_3$ solution. The organic layer was removed, dried over $MgSO_4$, filtered and concentrated giving rise to an oil. The oil was purified on silica gel to afford the title compound (1.01 g). LC/MS: m/e 375.8 (M+H)$^+$.

Intermediate 28

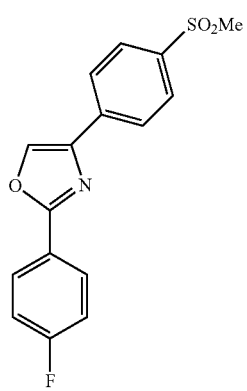

61

2-(4-Fluorophenyl)-4-[4-(methylsulfonyl)phenyl]-1,3-oxazole

The target compound was prepared in an analogous manner to Intermediate 26 except that Intermediate 1 was coupled with [4-(methylsulfonyl)phenyl]boronic acid. LC/MS: m/e 318.1 (M+H).

Intermediate 29

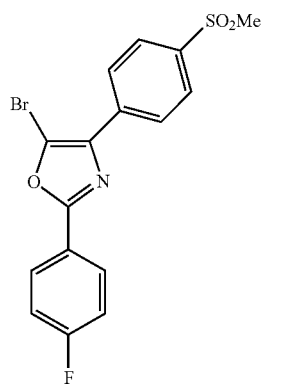 [SMILES: COC(=O)c1ccc(-c2nc(-c3ccc(F)cc3)oc2Br)cc1]

5-Bromo-2-(4-Fluorophenyl)-4-[4-(methylsulfonyl)phenyl]-1,3-oxazole

The target compound was prepared in an analogous manner to Intermediate 27. LC/MS: m/e 395.9 (M+H)$^+$.

Intermediate 30

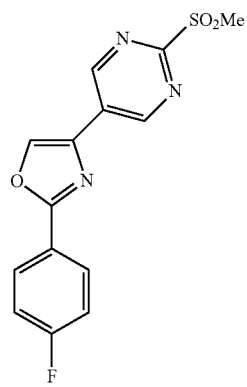 [SMILES: CS(=O)(=O)c1ncc(-c2coc(-c3ccc(F)cc3)n2)cn1]

62

5-[2-(4-Fluorophenyl)-1,3-oxazol-4-yl]pyrimidine-2-carbonitrile

The target compound was prepared in an analogous manner to Intermediate 11 except that Intermediate 1 was coupled with 5-bromopyrimidine-2-carbonitrile. LC/MS: m/e 267.0 (M+H)$^+$.

Intermediate 31

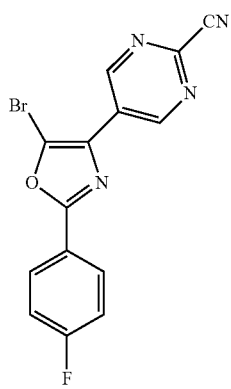 [SMILES: N#Cc1ncc(-c2nc(-c3ccc(F)cc3)oc2Br)cn1]

5-[5-Bromo-2-(4-fluorophenyl)-1,3-oxazol-4-yl]pyrimidine-2-carbonitrile

The target compound was prepared in an analogous manner to Intermediate 27. LC/MS: m/e 345.0 (M+H)$^+$.

Intermediate 32

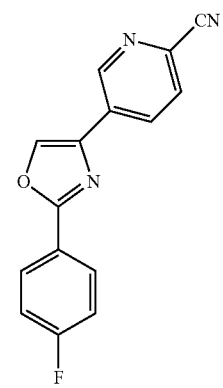 [SMILES: N#Cc1ccc(-c2coc(-c3ccc(F)cc3)n2)cn1]

5-[2-(4-Fluorophenyl)-1,3-oxazol-4-yl]pyridine-2-carbonitrile

The target compound was prepared in an analogous manner to Intermediate 11 except that Intermediate 1 was coupled with 5-bromopyridine-2-carbonitrile. LC/MS: m/e 266.0 (M+H).

Intermediate 33

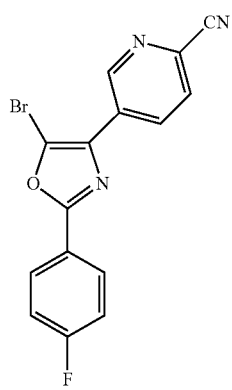 [SMILES: N#Cc1ccc(-c2nc(-c3ccc(F)cc3)oc2Br)cn1]

5-[5-Bromo-2-(4-fluorophenyl)-1,3-oxazol-4-yl]pyridine-2-carbonitrile

The target compound was prepared in an analogous manner to Intermediate 27. LC/MS: m/e 343.9 (M+H)$^+$.

Intermediate 34

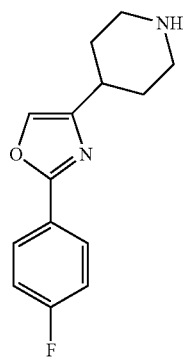 [SMILES: Fc1ccc(-c2nc(C3CCNCC3)co2)cc1]

4-[2-(4-Fluorophenyl)-1,3-oxazol-4-yl]piperidine

A solution of 4-fluorobenzamide (4.54 g, 32.7 mmol) and t-butyl 4-(bromoacetyl)-piperidine-1-carboxylate (5.0 g, 16.3 mmol) in DMF (40 mL) was heated at 145° C. for 16 h. Upon completion of the reaction, the solution was allowed to cool to rt and concentrated to a dark oil. The oil was purified by reverse phase HPLC to afford the title compound (760 mg). LC/MS: m/e 247.08 (M+H)$^+$.

Intermediate 35

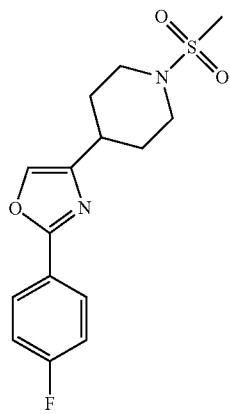 [SMILES: CS(=O)(=O)N1CCC(c2coc(-c3ccc(F)cc3)n2)CC1]

4-[2-(4-Fluorophenyl)-1,3-oxazol-4-yl]-1-(methylsulfonyl)piperidine

To a solution of 4-[2-(4-fluorophenyl)-1,3-oxazol-4-yl]piperidine (220 mg, 0.90 mmol) in DCM (20 mL) was treated with DIEA (0.31 mL, 1.8 mmol) and allowed to stir at rt for 15 min. Methanesulfonyl chloride (0.2 mL, 2.7 mmol) was slowly added to the solution and the resulting mixture was stirred at rt for 2 hr. Upon completion of the reaction, DCM (20 mL) and water (40 mL) was added to the mixture and the two layers were partitioned. The organic layer was dried with MgSO$_4$, filtered and concentrated. The residue was purified by reverse phase HPLC to afford the title compound (100 mg). LC/MS: m/e 325.2 (M+H)$^+$.

Intermediate 36

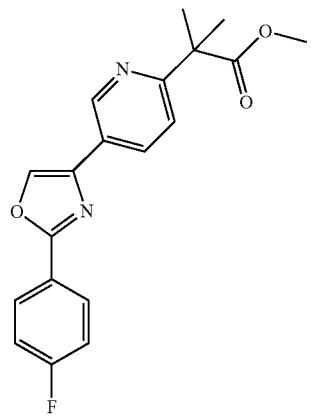 [SMILES: COC(=O)C(C)(C)c1ccc(-c2coc(-c3ccc(F)cc3)n2)cn1]

Methyl 2-{5-[2-(4-fluorophenyl)-1,3-oxazol-4-yl]pyridin-2-yl}-2-methylpropanoate The target compound was prepared in an analogous manner to Intermediate 11 except that Intermediate 1 was coupled with methyl 2-(5-bromopyridin-2-yl)-2-methylpropanoate (Kodanko, J. J.; Morys, A. J.; Lippard, S. J. *Org. Lett.* 2005, 7, 4585) LC/MS: m/e 295.4 (M+H)⁺.

Intermediate 37

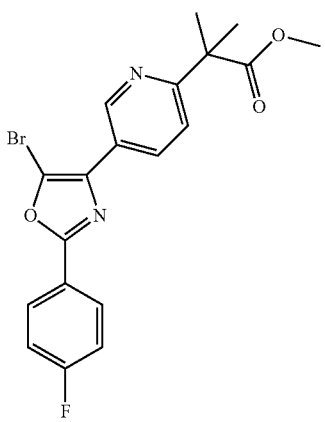 [SMILES: COC(=O)C(C)(C)c1ccc(-c2nc(-c3ccc(F)cc3)oc2Br)cn1]

Methyl 2-{5-[5-bromo-2-(4-fluorophenyl)-1,3-oxazol-4-yl]pyridin-2-yl}-2-methyl propanoate The target compound was prepared in an analogous manner to Intermediate 27. LC/MS: m/e 373.05 (M+H)⁺.

Intermediate 38

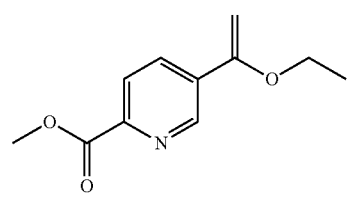

Methyl 5-(1-ethoxyethenyl)pyridine-2-carboxylate

To a solution of methyl 5-bromopyridine-2-carboxylate (25 g, 116 mmol) in dioxane (30 mL) was added Pd(PPh₃)₄ (6.7 g, 5.8 mmol) and tributyl(1-ethoxyvinyl)tin (46 g, 127.0 mmol). The resulting solution was heated to reflux under N₂ for 12 h. Upon completion of the reaction as judged by LC/MS analysis, the reaction was diluted with EtOAc, washed with KF solution (10% aqueous), filtered through Celite, dried over MgSO₄, filtered, concentrated and purified on silica gel to afford the title compound (20.4 g). LC/MS: m/e 208.1 (M+H)⁺.

Intermediate 39

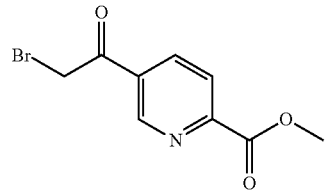

Methyl 5-(bromoacetyl)pyridine-2-carboxylate

To a solution of Intermediate 38 (20.3 g, 98.0 mmol) in THF/H₂O (700 mL/46 mL) at rt was added NBS (15.0 g, 98.0 mmol) in one portion, The resulting solution was stirred at rt for 30 min. Upon completion of the reaction as judged by LC/MS analysis, the reaction was concentrated to dryness and purified on silica gel to afford the title compound (19.5 g). LC/MS: m/e 259.9 (M+H)⁺.

Intermediate 40

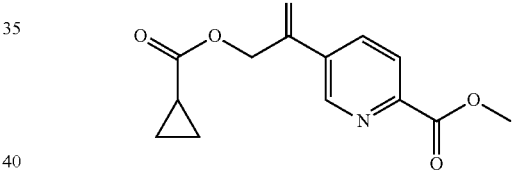

Methyl 5-{[(cyclopropylcarbonyl)oxy]acetyl}pyridine-2-carboxylate

The mixture of cyclopropyl carboxylic acid (5.0 g, 58.1 mmol), Intermediate 39 (15.0 g, 58.1 mmol) and K₂CO₃ (9.63 g, 69.7 mmol) in DMF (50 mL) was stirred at rt for 12 h. Upon completion of the reaction as judged by LC/MS analysis, the reaction was diluted with H₂O and the resulting precipitate was filtered to afford the title compound (8.54 g). LC/MS: m/e 263.9 (M+H)⁺.

Intermediate 41

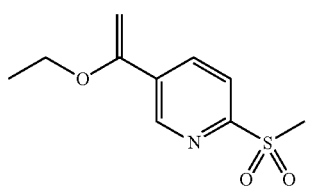

5-(1-Ethoxyethenyl)-2-(methylsulfonyl)pyridine

The target compound was prepared in an analogous manner to Intermediate 38 except starting with 5-bromo-2-methylsulphonylpyridine. LC/MS: m/e 228.05 (M+H)⁺.

Intermediate 42

2-Bromo-1-[6-(methylsulfonyl)pyridin-3-yl]ethanone

The title compound was prepared in an analogous manner to Intermediate 39. LC/MS: m/e 279.76 (M+H)⁺.

Intermediate 43

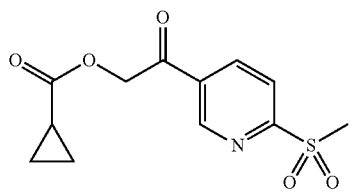 [SMILES: CS(=O)(=O)c1ccc(C(=O)COC(=O)C2CC2)cn1]

2-[6-(Methylsulfonyl)pyridin-3-yl]-2-oxoethyl cyclopropanecarboxylate

The title compound was prepared in an analogous manner to Intermediate 40. LC/MS: m/e 283.9 (M+H)⁺.

Intermediate 44

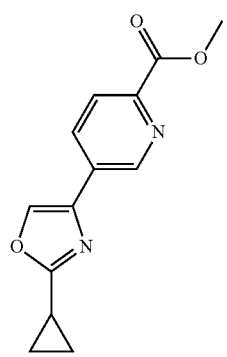 [SMILES: COC(=O)c1ccc(-c2coc(C3CC3)n2)cn1]

Methyl 5-(2-cyclopropyl-1,3-oxazol-4-yl)pyridine-2-carboxylate

To a solution of Intermediate 40 (2.0 g, 7.6 mmol) in p-xylene (130 mL) was added acetamide (2.24 g, 38.0 mmol) and BF₃.OEt₂ (1.9 mL, 15.2 mmol). The resulting solution was heated at reflux for 72 h. After which point, the reaction was diluted with sat. NaHCO₃ solution, and extracted with EtOAc. The organic layer was washed with brine, dried over MgSO₄, filtered, concentrated and purified on silica gel to afford the title compound (862 mg). LC/MS: m/e 245.0 (M+H)⁺.

Intermediate 45

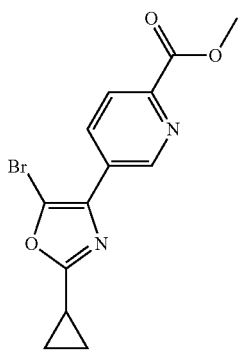 [SMILES: COC(=O)c1ccc(-c2nc(C3CC3)oc2Br)cn1]

Methyl 5-(5-bromo-2-cyclopropyl-1,3-oxazol-4-yl)pyridine-2-carboxylate

The target compound was prepared in an analogous manner to Intermediate 27 starting with Intermediate 44. LC/MS: m/e 324.8 (M+H)⁺.

Intermediate 46

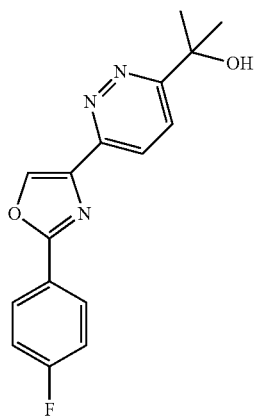 [SMILES: CC(C)(O)c1ccc(-c2coc(-c3ccc(F)cc3)n2)nn1]

2-{6-[2-(4-Fluorophenyl)-1,3-oxazol-4-yl]pyridazin-3-yl}propan-2-ol

The target compound was prepared in an analogous manner to Intermediate 11 except that intermediate 1 was coupled with 2-(6-chloropyridazin-3-yl)propan-2-ol. LC/MS: m/e 380.0 (M+H)⁺.

Intermediate 47

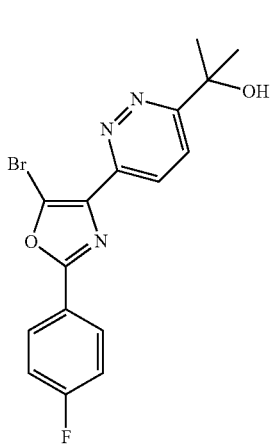 [SMILES: CC(C)(O)c1ccc(-c2nc(-c3ccc(F)cc3)oc2Br)nn1]

2-{6-[5-Bromo-2-(4-fluorophenyl)-1,3-oxazol-4-yl]pyridazin-3-yl}propan-2-ol

The target compound was prepared in an analogous manner to Intermediate 27. LC/MS: m/e 380.0 (M+H)⁺.

Intermediate 48

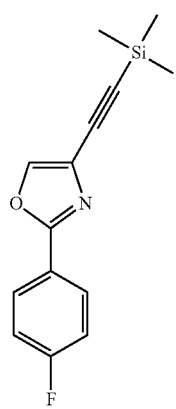 [SMILES: C[Si](C)(C)C#Cc1coc(-c2ccc(F)cc2)n1]

2-(4-Fluorophenyl)-4-[(trimethylsilyl)ethynyl]-1,3-oxazole

To a solution of Intermediate 1 (2.1 g, 6.8 mmol) in DMF (5 mL) was added TMS acetylene (1.9 mL, 13.6 mmol), Pd(PPh$_3$)Cl$_2$ (49 mg, 0.07 mmol), CuI (26 mg, 0.14 mmol), LiCl (433 mg, 10.2 mmol) and Diethylamine (9.2 mL, 89 mmol). The resulting solution was heated in the microwave reactor for 5 min at 120° C. After which point, the reaction was diluted with sat. NH$_4$Cl solution, and extracted with EtOAc. The organic layer was washed with brine, dried over MgSO$_4$, filtered, concentrated and purified on silica gel to afford the title compound (1.40 g). LC/MS: m/e 262.1 (M+H)⁺.

Intermediate 49

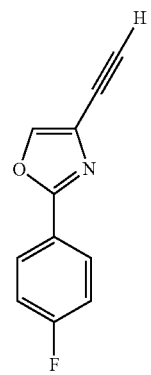 [SMILES: C#Cc1coc(-c2ccc(F)cc2)n1]

4-Ethynyl-2-(4-fluorophenyl)-1,3-oxazole

To a solution of Intermediate 48 (1.4 g, 5.4 mmol) in MeOH (25 mL) was added K$_2$CO$_3$ (746 mg, 5.4 mmol). The resulting solution was heated allowed to stir for 12 h. After which point, the solution was diluted with H$_2$O and Et$_2$O. The organic layer was dried over MgSO$_4$, filtered, concentrated to afford the title compound (1.01 g). LC/MS: m/e 188.1 (M+H)⁺.

Intermediate 50

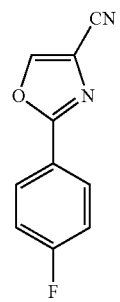 [SMILES: N#Cc1coc(-c2ccc(F)cc2)n1]

2-(4-Fluorophenyl)-1,3-oxazole-4-carbonitrile

To a solution of Intermediate 1 (2.1 g, 6.8 mmol) in DMF (15 mL) was added Pd(PPh$_3$)$_4$ (787 mg, 0.68 mmol), and Zn(CN)$_2$ (1.20 g, 10.2 mmol). The resulting solution was heated in a microwave reactor for 15 min at 120° C. After which point, the reaction was diluted with sat. NH$_4$C solution, and extracted with EtOAc. The organic layer was washed with brine, dried over MgSO₄, filtered, concentrated and purified on silica gel to afford the title compound (260 mg). LC/MS: m/e 189.2 (M+H)⁺.

Intermediate 51

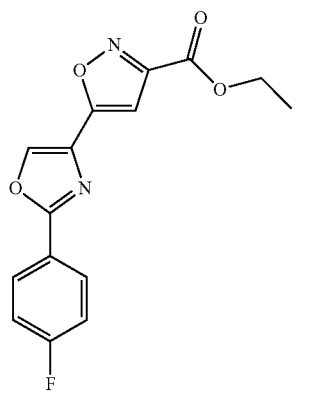 [SMILES: CCOC(=O)c1cc(-c2coc(-c3ccc(F)cc3)n2)on1]

Ethyl 5-[2-(4-fluorophenyl)-1,3-oxazol-4-yl]isoxazole-3-carboxylate

To a stirred solution of Intermediate 49 (1.1 g, 5.9 mmol) in THF/DCM 1:1 (40 mL) was added ethyl (2Z)-chloro(hydroxyimino)ethanoate (1.3 g, 8.8 mmol) and TEA (2.4 mL, 17.6 mmol). The resulting solution was stirred for 48 h at rt. After which point, the solution was concentrated and purified on silica gel to afford the title compound (469 mg). LC/MS: m/e 303.0 (M+H)⁺.

Intermediate 52

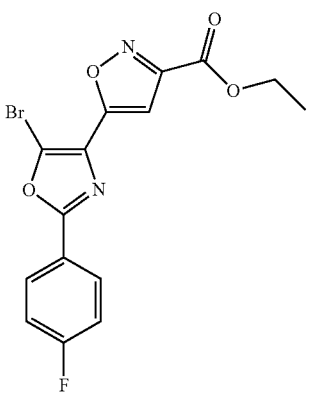 [SMILES: CCOC(=O)c1cc(-c2nc(-c3ccc(F)cc3)oc2Br)on1]

Ethyl 5-[5-bromo-2-(4-fluorophenyl)-1,3-oxazol-4-yl]isoxazole-3-carboxylate

The target compound was prepared in an analogous manner to Intermediate 27 starting with Intermediate 51. LC/MS: m/e 382.9 (M+H)⁺

Intermediate 53

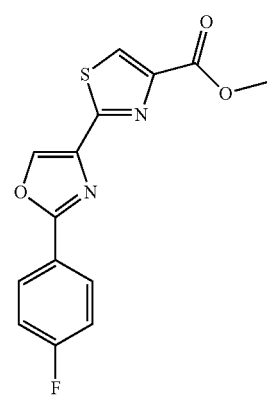 [SMILES: COC(=O)c1csc(-c2coc(-c3ccc(F)cc3)n2)n1]

Methyl 2-[2-(4-fluorophenyl)-1,3-oxazol-4-yl]-1,3-thiazole-4-carboxylate

The target compound was prepared in an analogous manner to Intermediate 11 except that Intermediate 1 was coupled with methyl 2-bromothiazole-4-carboxylate. LC/MS: m/e 304.9 (M+H)⁺.

Intermediate 54

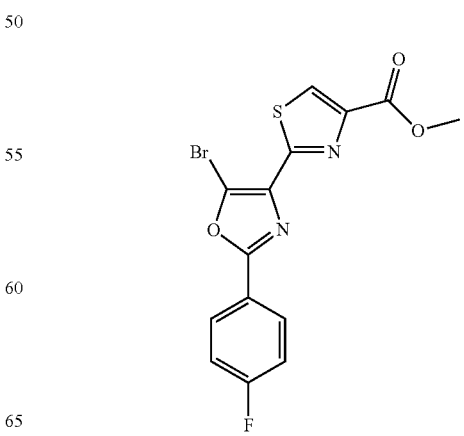

73

Methyl 2-[5-bromo-2-(4-fluorophenyl)-1,3-oxazol-4-yl]-1,3-thiazole-4-carboxylate The target compound was prepared in an analogous manner to Intermediate 27 starting with Intermediate 53. LC/MS: m/e 384.9 (M+H)+.

Intermediate 55

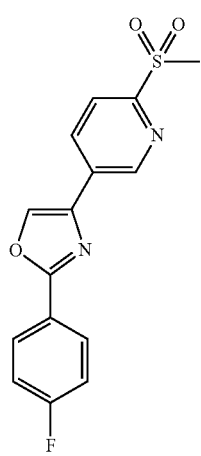 [SMILES: CS(=O)(=O)c1ccc(-c2coc(-c3ccc(F)cc3)n2)cn1]

5-[2-(4-Fluorophenyl)-1,3-oxazol-4-yl]-2-(methylsulfonyl)pyridine

The target compound was prepared in an analogous manner to Intermediate 11 except that Intermediate 1 was coupled with 2-bromo-5-methylsulphonylpyridine. LC/MS: m/e 318.9 (M+H)+

Intermediate 56

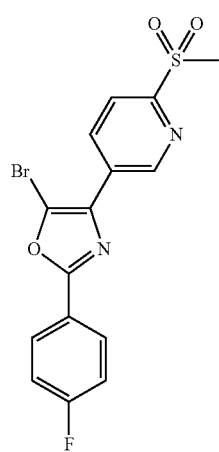 [SMILES: CS(=O)(=O)c1ccc(-c2nc(-c3ccc(F)cc3)oc2Br)cn1]

74

5-[5-Bromo-2-(4-fluorophenyl)-1,3-oxazol-4-yl]-2-(methylsulfonyl)pyridine

The target compound was prepared in an analogous manner to Intermediate 27 starting with Intermediate 55. LC/MS: m/e 398.9 (M+H)+.

Intermediate 57

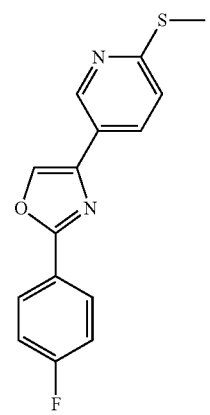 [SMILES: CSc1ccc(-c2coc(-c3ccc(F)cc3)n2)cn1]

5-[2-(4-Fluorophenyl)-1,3-oxazol-4-yl]-2-(methylsulfanyl)pyridine

The target compound was prepared in an analogous manner to Intermediate 11 except that Intermediate 1 was coupled with 5-bromo-2-methylthiopyridine. LC/MS: m/e 286.9 (M+H)+

Intermediate 58

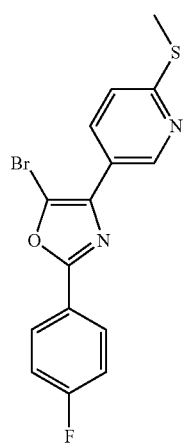 [SMILES: CSc1ccc(-c2nc(-c3ccc(F)cc3)oc2Br)cn1]

5-[5-Bromo-2-(4-fluorophenyl)-1,3-oxazol-4-yl]-2-(methylsulfanyl)pyridine

The target compound was prepared in an analogous manner to Intermediate 27 starting with Intermediate 57. LC/MS: m/e 366.8 (M+H)+

Intermediate 59

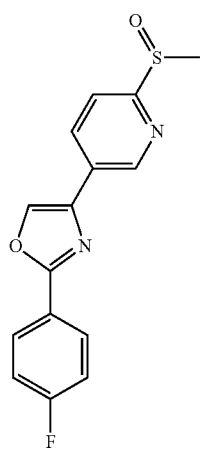 [SMILES: CS(=O)c1ccc(-c2coc(-c3ccc(F)cc3)n2)cn1]

(R)-5-[2-(4-Fluorophenyl)-1,3-oxazol-4-yl]-2-(methylsulfinyl)pyridine and (S)-5-[2-(4-Fluorophenyl)-1,3-oxazol-4-yl]-2-(methylsulfinyl)pyridine To a solution of Intermediate 54 (1.8 g, 6.3 mmol) in DCM (400 mL) at 0° C. was added a solution of mCPBA (1.4 g, 6.3 mmol) in DCM (100 mL) dropwise over 4 h. Upon complete addition, the solution was stirred for an additional 30 min. Upon completion of the reaction as judged by LC/MS analysis, the reaction was quenched with sat. NaHSO₃ solution, extracted with DCM, washed with sat. Na₂CO₃ solution, brine, dried over MgSO₄, filtered, concentrated and purified by on silica gel to afford the title compound (1.14 g). LC/MS: m/e 302.9 (M+H)+.

Intermediate 60

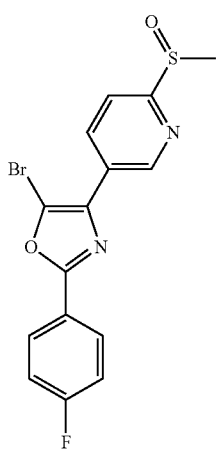 [SMILES: CS(=O)c1ccc(-c2nc(-c3ccc(F)cc3)oc2Br)cn1]

(R)-5-[5-Bromo-2-(4-fluorophenyl)-1,3-oxazol-4-yl]-2-(methylsulfinyl)pyridine and (S)-5-[5-Bromo-2-(4-fluorophenyl)-1,3-oxazol-4-yl]-2-(methylsulfinyl)pyridine The target compound was prepared in an analogous manner to Intermediate 27 starting with Intermediate 59. LC/MS: m/e 282.8 (M+H)+.

Intermediate 61

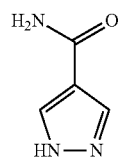

1H-Pyrazole-4-carboxamide

The mixture of 1H-pyrazole-4-carboxylic acid (2.0 g, 17.8 mmol) and thionyl chloride (20 mL, 168 mmol) was heated to reflux. After 4 h, the reaction mixture was concentrated, and then dried at reduced pressure for 0.5 h. The resulting residue was dissolved in CH₂Cl₂ (35 mL), cooled to 0° C. and added to a solution of ammonium hydroxide (46.8 mL, 357 mmol) in CH₂Cl₂ (20 mL). The reaction mixture was warmed to rt and stirred for 12 h. After which point, the mixture was concentrated and CH₃OH/CH₂Cl₂ (1:10, 40 ml) were added and stirred for 10 min. The solution was filtered and washed with CH₃OH/CH₂Cl₂ (1:10). The filtrate was concentrated to give the title compound (1.5 g), which was used in the next step without purification. LC/MS: m/e 112.0 (M+H)+.

Intermediate 62

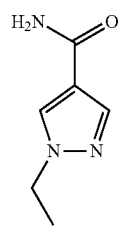

1-Ethyl-1H-pyrazole-4-carboxamide

To a solution of intermediate 61 (1.5 g, 13.5 mmol) in DMF (4 mL) was added powdered $K_2CO_3$ (5.6 g, 40.5 mmol). After 10 min, bromoethane (1.2 mL, 16.2 mmol) was added and the mixture was stirred at rt for 12 h. The reaction mixture was diluted with EtOAc, washed with water, dried over $MgSO_4$ and concentrated to afford the title compound as a white solid (1.0 g), which was used in the next step without purification. LC/MS: m/e 140.1 (M+H)$^+$.

Intermediate 63

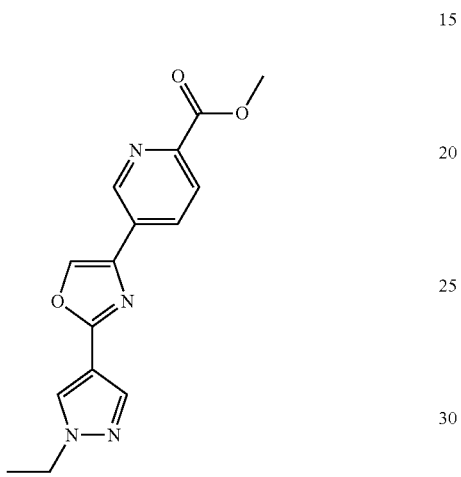

Methyl 5-[2-(1-ethyl-1H-pyrazol-4-yl)-1,3-oxazol-4-yl]pyridine-2-carboxylate

To a solution of Intermediate 39 (650 mg, 2.5 mmol) in toluene (20 mL) in a sealed tube was added Intermediate 62 (876 mg, 6.3 mmol). The reaction mixture was heated to 120° C. for 12 h. The reaction mixture was then concentrated and purified on silica gel to afford the title compound as a white solid (100 mg). LC/MS: m/e 299.2 (M+H)$^+$.

Intermediate 64

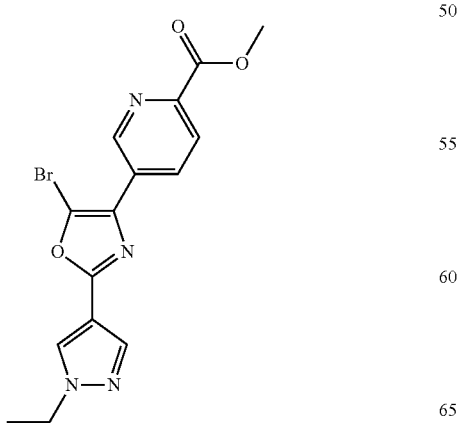

Methyl 5-[5-bromo-2-(1-ethyl-1H-pyrazol-4-yl)-1,3-oxazol-4-yl]pyridine-2-carboxylate The target compound was prepared in an analogous manner to Intermediate 27 starting with Intermediate 63. LC/MS: m/e 379.2 (M+H)$^+$.

Intermediate 65

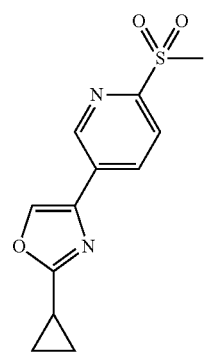 [SMILES: CS(=O)(=O)c1ccc(-c2coc(C3CC3)n2)cn1]

5-(2-Cyclopropyl-1,3-oxazol-4-yl)-2-(methylsulfonyl)pyridine

The target compound was prepared in an analogous manner to Intermediate 44 except starting with Intermediate 43. LC/MS: m/e 264.9 (M+H)$^+$.

Intermediate 66

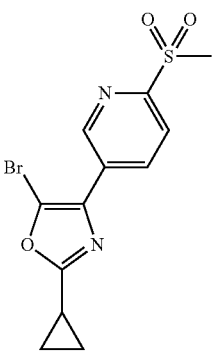 [SMILES: CS(=O)(=O)c1ccc(-c2nc(C3CC3)oc2Br)cn1]

5-(5-Bromo-2-cyclopropyl-1,3-oxazol-4-yl-2-(methylsulfonyl)pyridine

The target compound was prepared in an analogues manner to Intermediate 27 starting with Intermediate 62. LC/MS: m/e 344.8 (M+H)⁺.

Intermediate 67

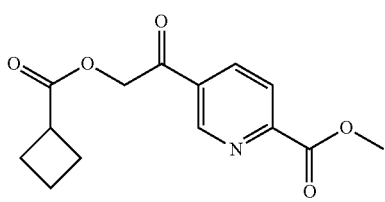 [SMILES: COC(=O)c1ccc(C(=O)COC(=O)C2CCC2)cn1]

Methyl 5-{[(cyclobutylcarbonyl)oxy]acetyl}pyridin-2-carboxylate

The target compound was prepared in an analogous manner to Intermediate 40 except that Intermediate 39 was coupled with cyclobutyl carboxylic acid. LC/MS: m/e 278.0 (M+H)⁺

Intermediate 68

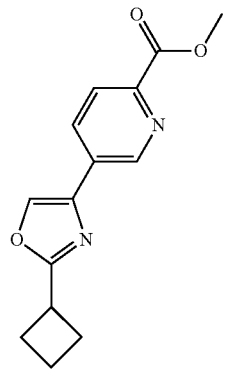 [SMILES: COC(=O)c1ccc(-c2coc(C3CCC3)n2)cn1]

Methyl 5-(2-cyclobutyl-1,3-oxazol-4-yl)pyridine-2-carboxylate

The target compound was prepared in an analogous manner to Intermediate 44 starting with Intermediate 64. LC/MS: m/e 259.1 (M+H)⁺

Intermediate 69

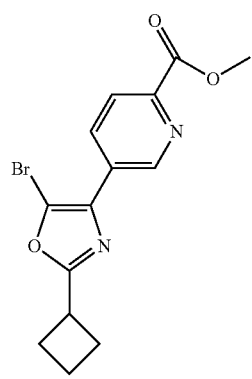 [SMILES: COC(=O)c1ccc(-c2nc(C3CCC3)oc2Br)cn1]

Methyl 5-(5-bromo-2-cyclobutyl-1,3-oxazol-4-yl)pyridine-2-carboxylate

The target compound was prepared in an analogous manner to Intermediate 27 starting with Intermediate 68. LC/MS: m/e 338.9 (M+H)⁺

Intermediate 70

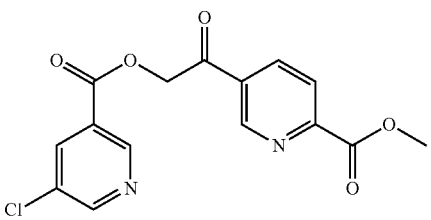 [SMILES: COC(=O)c1ccc(C(=O)COC(=O)c2cncc(Cl)c2)cn1]

81

Methyl 5-({[(5-chloropyridin-3-yl)carbonyl]oxy}acetyl)pyridine-2-carboxylate

The target compound was prepared in an analogous manner to Intermediate 40 except that intermediate 39 was coupled with 5-chloropyridine-3-carboxylic acid. LC/MS: m/e 335.0 (M+H)+.

Intermediate 71

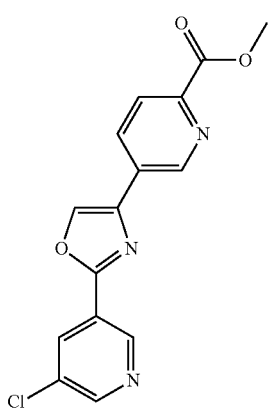 [SMILES: COC(=O)c1ccc(-c2coc(-c3cncc(Cl)c3)n2)cn1]

Methyl 5-[2-(5-chloropyridin-3-yl)-1,3-oxazol-4-yl]pyridine-2-carboxylate

The target compound was prepared in an analogous manner to Intermediate 44 starting with Intermediate 70. LC/MS: m/e 315.9 (M+H)+.

Intermediate 72

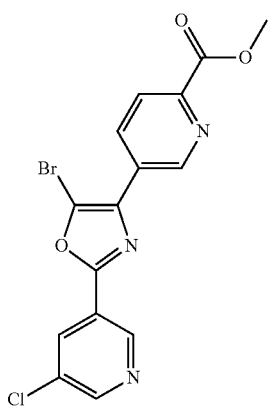 [SMILES: COC(=O)c1ccc(-c2nc(-c3cncc(Cl)c3)oc2Br)cn1]

82

Methyl 5-[5-bromo-2-(5-chloropyridin-3-yl)-1,3-oxazol-yl]pyridine-2-carboxylate

The target compound was prepared in an analogous manner to Intermediate 27 starting with Intermediate 71. LC/MS: m/e 395.8 (M+H)+.

Intermediate 73

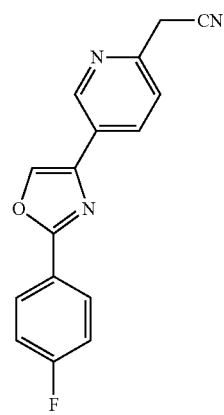 [SMILES: N#CCc1ccc(-c2coc(-c3ccc(F)cc3)n2)cn1]

{5-[2-(4-Fluorophenyl)-1,3-oxazol-4-yl]pyridin-2-yl}acetonitrile

The target compound was prepared in an analogous manner to Intermediate 11 except that Intermediate 1 was coupled with (5-bromopyridin-2-yl)acetonitrile. LC/MS: m/e 280.0 (M+H)+.

Intermediate 74

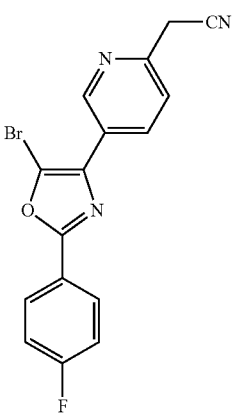 [SMILES: N#CCc1ccc(-c2nc(-c3ccc(F)cc3)oc2Br)cn1]

83

{5-[Bromo-2-(4-fluorophenyl)-1,3-oxazol-4-yl]pyridin-2-yl}acetonitrile

The target compound was prepared in an analogous manner to Intermediate 27. LC/MS: m/e 359.8 (M+H)⁺.

Intermediate 75

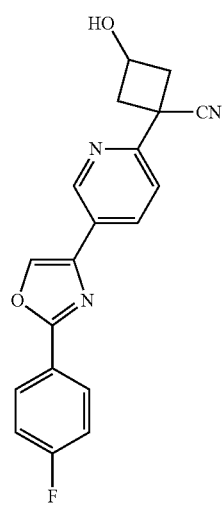 [SMILES: N#CC1(c2ccc(-c3coc(-c4ccc(F)cc4)n3)cn2)CC(O)C1]

1-{5-[2-(4-Fluorophenyl)-1,3-oxazol-4-yl]pyridin-2-yl}-3-hydroxycyclobutanecarbonitrile To a solution of Intermediate 73 (100 mg, 0.4 mmol) in DMF (8 mL) at rt was added NaH (31.5 mg, 0.8 mmol), followed by epichlorohydrin (39.8 mg, 0.4 mmol). The resulting solution was stirred at rt for 1 h. Upon completion of the reaction as judged by TLC analysis, the reaction was quenched with H₂O, extracted with EtOAc, washed with brine, dried over MgSO₄, filtered, concentrated and purified on silica gel to afford the title compound (16 mg). LC/MS: m/e 336.1 (M+H)⁺.

Intermediate 76

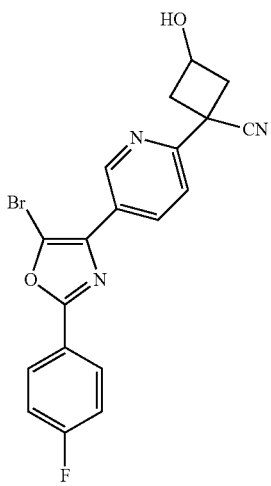 [SMILES: N#CC1(c2ccc(-c3nc(-c4ccc(F)cc4)oc3Br)cn2)CC(O)C1]

84

1-{5-[5-Bromo-2-(4-fluorophenyl)-1,3-oxazol-4-yl]pyridin-2-yl}-3-hydroxy cyclobutanecarbonitrile The target compound was prepared in an analogous manner to Intermediate 27. LC/MS: m/e 415.9 (M+H)⁺.

Intermediate 77

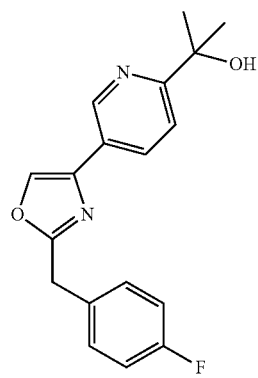 [SMILES: CC(C)(O)c1ccc(-c2coc(Cc3ccc(F)cc3)n2)cn1]

2-{5-[2-(4-Fluorobenzyl)-1,3-oxazol-4-yl]pyridin-2-yl}propan-2-ol

The target compound was prepared in an analogous manner to Intermediate 11 except that Intermediate 1 was replaced with Intermediate 25. LC/MS: m/e 313.1 (M+H)⁺.

Intermediate 78

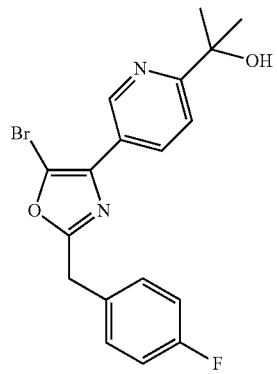 [SMILES: CC(C)(O)c1ccc(-c2nc(Cc3ccc(F)cc3)oc2Br)cn1]

2-{5-[5-Bromo-2-(4-fluorobenzyl)-1,3-oxazol-4-yl]pyridin-2-yl}propan-2-ol

The target compound was prepared in an analogous manner to intermediate 27. LC/MS: m/e 393.0 (M+H)$^+$.

Intermediate 79

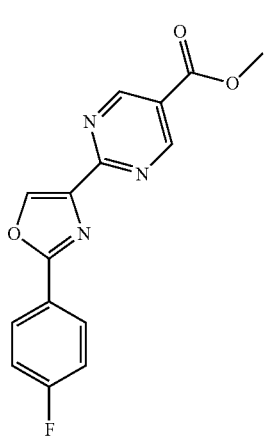 [SMILES: COC(=O)c1cnc(-c2coc(-c3ccc(F)cc3)n2)nc1]

Methyl 2-[2-(4-fluorophenyl)-1,3-oxazol-4-yl]pyrimidine-5-carboxylate

The target compound was prepared in an analogous manner to Intermediate 11 except that Intermediate 1 was coupled with methyl 2-chloropyrimidine-5-carboxylate. LC/MS: m/e 300.1 (M+H)$^+$.

Intermediate 80

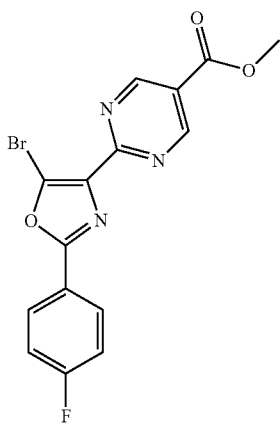 [SMILES: COC(=O)c1cnc(-c2nc(-c3ccc(F)cc3)oc2Br)nc1]

Methyl 2-[5-bromo-2-(4-fluorophenyl)-1,3-oxazol-4-yl]pyrimidine-5-carboxylate The target compound was prepared in an analogous manner to Intermediate 27 starting with Intermediate 79. LC/MS: m/e 377.9 (M+H)$^+$.

Intermediate 81

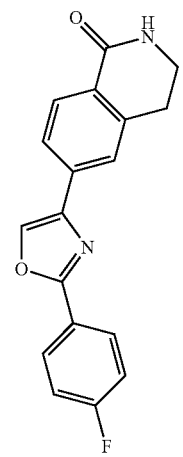 [SMILES: O=C1NCCc2cc(-c3coc(-c4ccc(F)cc4)n3)ccc21]

6-[2-(4-Fluorophenyl)-1,3-oxazol-4-yl]-3,4-dihydroisoquinolin-1(2H)-one

The target compound was prepared in an analogous manner to Intermediate 11 except that Intermediate 1 was coupled with 6-bromo-3,4-dihydroisoquinolin-1(2H)-one (*Bioorg. Med. Chem. Lett.*, 2006, 16, 2584). LC/MS: m/e 309.3 (M+H)$^+$.

Intermediate 82

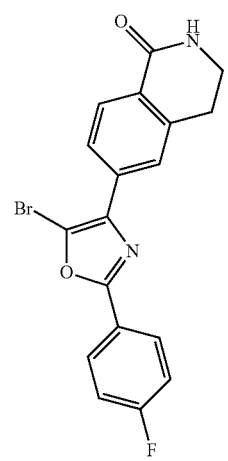 [SMILES: O=C1NCCc2cc(-c3nc(-c4ccc(F)cc4)oc3Br)ccc21]

6-[5-Bromo-2-(4-fluorophenyl)-1,3-oxazol-4-yl]-3,4-dihydroisoquinolin-1-(2H)-one The target compound was prepared in an analogous manner to Intermediate 27 starting with Intermediate 81. LC/MS: m/e 388.9 (M+H)⁺.

Intermediate 83

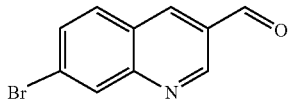

7-Bromoquinoline-3-carbaldehyde

The title compound was prepared using the procedure described by Sato, I.; Nakao, T.; Sugie, R.; Kawasaki, T.; Soai, K. *Synthesis* 2004, 9, 1419.

Intermediate 84

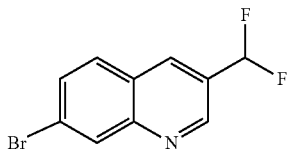 [SMILES: FC(F)c1cnc2cc(Br)ccc2c1]

7-Bromo-3-(difluoromethyl)quinoline

Dissolved the Intermediate 83 (72 mg, 0.30 mmol) in CH₂Cl₂ (1 mL) and added a solution of Deoxo-Fluor (0.096 mL, 0.519 mmol) in CH₂Cl₂ (1 ml) followed by EtOH (0.004 mL, 0.069 mmol). Stirred overnight at rt. Diluted with CH₂Cl₂ and added sat'd. NaHCO₃. Extracted with CH₂Cl₂ (3×), dried over MgSO₄, filtered, evaporated and dried under high vac at rt. Light yellow oil. Purified by prep TLC (SiO₂, 20×20 cm, 1000 microns, 1 plate; hexane-EtOAc, 9:1) to afford title compound (59 mg). LC/MS: [M+H]⁺ m/e 258, 260 (M+H)⁺.

Intermediate 85

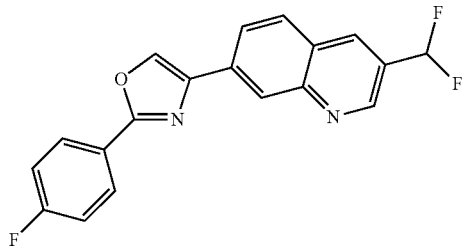 [SMILES: Fc1ccc(-c2nc(-c3ccc4cc(C(F)F)cnc4c3)co2)cc1]

3-(Difluoromethyl)-7-[2-(4-fluorophenyl)-1,3-oxazol-4-yl]quinoline

The target compound was prepared in an analogous manner to Intermediate 11 except that Intermediate 1 was coupled with 7-Bromo-3-(difluoromethyl)quinoline. LC/MS: m/e 341.5.

Intermediate 86

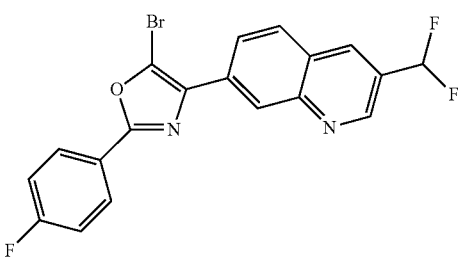 [SMILES: Fc1ccc(-c2nc(-c3ccc4cc(C(F)F)cnc4c3)c(Br)o2)cc1]

7-[5-Bromo-2-(4-fluorophenyl)-1,3-oxazol-4-yl]-3-(difluoromethyl)quinoline

The target compound was prepared in an analogous manner to Intermediate 27 starting with Intermediate 85 LC/MS: m/e 421 (M+H)⁺.

Intermediate 87

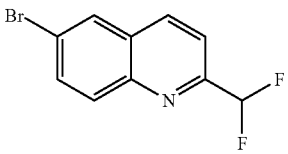 [SMILES: FC(F)c1ccc2cc(Br)ccc2n1]

6-Bromo-2-(difluoromethyl)quinoline

Suspended 6-bromoquinoline-2-carbaldehyde (472 mg, 2 mmol) in CH₂Cl₂ (2 mL) and added a solution of Deoxo-Fluor (0.627 mL, 3.4 mmol) in CH₂Cl₂ (2 mL) followed by EtOH (0.023 mL, 0.4 mmol). Stirred for 48 hrs at rt. Diluted with CH₂Cl₂ and added sat'd. NaHCO₃. Extracted with CH₂Cl₂ (3×), washed extracts with brine (1×), dried over MgSO₄, filtered, evaporated and dried under high vac at rt. The light brown solids were dissolved in a small amount of CH₂Cl₂-MeOH and stirred with a small amount of silica gel for 15 min. Filtered, evaporated and dried under high vac at rt to afford the title compound (491 mg). LC/MS: m/e 258, 260 (M+H)⁺.

Intermediate 88

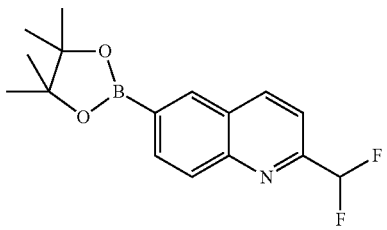 [SMILES: CC1(C)OB(c2ccc3nc(C(F)F)ccc3c2)OC1(C)C]

2-(Difluoromethyl)-6-(4,4,5,5-tetramethyl-1,3,2-dioxaborolan-2-yl)quinoline

Mixed the Intermediate 87 (504 mg, 1.953 mmol), bis(pinacolato)diboron (506 mg, 1.992 mmol), PdCl$_2$(dppf) (43 mg, 0.059 mmol) and KOAc (575 mg, 5.86 mmol) with DMSO (4.0 mL) in a sealed vial. Degassed by bubbling in N$_2$ gas and then blanketing vessel with N$_2$ and sealed with Teflon stopper. Heated to 80° C. Heated and stirred overnight.

Cooled to rt after 16 hrs. Diluted with water and extracted with EtOAc (3×), washed with brine (1×), dried over MgSO$_4$, decolorized with charcoal, filtered, evaporated and dried under high vac at rt to afford the title compound (788 mg). LC/MS: m/e 306 (M+H)⁺.

Intermediate 89

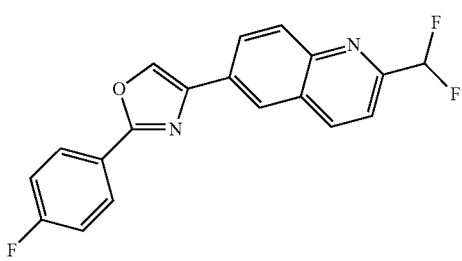 [SMILES: Fc1ccc(-c2nc(-c3ccc4nc(C(F)F)ccc4c3)co2)cc1]

2-(Difluoromethyl-6-[2-(4-fluorophenyl)-1,3-oxazol-4-yl]quinoline

Dissolved 2-(4-fluorophenyl)-1,3-oxazol-4-yl trifluoromethanesulfonate (185 mg, 0.593 mmol) and Intermediate 88 (263 mg, 0.652 mmol) in DMF (3.2 mL) and added PdCl$_2$(dppf) (13 mg, 0.018 mmol) followed by Na$_2$CO$_3$ (314 mg, 2.97 mmol) and water (0.72 mL) in a sealed tube. The flask was sealed with a Teflon stopper and heated at 90° C. After 5 h the reaction was cooled to rt, diluted with water and extracted with CH$_2$Cl$_2$ (3×). Washed extracts with brine (1×), dried over MgSO$_4$, decolorized with charcoal and filtered through filtercel. Evaporated filtrate to dryness and dried under high vac at rt. The brown solids were purified by prep TLC (SiO$_2$, 20×20 cm, 1000 microns, 3 plates; hexane-EtOAc, 3:1) to afford the title compound (109 mg). LC/MS: m/e 341 (M+H)⁺.

Intermediate 90

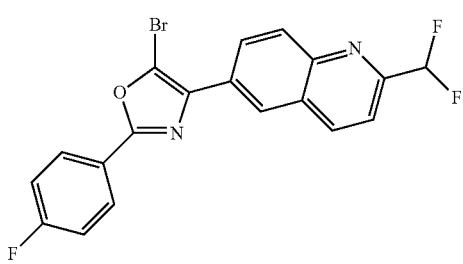 [SMILES: Fc1ccc(-c2nc(-c3ccc4nc(C(F)F)ccc4c3)c(Br)o2)cc1]

6-[5-Bromo-2-(4-fluorophenyl)-1,3-oxazol-4-yl]-2-(difluoromethyl)quinoline

The target compound was prepared in an analogous manner to Intermediate 27 starting with Intermediate 89. LC/MS: m/e 421 (M+H)⁺.

Intermediate 91

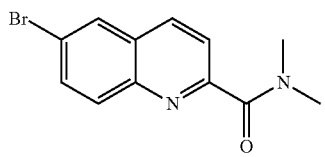 [SMILES: CN(C)C(=O)c1ccc2cc(Br)ccc2n1]

6-Bromo-N,N-dimethylquinoline-2-carboxamide

Suspended the 6-bromoquinoline-2-carboxylic acid (1.0 g, 3.93 mmol) in CH$_2$Cl$_2$ (20 mL), added DMF (0.91 mL, 11.78 mmol) and cooled in an ice bath. Added oxalyl chloride (0.688 mL, 7.86 mmol) dropwise over a few min. Warmed to rt and stirred for 1 hr then bubbled in dimethylamine gas for several min. The dark amber mixture was stirred at rt overnight. In am, the solution was diluted with water and extracted with CH$_2$Cl$_2$ (3×). Washed extracts with brine (1×), dried over MgSO$_4$, decolorized with charcoal, filtered, evaporated and dried under high vac, rt to afford the title compound (990 mg). LC/MS: m/e 279, 281 (M+H)+.

Intermediate 92

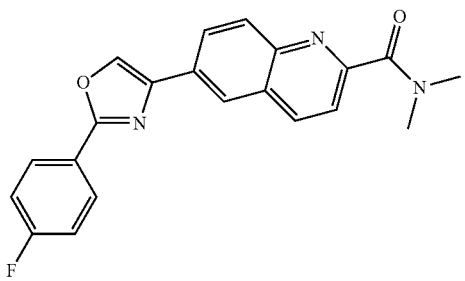 [SMILES: CN(C)C(=O)c1ccc2cc(-c3coc(-c4ccc(F)cc4)n3)ccc2n1]

6-[2-(4-Fluorophenyl)-1,3-oxazol-4-yl]-N,N-dimethylquinoline-2-carboxamide

The target compound was prepared in an analogous manner to Intermediate 11 except that Intermediate 1 was coupled with Intermediate 91. LC/MS: m/e 362.4 (M+H)+.

Intermediate 93

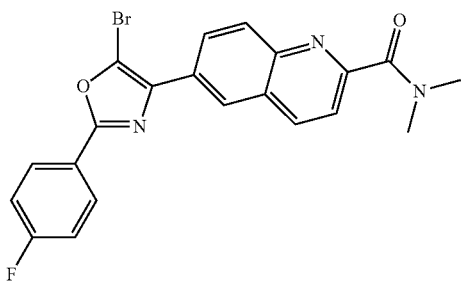 [SMILES: CN(C)C(=O)c1ccc2cc(-c3nc(-c4ccc(F)cc4)oc3Br)ccc2n1]

6-[5-Bromo-2-(4-fluorophenyl)-1,3-oxazol-4-yl]-N,N-dimethylquinoline-2-carboxamide The target compound was prepared in an analogous manner to Intermediate 27 starting with Intermediate 92. LC/MS: m/e 442.1 (M+H)+.

Intermediate 94

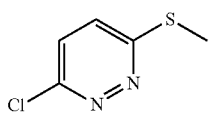

3-Chloro-6-(methylsulfanyl)pyridazine

Dissolved 2,5-dichloropyridazine (8.7 g, 58.4 mmol) in DMF (30 mL) and added a solution of $CH_3SNa$ (4.1 g, 58.5 mmol) in DMF (60 mL) over 15 min. Mild exotherm which was controlled by use of a cold water bath. Stirred at rt for 12 h. Evaporated much of the DMF (~50 mL) then diluted with a large volume of water when solid precipitates. Stirred at rt for 2 h then filtered the white solids and washed with water. Dissolved the solid in $CH_2Cl_2$, separated out the water and dried over $MgSO_4$. Filtered, evaporated and dried under high vac at rt to afford the title compound (5.77 g). LC/MS: m/e 161 (M+H)+.

Intermediate 95

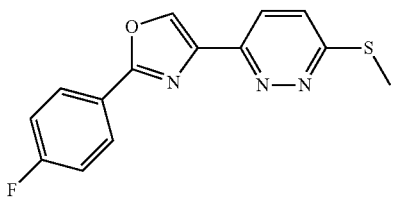 [SMILES: CSc1ccc(-c2coc(-c3ccc(F)cc3)n2)nn1]

3-[2-(4-Fluorophenyl)-1,3-oxazol-4-yl]-6-(methylsulfanyl)pyridine

The target compound was prepared in an analogous manner to Intermediate 11 except that Intermediate 1 was coupled with Intermediate 94. LC/MS: m/e 288 (M+H)+.

Intermediate 96

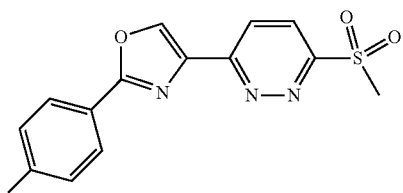

3-[2-(4-Fluorophenyl)-1,3-oxazol-4-yl]-6-(methylsulfonyl)pyridazine

Intermediate 95 (135 mg, 0.47 mmol) in MeOH (25.0 mL) was treated with a solution of oxone (867 mg, 1.41 mmol) in water (5.0 mL) dropwise and stirred at rt. The solution was then evaporated to dryness, extracted with $CH_2Cl_2$ (3×). The combined organic extracts were dried over MgSO₄, filtered and evaporated to afford the title compound (134 mg). LC/MS: m/e 320 (M+H)⁺.

Intermediate 97

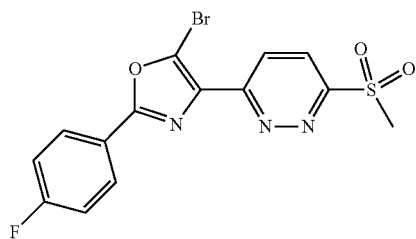 [SMILES: CS(=O)(=O)c1ccc(-c2nc(-c3ccc(F)cc3)oc2Br)nn1]

3-[5-Bromo-2-(4-fluorophenyl-1,3-oxazol-4-yl]-6-(methylsulfonyl)pyridazine

The target compound was prepared in an analogous manner to Intermediate 27 starting with Intermediate 96. LC/MS: m/e 399.7 (M+H)⁺.

Intermediate 98

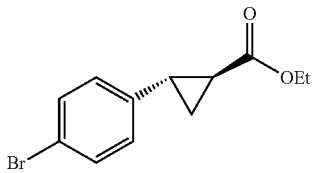 [SMILES: CCOC(=O)[C@H]1C[C@@H]1c1ccc(Br)cc1]

Ethyl(1S,2S)-2-(4-bromophenyl)cyclopropanecarboxylate

To a 1-neck, 1-L round bottom flask equipped with a magnetic stirrer was added 265 mL methyl tert-butyl ether. The flask was evacuated and flushed with nitrogen three times. 2,2'-Isopropylidenebis[(4R)-4-tert-butyl-2-oxazolidine] (2.39 g, 8.03 mmol) was added, followed by copper(I) tridluoromethanesulfonate benzene complex (4.49 g, 8.03 mmol). The green suspension was stirred at room temperature for about 2 hours and was then filtered. The filtrate was added to a 4-neck, 5-L, round bottom flask equipped with a mechanical stirrer, thermocouple, nitrogen bubbler, and addition funnel. Then, 4-bromostyrene (150 g, 0.803 mol) was added to this solution and the reaction was cooled to 0° C. via an ice/water bath. Ethyl diazoacetate (167 mL, 1.606 mol) was dissolved in 1675 mL of MTBE and the solution was evacuated/flushed with nitrogen three times. This solution was then added to an addition funnel and added dropwise to the reaction mixture. A slight exotherm was observed. The ethyl diazoacetate was allowed to add slowly over the weekend and the reaction slowly warmed to room temperature. The reaction was poured into a large extractor and diluted with 4 L MTBE. The organics were washed with 2×1 L 3% aq. ammonium hydroxide and 2 L brine, dried over anhydrous magnesium sulfate, filtered, and concentrated. The residue was dissolved in heptane and a small amount of dichloromethane, injected onto an ISCO 1500 g column prepacked in heptane. The column was eluted with 100% heptane over 1 column volume, 0-20% ethyl acetate/heptane over 6.5 column volumes, and held at 20% ethyl acetate/heptane over 8 column volumes. The product containing fractions were collected and concentrated to give 191 g (yield 88%) of the title compound. 1H NMR (500 MHz, (CDCl₃): 7.42 (d, 2H), 7.01 (d, 2H), 4.21 (q, 2H), 2.49 (m, 1H), 1.88 (m, 1H), 1.62 (m, 2H), 1.25 (t, 3H).

The compounds in Table 5 were prepared from the appropriate starting materials using the procedure for Example 12.

TABLE 5

| Example | R₂ | R₃ | LCMS: found m/e (M + H) |
|---|---|---|---|
| 57 | 2,4-difluorophenyl | 4-chlorophenyl | 477.1 |
| 58 | 2,4-difluorophenyl | 5-chloropyridin-2-yl | 478.1 |
| 59 | 4-methylphenyl | 5-chloropyridin-2-yl | 438.1 |
| 60 | 4-methylphenyl | 5-chloropyrimidin-2-yl | 439.1 |
| 61 | 4-methylphenyl | 4-chlorophenyl | 437.2 |

TABLE 5-continued

| Example | R₂ | R₃ | LCMS: found m/e (M + H) |
|---|---|---|---|
| 62 | phenyl | 5-chloropyrimidin-2-yl | 425.1 |
| 63 | phenyl | 5-chloropyridin-2-yl | 424.2 |
| 64 | phenyl | 4-chlorophenyl | 423.1 |
| 65 | 4-fluorophenyl | 2-fluoro-4-methoxyphenyl | 445.0 |
| 66 | 4-fluorophenyl | 5-nitropyridin-2-yl | 453.0 |
| 67 | 4-(trifluoromethoxy)phenyl | 5-chloropyrimidin-2-yl | 508.9 |
| 68 | 4-(trifluoromethoxy)phenyl | 5-chloropyridin-2-yl | 507.9 |
| 69 | 4-methoxyphenyl | 5-chloropyridin-2-yl | 454.0 |

Example 70

5-{5-[(5-chloropyridin-2-yl)sulfanyl]-2-(4-fluorophenyl)-1,3-oxazol-4-yl}pyridine-2-carbonitrile The title compound was prepared in an analogous manner to Example 12 starting with Intermediate 33. LC/MS: mile 409.9 (M+H)⁺. ¹H NMR (500 MHz, Acetone-d6): δ 7.39 (m, 2H), 7.48 (d, J=8.5 Hz, 1H), 7.83 (m, 1H), 8.05 (d, J=8.5 Hz, 1H), 8.24 (m, 2H), 8.45 (d, J=2.5 Hz, 1H), 8.72 (m, 1H), 9.44 (d, J=1.5 Hz, 1H).

Example 71

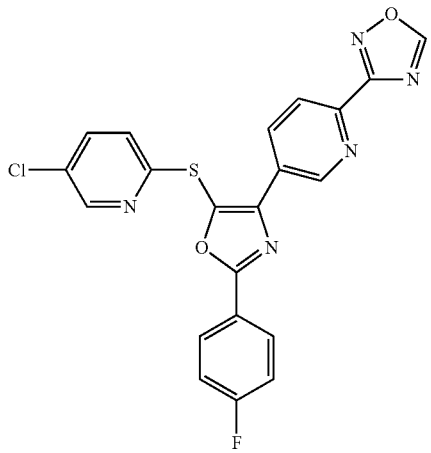 [SMILES: Fc1ccc(-c2nc(-c3ccc(-c4ncon4)nc3)c(Sc3ccc(Cl)cn3)o2)cc1]

5-Chloro-2-({2-(4-fluorophenyl)-4-[6-(1,2,4-oxadiazol-3-yl)pyridin-3-yl]-1,3-oxazol-5-yl}sulfanyl)pyridine To Example 70 (100 mg, 0.25 mmol) in 10 mL EtOH was added 1.0 mL of 50 wt % aqueous NH$_2$OH and 15 mg of K$_2$CO$_3$. The reaction was heated to 120° C. for 5 min via microwave irradiation. The reaction mixture was concentrated to dryness and the residue was dissolved in 5 mL triethylorthoformate, 10 mL EtOH and 1 mL of TFA. The reaction was heated to 100° C. for 10 min via microwave irradiation. The volatiles were removed and the residue was purified on silica gel to afford the title compound (64 mg). LC/MS: m/e 452.0 (M+H)$^+$. $^1$H NMR (500 MHz, Acetone-d6): δ 7.37-7.41 (m, 3H), 7.82 (m, 1H), 8.27 (m, 2H), 8.47 (d, J=2.0 Hz, 1H), 8.69 (d, J=6.5 Hz, 1H), 9.47 (s, 1H).

Example 72

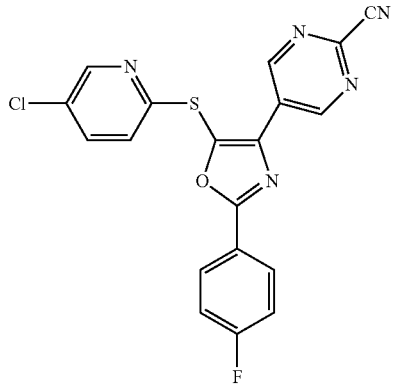 [SMILES: N#Cc1ncc(-c2nc(-c3ccc(F)cc3)oc2Sc2ccc(Cl)cn2)cn1]

5-{5-[(5-Chloropyridin-2-yl)sulfanyl]-2-(4-fluorophenyl)-1,3-oxazol-4-yl}pyrimidine-2-carbonitrile The title compound was prepared in an analogous manner to Example 12 starting with Intermediate 31. LC/MS: m/e 410.0 (M+H)$^+$. $^1$H NMR (500 MHz, Acetone-d6): δ 7.41 (m, 2H), 7.53 (d, J=8.5 Hz, 1H), 7.84 (m, 1H), 8.26 (m, 2H), 8.45 (d, J=2.5 Hz, 1H), 9.61 (s, 2H).

Example 73

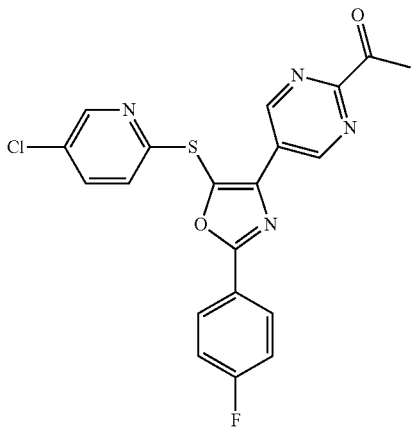 [SMILES: CC(=O)c1ncc(-c2nc(-c3ccc(F)cc3)oc2Sc2ccc(Cl)cn2)cn1]

1-(5-{5-[(5-Chloropyridin-2-yl)sulfanyl]-2-(4-fluorophenyl)-1,3-oxazol-4-yl}pyrimidin-2-yl)ethanone A solution of 5-{5-[(5-chloropyridin-2-yl)sulfanyl]-2-(4-fluorophenyl)-1,3-oxazol-4-yl}pyrimidine-2-carbonitrile (Example 72) (87 mg, 0.21 mmol) in THF (5 mL) was treated with methylmagnesium bromide (0.7 mL, 2.1 mmol, 3.0 M in THF) at rt. Upon completion of the reaction as judged by TLC analysis, the solution was diluted with saturated aq NH$_4$Cl solution and extracted with EtOAc. The organic layer was removed, dried over MgSO$_4$, filtered and concentrated giving rise to an oil. The oil was purified on silica gel to afford the title compound (13 mg). LC/MS: m/e 427.0 (M+H)$^+$. $^1$H NMR (500 MHz, Acetone-d6): δ 2.70 (s, 3H), 7.41 (m, 2H), 7.51 (d, J=9.0 Hz, 1H), 7.83 (m, 1H), 8.27 (m, 2H), 8.45 (d, J=2.5 Hz, 1H), 9.57 (s, 2H).

Example 74

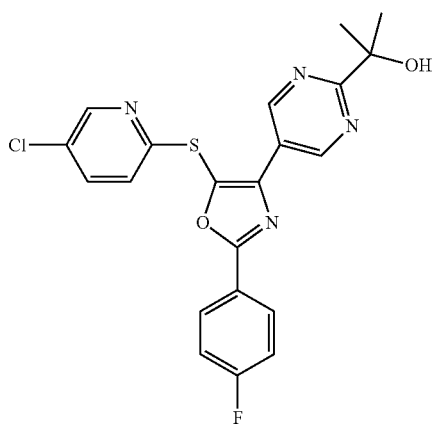 [SMILES: CC(C)(O)c1ncc(-c2nc(-c3ccc(F)cc3)oc2Sc2ccc(Cl)cn2)cn1]

2-(5-{5-[(5-Chloropyridin-2-yl)sulfanyl]-2-(4-fluorophenyl)-1,3-oxazol-4-yl}pyrimidin-2-yl)propan-2-ol A solution of 1-(5-{5-[(5-chloropyridin-2-yl)sulfanyl]-2-(4-fluorophenyl)-1,3-oxazol-4-yl}pyrimidin-2-yl)ethanone (Example 73) (12 mg, 0.03 mmol) in THF (5 mL) was treated with methylmagnesium bromide (0.09 mL, 0.3 mmol, 3.0 M in THF) at it. Upon completion of the reaction as judged by TLC analysis, the solution was diluted with saturated aq NH₄Cl solution and extracted with EtOAc. The organic layer was removed, dried over MgSO₄, filtered and concentrated giving rise to an oil. The oil was purified on silica gel to afford the title compound (6.3 mg). LC/MS: m/e 443.0 (M+H)⁺. ¹H NMR (500 MHz, Acetone-d6): δ 1.54 (s, 6H), 4.56 (s, 1H), 7.39 (m, 2H), 7.47 (d, J=8.5 Hz, 1H), 7.82 (m, 1H), 8.25 (m, 2H), 8.45 (d, J=2.5 Hz, 1H), 9.39 (s, 2H).

The compounds in Table 6 were prepared from the appropriate starting materials using the procedure for Example 12.

TABLE 6

| Example | $R_2$ | $R_3$ | LCMS: found m/e (M + H) |
|---|---|---|---|
| 75 | 4-F-C₆H₄ | 5-F-pyridin-2-yl | 427.0 |
| 76 | 4-F-C₆H₄ | 4-MeO-C₆H₄ | 438.0 |
| 77 | 4-F-C₆H₄ | 5-Cl-pyrimidin-2-yl | 443.9 |

Example 78

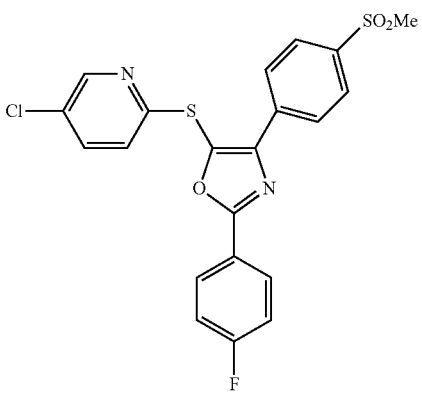 [SMILES: CS(=O)(=O)c1ccc(-c2nc(-c3ccc(F)cc3)oc2Sc2ccc(Cl)cn2)cc1]

5-Chloro-2-({2-(4-fluorophenyl)-4-[4-(methylsulfonyl)phenyl]-1,3-oxazol-5-yl}sulfanyl)pyridine A stirred solution of Intermediate 29 (1.30 g, 3.30 mmol), 5-chloropyridine-2-thiol (573 mg, 3.90 mmol), and K₂CO₃

(1.36 g, 9.80 mmol) dissolved in 60 mL of NMP was heated to 60° C. for 1 h. After which point, the solution was diluted with dist. H$_2$O and EtOAc. The organic layer was removed followed by drying over MgSO$_4$, filtration and concentration giving rise to an oil. The oil was purified on silica gel to afford the title compound (130 mg). LC/MS: m/e 460.7 (M+H)$^+$. $^1$H NMR (500 MHz, CDCl$_3$): δ 3.09 (s, 3H), 7.05 (d, J=8.5 Hz, 1H), 7.22 (m, 2H), 7.56 (m, 1H), 8.01 (d, J=8.5 Hz, 2H), 8.19 (m, 2H), 8.37 (d, J=8.5 Hz, 2H), 8.41 (d, J=2.5 Hz, 1H).

Example 79

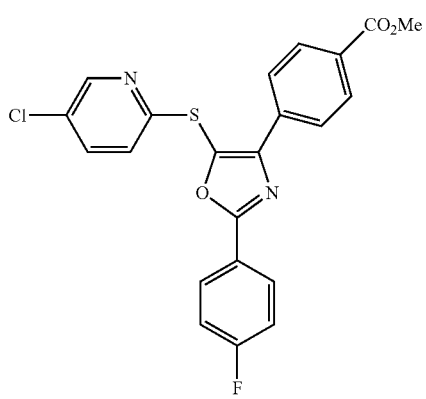 [SMILES: COC(=O)c1ccc(-c2nc(-c3ccc(F)cc3)oc2Sc2ccc(Cl)cn2)cc1]

Methyl-4-{5-[(5-chloropyridin-2-yl)sulfanyl]-2-(4-fluorophenyl)-1,3-oxazol-4-yl}benzoate A stirred solution of Intermediate 27 (500 mg, 1.30 mmol), 5-chloropyridine-2-thiol (290 mg, 2.00 mmol), and K$_2$CO$_3$ (551 mg, 4.00 mmol) dissolved in 20 mL of NMP was heated to 80° C. for 12 h. After which point, the solution was diluted with dist. H$_2$O and EtOAc. The organic layer was removed followed by drying over MgSO$_4$, filtration and concentration giving rise to an oil. The oil was purified on silica gel to afford the title compound (330 mg). LC/MS: m/e 440.9 (M+H)$^+$. $^1$H NMR (500 MHz, CDCl$_3$): δ 3.95 (s, 3H), 7.02 (d, J=8.5 Hz, 1H), 7.22 (m, 2H), 7.56 (m, 1H), 8.11 (d, J=8.5 Hz, 2H), 8.13 (m, 2H), 8.25 (d, J=8.5 Hz, 2H), 8.43 (d, J=2.5 Hz, 1H).

Example 80

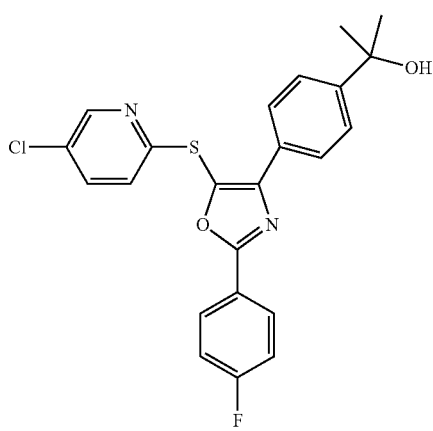 [SMILES: CC(C)(O)c1ccc(-c2nc(-c3ccc(F)cc3)oc2Sc2ccc(Cl)cn2)cc1]

2-(4-{5-[(5-Chloropyridin-2-yl)sulfanyl]-2-(4-fluorophenyl)-1,3-oxazol-4-yl}phenyl)propan-2-ol A solution of methyl-4-{5-[(5-chloropyridin-2-yl)sulfanyl]-2-(4-fluorophenyl)-1,3-oxazol-4-yl}benzoate (Example 79) (127 mg, 0.29 mmol) in THF (10 mL) was treated with methylmagnesium bromide (0.50 mL, 1.4 mmol, 3.0 M in THF) at rt. Upon completion of the reaction as judged by TLC analysis, the solution was diluted with saturated aq NH$_4$Cl solution and extracted with EtOAc. The organic layer was removed, dried over MgSO$_4$, filtered and concentrated giving rise to an oil. The oil was purified on silica gel to afford the title compound (100 mg). LC/MS: m/e 441.0 (M+H)$^+$.

Example 81

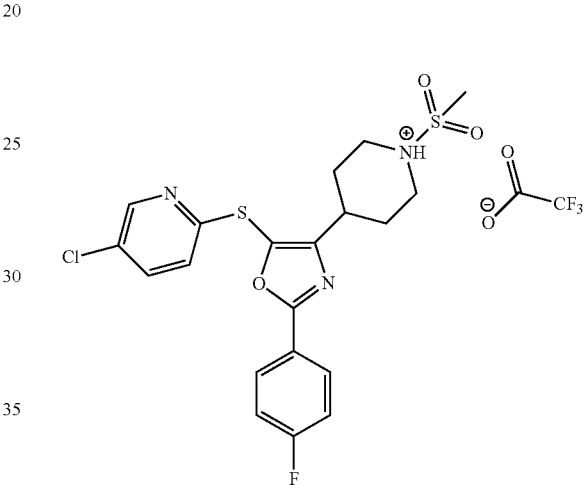

4-{5-[(5-Chloropyridin-2-yl)sulfanyl]-2-(4-fluorophenyl)-1,3-oxazol-4-yl}-1-(methylsulfonyl)piperidinium trifluoroacetate A solution of Intermediate 35 (100 mg, 0.925 mmol) in CH$_2$Cl$_2$ (10 mL) was stirred at rt for 16 h. Upon completion of the reaction as judge by TLC, the solution was diluted with CH$_2$Cl$_2$ (20 mL) and sat aq. Na$_2$S$_2$O$_3$ (30 mL). The organic layer was removed, dried over MgSO$_4$, filtered and concentrated to afford the corresponding bromide. The material was taken onto the next step directly. At this point, a solution of 5-chloropyridine-2-thiol (79 mg, 0.564 mmol) in DME (2 mL) was added K$_2$CO$_3$ (113 mg, 0.818 mmol) and stirred at rt for 15 min. A solution of the freshly prepared bromide (110 mg, 0.273 mmol), neocuproine (14.0 mg, 0.068 mmol) and CuI (13 mg, 0.068 mmol) in DME (2 mL) was added to the mixture and heated to 90° C. for 2 h. The solution was allowed to cool to rt, concentrated under vacuum and the residue was purified by reverse phase HPLC to afford 9 mg of the final compound as a TFA salt. LCMS: m/z 468.0 (M+H)$^+$.

The compounds in Table 7 were prepared from the appropriate starting materials using the procedure for Example 12.

TABLE 7

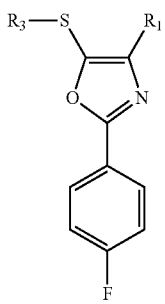

| Example | R₁ | R₃ | LCMS: found m/e (M + H) |
|---|---|---|---|
| 82 | (4-pyridyl-C(CH₃)₂OH) | (5-chloropyridin-2-yl) | 442.1 |
| 83 | (3-pyridyl-C(CH₃)₂OH) | (5-chloropyridin-2-yl) | 442.1 |

Example 84

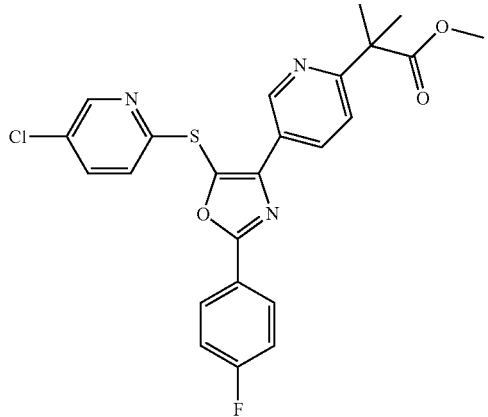 [SMILES: COC(=O)C(C)(C)c1ccc(-c2nc(-c3ccc(F)cc3)oc2Sc2ccc(Cl)cn2)cn1]

Methyl 2-(5-{5-[(5-chloropyridin-2-yl)sulfanyl]-2-(4-fluorophenyl)-1,3-oxazol-4-yl}pyridin-2-yl)-2-methylpropanoate The title compound was prepared in an analogous manner to Example 12 starting with Intermediate 37. LC/MS: m/e 484.1 (M+H)⁺.

Example 85

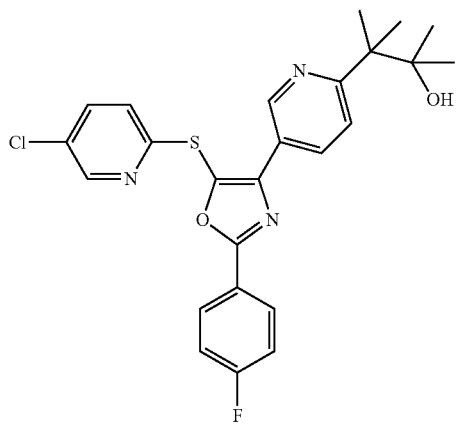 [SMILES: CC(C)(O)C(C)(C)c1ccc(-c2nc(-c3ccc(F)cc3)oc2Sc2ccc(Cl)cn2)cn1]

3-(5-{5-[(5-chloropyridin-2-yl)sulfanyl]-2-(4-fluorophenyl)-1,3-oxazol-4-yl}pyridin-2-yl)-2,3-dimethylbutan-2-ol The title compound was prepared in an analogous manner to Example 80 starting with Example 84. LC/MS: m/e 484.2 (M+H)⁺. ¹H NMR (500 MHz, acetone-d6): δ 1.04 (s, 6H), 1.41 (s, 6H), 7.39 (m, 3H), (7.36 (d, J=8 Hz, 1H), 7.80 (dd, J=2.5, 8.5 Hz, 1H), 8.24 (m, 2H), 8.44 (m, 2H), 9.23 (d, J=1.5 Hz, 1H).

Example 86

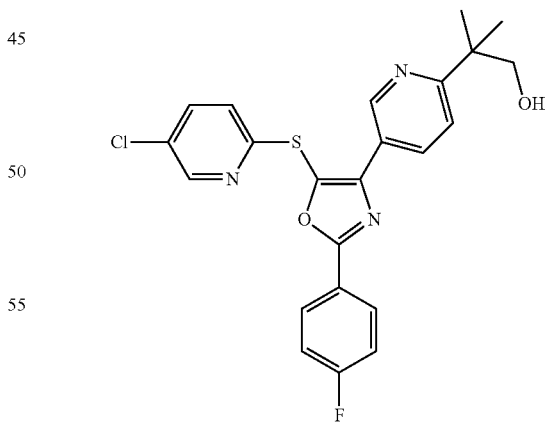

2-(5-{5-[(5-chloropyridin-2-yl)sulfanyl]-2-(4-fluorophenyl)-1,3-oxazol-4-yl}pyridin-2-yl)-2-methylpropan-1-ol To a solution of Example 84 (120 mg, 0.2 mmol) in THF (10 mL) at −78° C. was added DIBAl-H (1.0M/toluene, 0.6 mL, 0.6 mmol). The resulting solution was stirred at −78° C. for 1 h. The reaction mixture was then poured into a vigorously stirred Rochelle salt solution/EtOAc (1:1). Upon clarification of the organic layer, the layers were separated, dried over MgSO$_4$, filtered, concentrated and purified on silica gel to afford the title compound (95.7 mg). LC/MS: m/e 456.1 (M+H)$^+$. $^1$H NMR (500 MHz, acetone-d6): δ 1.35 (s, 6H), 3.73 (d, J=5.5 Hz, 2H), 4.08 (t, J=5.5 Hz, 1H) 7.40 (m, 3H), 7.58 (d, J=7.5 Hz, 1H), 7.82 (dd, J=3, 9 Hz, 1H), 8.25 (m, 2H), 8.39 (dd, J=2.5, 8.5 Hz, 1H), 8.47 (d, 2.5J=2.5 Hz, 1H), 9.21 (s, 1H).

Example 87

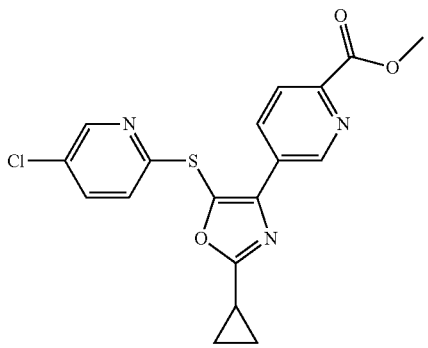 [SMILES: COC(=O)c1ccc(-c2nc(C3CC3)oc2Sc2ccc(Cl)cn2)cn1]

Methyl 5-{5-[(5-chloropyridin-2-yl)sulfanyl]-2-cyclopropyl-1,3-oxazol-4-yl}pyridine-2-carboxylate To a solution of Intermediate 45 (2.2 g, 6.8 mmol) in NMP (65 mL) at rt was added 5-chloropyridine-2-thiol (1.19 g, 8.17 mmol) and K$_2$CO$_3$ (2.82 g, 20.4 mmol). The resulting solution was heated at 60° C. overnight. Upon completion of the reaction as judged by LC/MS analysis, the reaction was dilute with water, extract with EtOAc, the combined organic layers was washed with brine, dried over MgSO$_4$, filtered, concentrated and purified on silica gel to afford the title compound (2.54 g). LC/MS: m/e 387.9 (M+H)$^+$.

Example 88

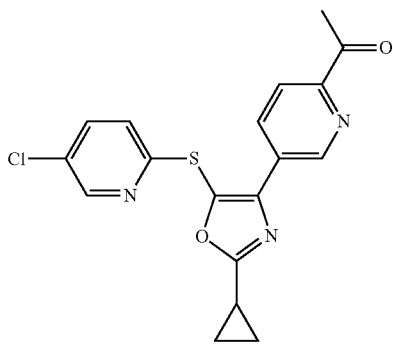 [SMILES: CC(=O)c1ccc(-c2nc(C3CC3)oc2Sc2ccc(Cl)cn2)cn1]

1-(5-{5-[(5-Chloropyridin-2-yl)sulfanyl]-2-cyclopropyl-1,3-oxazol-4-yl}pyridin-2-yl)ethanone To a solution of Intermediate 87 (2.54 g, 6.55 mmol) in THF (260 mL) at rt was added MeMgBr (3.0M/Et$_2$O, 21.8 mL, 65.5 mmol), the resulting mixture was stirred at rt for 2 h. Upon completion of the reaction as judged by TLC analysis, the reaction was quenched by addition of sat.NH$_4$Cl solution, extracted with EtOAc, the organic layer was washed with brine, dried over MgSO$_4$, filtered, concentrated and purified on silica gel to afford the title compound (188 mg). LC/MS: m/e 371.8 (M+H)$^+$.

Example 89

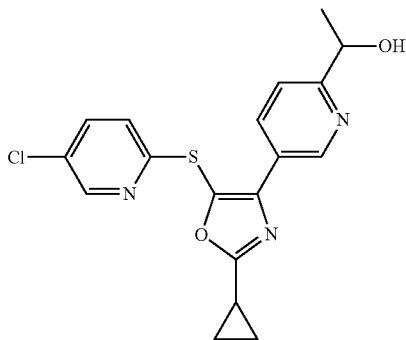 [SMILES: CC(O)c1ccc(-c2nc(C3CC3)oc2Sc2ccc(Cl)cn2)cn1]

1-(5-{5-[(5-Chloropyridin-2-yl)sulfanyl]-2-cyclopropyl-1,3-oxazol-4-yl}pyridin-2-yl)ethanol To a solution of Example 88 (16 mg, 0.04 mmol) in MeOH (10 mL) at rt was added NaBH$_4$ (1.6 mg, 0.04 mmol). The resulting solution was stirred at rt for 1 h. Upon completion of the reaction as judged by TLC analysis, the reaction was concentrated to dryness and purified on silica gel to afford the titled compound (12 mg). LC/MS: m/e 373.9 (M+H)$^+$.

Example 90

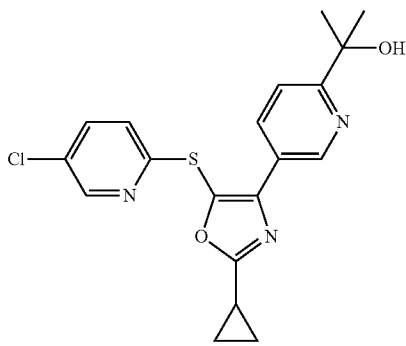 [SMILES: CC(C)(O)c1ccc(-c2nc(C3CC3)oc2Sc2ccc(Cl)cn2)cn1]

2-(5-{5-[(5-Chloropyridin-2-yl)sulfanyl]-2-cyclopropyl-1,3-oxazol-4-yl}pyridin-2-yl)propan-2-ol To a solution of Example 87 (2.54 g, 6.5 mmol) in THF (260 mL) at rt was added MeMgBr (3.0M/Et$_2$O, 21.8 mL, 65.5 mmol). The resulting mixture was stirred at rt for 2 h. Upon completion of the reaction as judged by TLC analysis, the reaction was quenched by addition of sat.NH$_4$Cl solution and extracted with EtOAc. The organic layer was washed with brine, dried over MgSO$_4$, filtered, concentrated and purified on silica gel to afford the title compound (1.77 g).

LC/MS: m/e 387.9 (M+H)+. 1H NMR (500 MHz, CDCl3): δ 1.22 (m, 4H), 1.56 (s, 6H), 2.19 (m, 1H), 4.85 (s, 1H), 6.96 (d, J=8.5 Hz, 1H), 7.42 (d, J=8 Hz, 1H), 7.55 (dd, J=2.5, 8.5 Hz, 1H), 8.32 (dd, J=2, 8.5 Hz, 1H), 8.43 (d, J=2.5 Hz, 1H), 9.14 (d, J=1.5 Hz, 1H).

The compounds in Table 8 were prepared from the appropriate starting materials using the procedure for Example 12.

TABLE 8

| Example | R₁ | R₃ | LCMS: found m/e (M + H) |
|---|---|---|---|
| 91 | 2-(5-methylpyridin-2-yl)propan-2-ol | 4-methoxyphenyl | 383.1 |
| 92 | 2-(5-methylpyridin-2-yl)propan-2-ol | 2,4-difluorophenyl | 388.3 |
| 93 | 2-(5-methylpyridin-2-yl)propan-2-ol | 4-chloro-3-fluorophenyl | 405.1 |
| 94 | 2-(5-methylpyridin-2-yl)propan-2-ol | 4-chloro-2-fluorophenyl | 405.1 |
| 95 | 2-(5-methylpyridin-2-yl)propan-2-ol | 5-chloropyrimidin-2-yl | 389.0 |

Example 96

2-(6-{5-[(5-Chloropyridin-2-yl)sulfanyl]-2-(4-fluorophenyl)-1,3-oxazol-4-yl}pyridazin-3-yl)propan-2-ol The target compound was prepared in an analogous manner to Example 12 except that Intermediate 12 was replaced with Intermediate 47. LC/MS: m/e 443.2 (M+H)+. 1H NMR (500 MHz, Acetone-d6): δ 1.64 (s, 6H), 4.70 (s, 1H), 7.38 (t, J=8.5 Hz, 2H), 7.43 (d, J=8.5 Hz, 1H), 7.76 (dd, J=2.5, 8.5 Hz, 1H), 8.09 (d, J=9 Hz, 1H), 8.22 (m, 2H), 8.27 (d, J=8.5 Hz, 1H), 8.43 (d, J=2.5 Hz, 1H).

Example 97

Ethyl 5-{5-[(5-chloropyridin-2-yl)sulfanyl]-2-(4-fluorophenyl)-1,3-oxazol-4-yl}isoxazole-3-carboxylate The target compound was prepared in an analogous manner to Example 78 except that Intermediate 29 was replaced with Intermediate 52. LC/MS: m/e 445.9 (M+H)⁺

Example 98

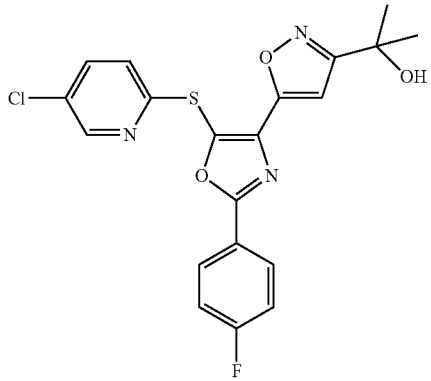 [SMILES: CC(C)(O)c1cc(-c2nc(-c3ccc(F)cc3)oc2Sc2ccc(Cl)cn2)on1]

2-(5-{5-[(5-Chloropyridin-2-yl)sulfanyl]-2-(4-fluorophenyl)-1,3-oxazol-4-yl}isoxazol-3-yl)propan-2-ol The title compound was prepared in an analogous manner to Example 80 starting with Example 97. LC/MS: m/e 431.9 (M+H)⁺

Example 99

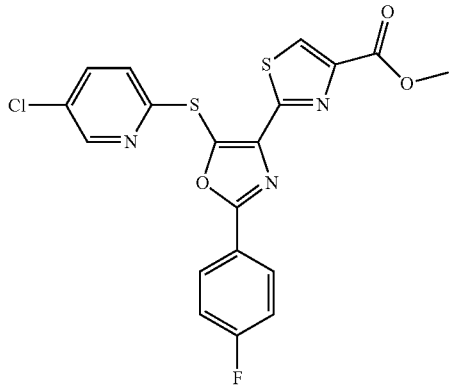 [SMILES: COC(=O)c1csc(-c2nc(-c3ccc(F)cc3)oc2Sc2ccc(Cl)cn2)n1]

Methyl 2-{5-[(5-chloropyridin-2-yl)sulfanyl]-2-(4-fluorophenyl)-1,3-oxazol-4-yl}-1,3-thiazole-4-carboxylate The target compound was prepared in an analogous manner to Example 78 except that Intermediate 29 was replaced with Intermediate 54. LC/MS: m/e 447.9 (M+H)⁺

Example 100

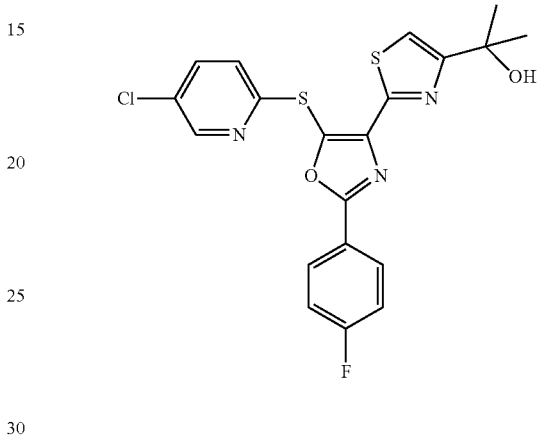

2-(2-{5-[(5-Chloropyridin-2-yl)sulfanyl]-2-(4-fluorophenyl)-1,3-oxazol-4-yl}-1,3-thiazol-4-yl)propan-2-ol The title compound was prepared in an analogous manner to Example 80 starting with Example 99. LC/MS: m/e 447.9 (M+H)⁺.

Example 101

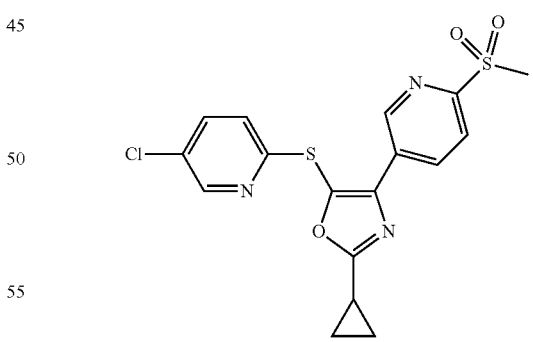

5-Chloro-2-({2-cyclopropyl-4-[6-(methylsulfonyl)pyridin-3-yl]-1,3-oxazol-5-yl}sulfanyl)pyridine The target compound was prepared in an analogous manner to Example 78 except that Intermediate 29 was replaced with Intermediate 66. LC/MS: m/e 407.8 (M+H)⁺. ¹H NMR (500 MHz, CDCl₃): δ 1.22 (m, 4H), 2.20 (m, 1H), 3.25 (s, 3H), 7.04 (d, J=8.5 Hz, 1H), 7.59 (dd, J=2.5, 8.5 Hz, 1H), 8.12 (d, J=8 Hz, 1H), 8.46 (d, J=2 Hz, 1H), 8.59 (dd, J=2, 8.5 Hz, 1H), 9.38 (s, 1H).

Example 102

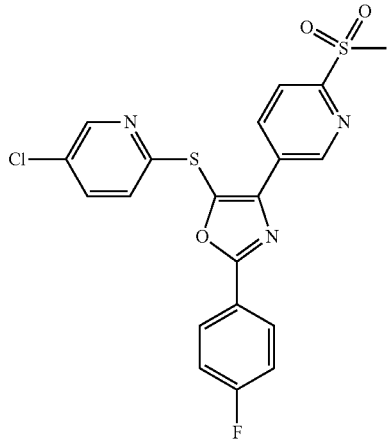 [SMILES: CS(=O)(=O)c1ccc(-c2nc(-c3ccc(F)cc3)oc2Sc2ccc(Cl)cn2)cn1]

5-Chloro-2-({2-(4-fluorophenyl)-4-[6-(methylsulfonyl)pyridin-3-yl]-1,3-oxazol-5-yl}sulfanyl)pyridine The target compound was prepared in an analogous manner to Example 78 except that Intermediate 29 was replaced with Intermediate 56. LC/MS: m/e 461.8 (M+H)+ NMR (500 MHz, CDCl₃): δ 3.28 (s, 3H), 7.14 (d, J=2.5 Hz, 1H), 7.24 (t, J=8.5 Hz, 2H), 7.60 (dd, J=2.5, 8.5 Hz, 1H), 8.18 (m, 3H), 8.40 (d, J=2.5 Hz, 1H), 8.72 (dd, J=2, 8 Hz, H), 9.49 (d, J=2 Hz, 1H).

The compounds in Table 9 were prepared from the appropriate starting materials using the procedure for Example 78.

TABLE 9

| Example | R₁ | R₂ | LCMS: found m/e (M + H) |
|---|---|---|---|
| 103 | methylsulfonyl-pyridin-2-yl | 5-fluoropyridin-3-yl | 462.7 |
| 104 | methylsulfonyl-pyridin-3-yl | 4-fluorophenyl | 461.7 |
| 105 | methylthio-pyridin-3-yl | 4-fluorophenyl | 429.8 |
| 106 A and 106B | methylsulfinyl-pyridin-3-yl | 4-fluorophenyl | 445.8 |

Note: Example 106 is racemic

Example 107

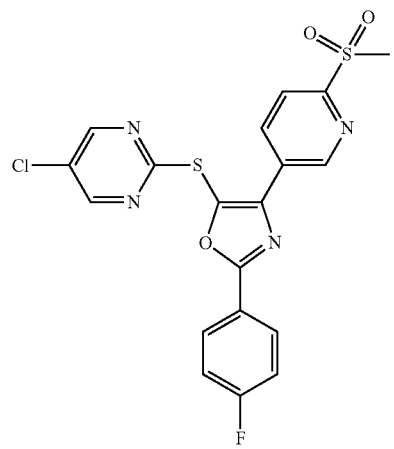 [SMILES: CS(=O)(=O)c1ccc(-c2nc(-c3ccc(F)cc3)oc2Sc2ncc(Cl)cn2)cn1]

113

5-Chloro-2-({2-(4-fluorophenyl)-4-[6-(methylsulfonyl)pyridin-3-yl]-1,3-oxazol-5-yl}sulfanyl)pyrimidine The target compound was prepared in an analogous manner to Example 78 except that Intermediate 56 was coupled with 5-chloropyrimidine-2-thiol. LC/MS: m/e 461.8 (M+H)$^+$ NMR (500 MHz, CDCl$_3$): δ 3.28 (s, 3H), 7.14 (d, J=2.5 Hz, 1H), 7.24 (t, J=8.5 Hz, 2H), 7.60 (dd, J=2.5, 8.5 Hz, 1H), 8.18 (m, 3H), 8.40 (d, J=2.5 Hz, 1H), 8.72 (dd, J=2, 8 Hz, 1H), 9.49 (d, J=2 Hz, 1H).

Example 108

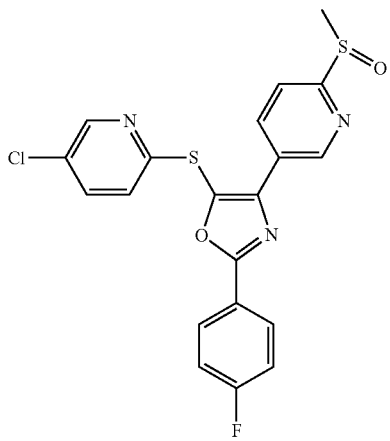 [SMILES: CS(=O)c1ccc(-c2nc(-c3ccc(F)cc3)oc2Sc2ccc(Cl)cn2)cn1]

(R)-5-Chloro-2-({2-(4-fluorophenyl)-4-[6-(methylsulfinyl)pyridin-3-yl]-1,3-oxazol-5-yl}sulfanyl)pyridine and (S)-5-Chloro-2-({2-(4-fluorophenyl)-4-[6-methylsulfinyl)pyridin-3-yl]-1,3-oxazol-5-yl}sulfanyl)pyridine The target compound was prepared in an analogous manner to Example 78 except that Intermediate 29 was replaced with Intermediate 60. LC/MS: m/e 445.8 (M+11)$^+$

Example 109

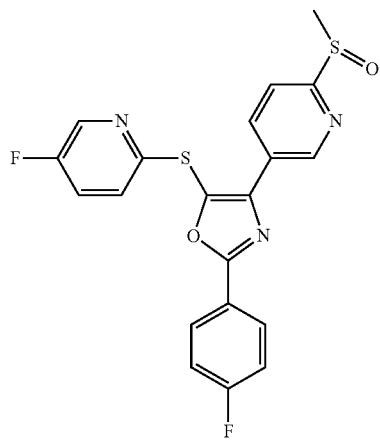 [SMILES: CS(=O)c1ccc(-c2nc(-c3ccc(F)cc3)oc2Sc2ccc(F)cn2)cn1]

114

(R)-5-Fluoro-2-({2-(4-fluorophenyl)-4-[6-(methylsulfinyl)pyridin-3-yl]-1,3-oxazol-5-yl}sulfanyl)pyridine and (S)-5-Fluoro-2-({2-(4-fluorophenyl)-4-[6-(methylsulfinyl)pyridin-3-yl]-1,3-oxazol-5-yl}sulfanyl)pyridine The target compound was prepared in an analogous manner to Example 108 starting with Intermediate 60 and replacing 5-chloropyridine-2-thiol with 5-fluoropyridine-2-thiol. LC/MS: m/e 445.8 (M+H)$^+$

Example 110

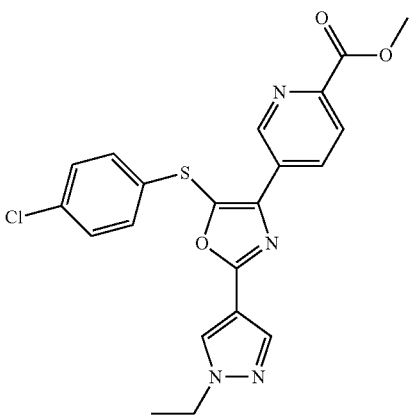 [SMILES: CCn1cc(-c2nc(-c3ccc(C(=O)OC)nc3)c(Sc3ccc(Cl)cc3)o2)cn1]

Methyl 5-(5-[(4-chlorophenyl)sulfanyl]-2-(1-ethyl-1H-pyrazol-4-yl)-1,3-oxazol-4-yl)pyridine-2-carboxylate The title compound was prepared in an analogous manner to Example 12 starting with Intermediate 61. LC/MS: m/e 441.2 (M+H)$^+$.

Example 111

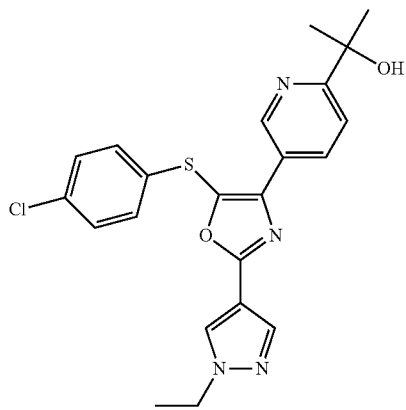 [SMILES: CCn1cc(-c2nc(-c3ccc(C(C)(C)O)nc3)c(Sc3ccc(Cl)cc3)o2)cn1]

2-(5-{5-[(4-chlorophenyl)sulfanyl]-2-(1-ethyl-1H-pyrazol-4-yl)-1,3-oxazol-4-yl)pyridin-2-yl}propan-2-ol The title compound was prepared in an analogous manner to Example 80 starting with Example 110. LC/MS: m/e 441.3 (M+H)⁺.

Example 112

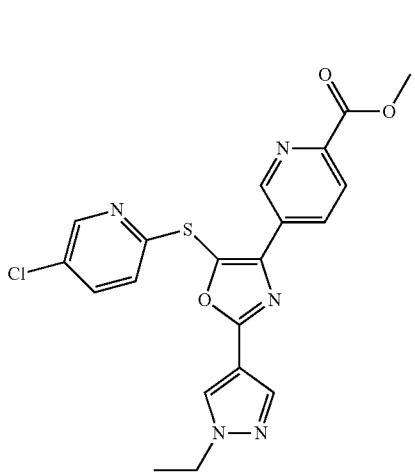

Methyl 5-{5-[(5-chloropyridin-2-yl)sulfanyl]-2-(1-ethyl-1H-pyrazol-4-yl)-1,3-oxazol-4-yl)pyridin-2-carboxylate The title compound was prepared in an analogous manner to Example 12 starting with Intermediate 64 and 4-Chlorobenzenethiol was replaced with 5-chloropyridine-2-thiol. LC/MS: m/e 441.9 (M+H)⁺.

Example 113

2-(5-{5-[(5-chloropyridin-2-yl)sulfanyl]-2-(1-ethyl-1H-pyrazol-4-yl)-1,3-oxazol-4-yl pyridin-2-yl}propan-2-ol The title compound was prepared in an analogous manner to Example 80 starting with Example 112. LC/MS: m/e 442.1 (M+H)⁺.

Example 114

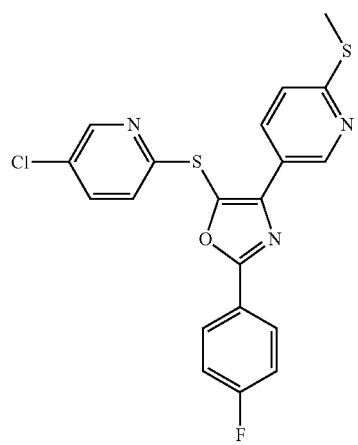

5-Chloro-2-({2-(4-fluorophenyl)-4-[6-(methylsulfanyl)pyridin-3-yl]-1,3-oxazol-5-yl}sulfanyl)pyridine The target compound was prepared in an analogues manner to Example 78 except that Intermediate 29 was replaced with Intermediate 58. LC/MS: m/e 429.8 (M+H)⁺. NMR (500 MHz, CDCl₃): δ 2.62 (s, 3H), 7.02 (d, J=8.5 Hz, 1H), 7.22 (t, J=8.5 Hz, 2H), 7.26 (d, J=8.5 Hz, 1H), 7.55 (dd, J=2.5, 8.5 Hz, 1H), 8.17 (m, 2H), 8.24 (dd, J=2.5, 8.5 Hz, 1H), 8.42 (d, J=2.5 Hz, 1H), 9.20 (s, 1H).

Example 115

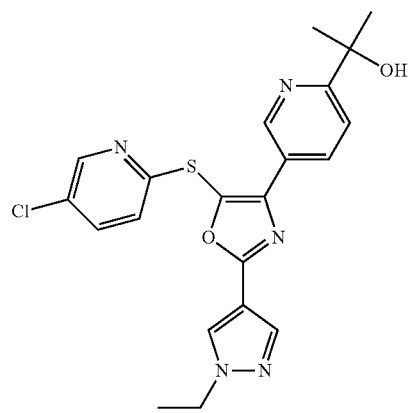 [SMILES: CCn1cc(-c2nc(-c3ccc(C(C)(C)O)nc3)c(Sc3ccc(Cl)cn3)o2)cn1]

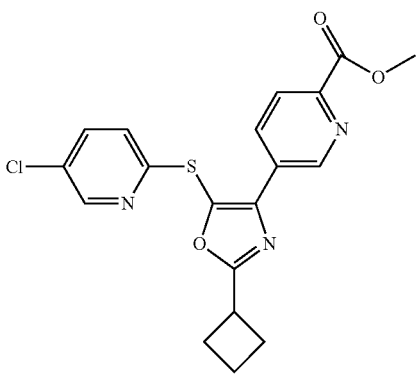 [SMILES: COC(=O)c1ccc(-c2nc(C3CCC3)oc2Sc2ccc(Cl)cn2)cn1]

Methyl 5-{5-[(5-chloropyridin-2-yl)sulfanyl]-2-cyclobutyl-1,3-oxazol-4-yl}pyridine-2-carboxylate The target compound was prepared in an analogous manner to Example 87 except that Intermediate 45 replaced Intermediate 69. LC/MS: m/e 401.9 (M+H)+

Example 116A and Example 116B

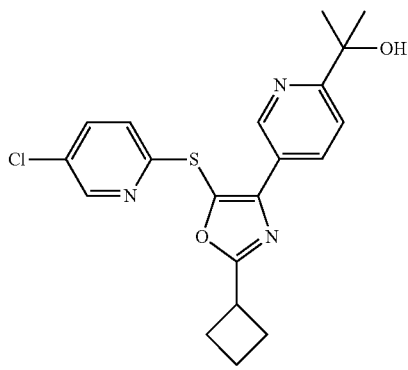 [SMILES: CC(C)(O)c1ccc(-c2nc(C3CCC3)oc2Sc2ccc(Cl)cn2)cn1]

2-(5-{5-[(5-Chloropyridin-2-yl)sulfanyl]-2-cyclobutyl-1,3-oxazol-4-yl}pyridin-2-yl)propan-2-ol

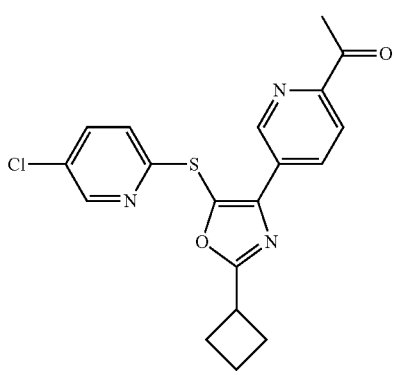 [SMILES: CC(=O)c1ccc(-c2nc(C3CCC3)oc2Sc2ccc(Cl)cn2)cn1]

1-(5-{5-[(5-Chloropyridin-2-yl)sulfanyl]-2-cyclobutyl-1,3-oxazol-4-yl}pyridin-2-yl)ethanone To a solution of Example 115 (264 mg, 0.6 mmol) in THF (20 ml) at rt was added MeMgBr (3.0M/Et$_2$O, 2.19 mL, 6.6 mmol) and the resulting mixture was stirred at rt for 2 h. Upon completion of the reaction as judged by TLC analysis, the reaction was quenched by addition of sat.NH$_4$Cl solution, extracted with EtOAc, the organic layer was washed with brine, dried over MgSO$_4$, filtered, concentrated and purified on silica gel to afford the title compound (201 mg) along with methyl ketone as a byproduct.

For 116A: LC/MS: m/e 401.9 (M+H)+. $^1$H NMR (500 MHz, CDCl$_3$): δ 1.57 (s, 6H), 2.12 (m, 2H), 2.51 (m, 4H), 3.76 (m, 1H), 4.88 (s, 1H), 6.97 (d, J=8.5 Hz, 1H), 7.43 (d, J=8.5 Hz, 1H), 7.56 (dd, J=3.0, 8.5 Hz, 1H), 8.34 (dd, J=2.5, 8.5 Hz, 1H), 8.42 (d, J=2.5 Hz, 1H), 9.16 (d, J=1.5 Hz, 1H).

For 116B: m/e 385.9 (M+H)+. $^1$H NMR (500 MHz, CDCl$_3$): δ 2.10 (m, 2H), 2.51 (m, 4H), 2.74 (s, 3H), 3.77 (m, 1H), 4.90 (s, 1H), 7.02 (d, J=8.5 Hz, 1H), 7.56 (d, J=7.0 Hz, 1H), 8.10 (d, J=8.5 Hz, 1H), 8.41 (s, 1H), 8.50 (d, J=8.0 Hz, 1H), 9.32 (s, 1H).

Example 117

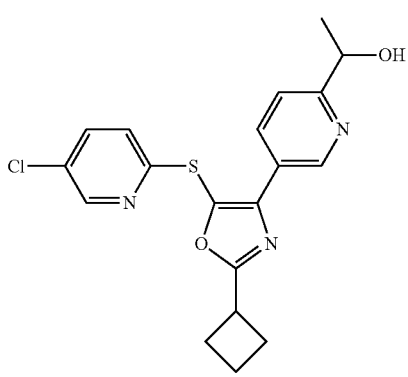 [SMILES: CC(O)c1ccc(-c2nc(C3CCC3)oc2Sc2ccc(Cl)cn2)cn1]

(R)-1-(5-{5-[(5-Chloropyridin-2-yl)sulfanyl]-2-cyclobutyl-1,3-oxazol-4-yl}pyridin-2-yl)ethanol and (S)-1-(5-{5-[(5-Chloropyridin-2-yl)sulfanyl]-2-cyclobutyl-1,3-oxazol-4-yl}pyridin-2-yl)ethanol The target compound was prepared in an analogous manner to Example 89 except that Example 88 was replaced with Example 116B. LC/MS: m/e 387.9 (M+H)+. $^1$H NMR (500 MHz, CDCl$_3$): δ 1.52 (d, J=6.5 Hz, 3H), 2.08 (m, 2H), 2.50 (m, 4H), 3.75 (m, 1H), 4.13 (br, 1H), 4.93 (m, 1H), 6.95 (d, J=9 Hz, 1H), 7.33 (d, J=8 Hz, 1H), 7.54 (dd, J=2.5, 8.5 Hz, 1H), 8.33 (dd, J=2.0, 8.0 Hz, 1 Hz), 8.40 (d, J=2 Hz, 1H), 8.18 (d, J=1.5 Hz, 1H).

Example 118

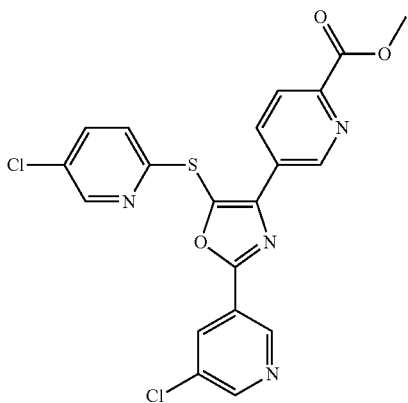 [SMILES: COC(=O)c1ccc(-c2nc(-c3cncc(Cl)c3)oc2Sc2ccc(Cl)cn2)cn1]

Methyl 5-{2-(5-chloropyridin-3-yl)-5-[(5-chloropyridin-2-yl)sulfanyl]-1,3-oxazol-4-yl}pyridine-2-carboxylate The target compound was prepared in an analogous manner to Example 78 except that Intermediate 29 was replaced with Intermediate 72. LC/MS: mile 458.8 (M+H)+.

Example 119

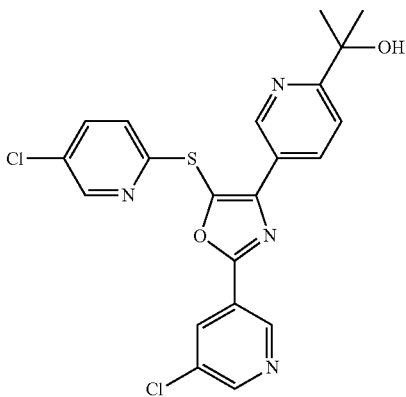 [SMILES: CC(C)(O)c1ccc(-c2nc(-c3cncc(Cl)c3)oc2Sc2ccc(Cl)cn2)cn1]

2-(5-{2-(5-Chloropyridin-3-yl)-5-[(5-chloropyridin-2-yl)sulfanyl]-1,3-oxazol-4-yl}pyridin-2-yl)propan-2-ol The title compound was prepared in an analogous manner to Example 80 starting with Example 118. LC/MS: m/e 458.8 (M+H)+. $^1$H NMR (500 MHz, CDCl$_3$): δ 1.60 (s, 6H), 4.81 (s, 1H), 7.13 (d, J=8.5 Hz, 1H), 7.49 (d, J=8.0 Hz, 1H), 7.60 (dd, J=2.5, 8.5 Hz, 1H), 8.44 (m, 3H), 8.74 (d, J=2.5 Hz, 1H), 9.27 (dd, J=2.0, 6.5 Hz, 2H).

Example 120

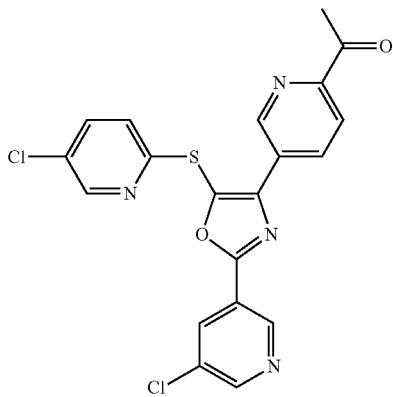 [SMILES: CC(=O)c1ccc(-c2nc(-c3cncc(Cl)c3)oc2Sc2ccc(Cl)cn2)cn1]

1-(5-{2-(5-Chloropyridin-3-yl)-5-[(5-chloropyridin-2-yl)sulfanyl]-1,3-oxazol-4-yl}pyridin-2-yl)ethanone The target compound was prepared in an analogous manner to Example 116 B starting with Example 118. LC/MS: m/e 442.8 (M+H)+. $^1$H NMR (500 MHz, CDCl$_3$): δ 2.77 (s, 3H), 7.17 (d, J=8.0 Hz, 1H), 7.61 (d, J=7.5 Hz, 1H), 8.14 (d, J=7.5 Hz, 1H), 8.39 (s, 1H), 8.44 (s, 1H), 8.58 (d, J=7.5 Hz, 1H), 8.75 (s, 1H), 9.28 (s, 1H), 9.45 (s, 1H).

Example 121

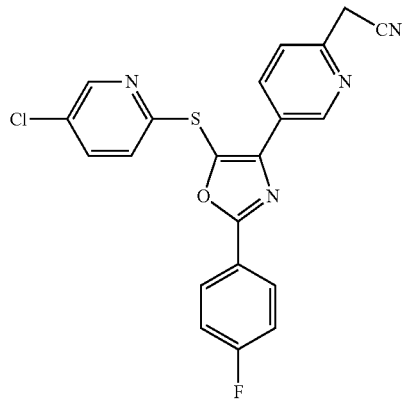 [SMILES: N#CCc1ccc(-c2nc(-c3ccc(F)cc3)oc2Sc2ccc(Cl)cn2)cn1]

(5-{5-[(5-Chloropyridin-2-yl)sulfanyl]-2-(4-fluorophenyl)-1,3-oxazol-4-yl}pyridin-2-yl)acetonitrile The target compound was prepared in an analogous manner to Example 78 except that Intermediate 29 was replaced with Intermediate 74. LC/MS: m/e 422.8 (M+H)+. $^1$H NMR (500 MHz, CDCl$_3$): δ 4.00 (s, 3H), 7.08 (d, J=9.0 Hz, 1H), 7.23 (t, J=8.5 Hz, 2H), 7.53 (d, J=8.5 Hz, 1H), 7.57 (dd, J=2.5, 8.0 Hz, 1H), 8.19 (m, 2H), 8.41 (d, J=2.5 Hz, 1H), 8.49 (dd, J=2.0, 8.0 Hz, 1H), 9.33 (d, J=2.5 Hz 1H).

Example 122

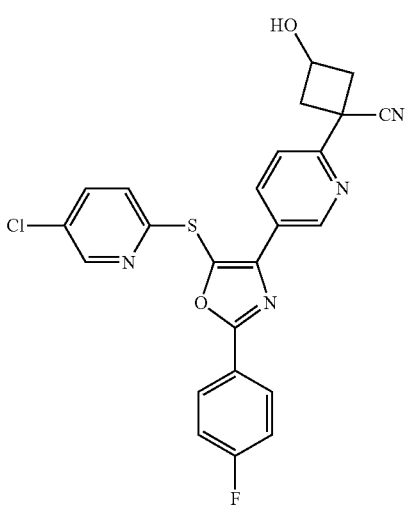 [SMILES: N#CC1(c2ccc(-c3nc(-c4ccc(F)cc4)oc3Sc3ccc(Cl)cn3)cn2)CC(O)C1]

1-(5-{5-[(5-Chloropyridin-2-yl)sulfanyl]-2-(4-fluorophenyl)-1,3-oxazol-4-yl}pyridin-2-yl-3-hydroxycyclobutanecarbonitrile The target compound was prepared in an analogous manner to Example 78 except that Intermediate 29 was replaced with Intermediate 76. LC/MS: m/e 478.9 (M+H)⁺. ¹H NMR (500 MHz, Acetone-d6): δ 1.68 (m, 1H), 2.01 (m, 1H), 2.33 (m, 1H), 3.73 (m, 1H), 4.03 (m, 1H), 7.40 (m, 3H), 7.80 (m, 2H), 8.24 (m, 2H), 8.46 (d, J=2.5 Hz, 1H), 8.52 (dd, J=2.5, 8.5 Hz, 1H), 9.18 (s, 1H).

Example 123

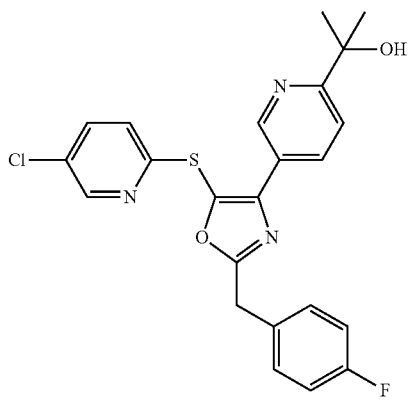 [SMILES: CC(C)(O)c1ccc(-c2nc(Cc3ccc(F)cc3)oc2Sc2ccc(Cl)cn2)cn1]

2-(5-{5-[(5-Chloropyridin-2-yl)sulfanyl]-2-(4-fluorobenzyl)-1,3-oxazol-4-yl}pyridin-2-yl)propan-2-ol The target compound was prepared in an analogous manner to Example 78 except that Intermediate 29 was replaced with Intermediate 78. LC/MS: m/e 456.0 (M+H)⁺. ¹H NMR (500 MHz, Acetone-d6): δ 1.51 (m, 1H), 4.31 (s, 2H), 4.59 (s, 1H), 7.15 (t, J=8.5 Hz, 2H), 7.23 (d, J=8.5 Hz, 1H), 7.47 (m, 2H), 7.50 (d, J=8.5 Hz, 1H), 7.79 (dd, J=2.5, 8.5 Hz, 1H), 8.33 (dd, J=2.5, 8.5 Hz, 1H), 8.44 (d, J=2.5 Hz, 1H), 9.10 (d, J=2.0 Hz, 1H).

Example 124

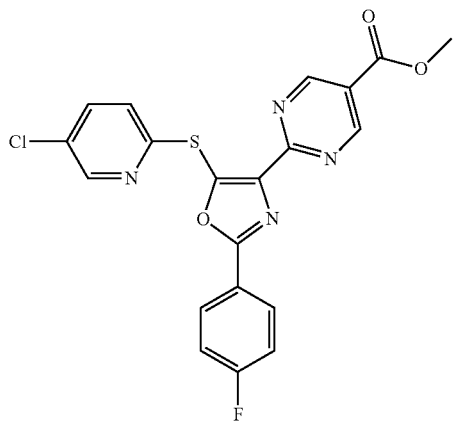 [SMILES: COC(=O)c1cnc(-c2nc(-c3ccc(F)cc3)oc2Sc2ccc(Cl)cn2)nc1]

Methyl 2-{5-[(5-chloropyridin-2-yl)sulfanyl]-2-(4-fluorophenol)-1,3-oxazol-4-yl}pyrimidine-5-carboxylate The target compound was prepared in an analogous manner to Example 78 except that Intermediate 29 was replaced with Intermediate 80. LC/MS: m/e 442.9 (M+H)⁺. ¹H NMR (500 MHz, CDCl₃): δ 4.02 (s, 3H), 7.20 (t, J=8.5 Hz, 2H), 7.27 (m, 1H), 7.60 (dd, J=2.5, 8.5 Hz, 1H), 8.19 (m, 2H), 8.44 (d, J=2.5 Hz, 1H), 9.39 (s, 2H).

The Examples in Table 10 were prepared following the procedures described in Example 50, Step F.

TABLE 10

| Example | R₃ | LCMS: found m/e (M + H) |
|---|---|---|
| 125 | 5-fluoropyridin-2-yl | 409.2 |
| 126 | 4-chloro-2-fluorophenyl | 442.1 |
| 127 | 4-chloro-3-fluorophenyl | 442.1 |
| 128 | 5-methoxypyridin-2-yl | 421.2 |
| 129 | 2,4-difluorophenyl | 426.1 |
| 130 | 3,4-difluorophenyl | 426.1 |
| 131 | 5-chloropyrimidin-2-yl | 426.1 |
| 132 | 4-methoxyphenyl | 420.2 |

Example 133

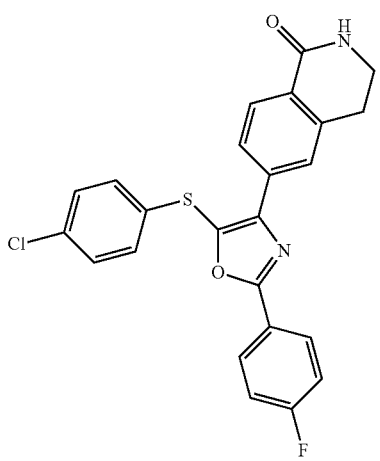 [SMILES: O=C1NCCc2cc(-c3nc(-c4ccc(F)cc4)oc3Sc3ccc(Cl)cc3)ccc21]

6-{5-[(4-Chlorophenyl)sulfanyl]-2-(4-fluorophenyl)-1,3-oxazol-4-yl}-3,4-dihydroisoquinolin-1(2H)-one The title compound was prepared in an analogous manner to Example 12 starting with Intermediate 82. LC/MS: m/e 451.2 (M+H)$^+$.

Example 134

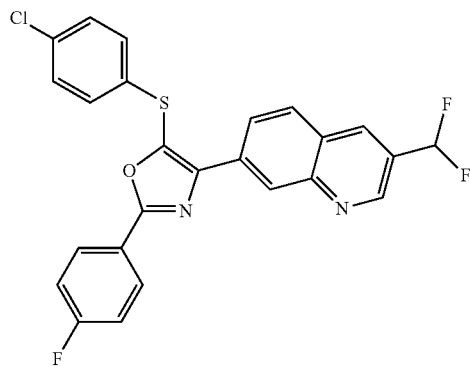 [SMILES: Fc1ccc(-c2nc(-c3ccc4cc(C(F)F)cnc4c3)c(Sc3ccc(Cl)cc3)o2)cc1]

7-{5-[(4-Chlorophenyl)sulfanyl]-2-(4-fluorophenyl)-1,3-oxazol-4-yl}-3-(difluoromethyl)quinoline Intermediate 86 was dissolved 4-chlorothiophenol (23 mg, 0.157 mmol) in NMP (1 mL) and added a 60% oil dispersion of NaH (6.3 mg, 0.157 mmol). Vigorous gas evolution and reaction mixture became dark purple in color. Stirred at rt for 20 min. then combined a solution of intermediate (36 mg, 0.071 mmol) in NMP (1 mL), the above prepared thiolate solution and CuI (13.6 mg, 0.071 mmol) in a sealed vial, degassed with N$_2$, sealed with a Teflon stopper and heated to 120° C. Heated for 7 h then cooled to rt and stirred overnight. Diluted with sat'd. NaHCO$_3$ (9 mL) and conc NH$_3$ (1 mL) and extracted with EtOAc (3×). Washed extracts with brine (1×), dried over MgSO$_4$, filtered, evaporated and dried under high vac. at rt. The amber oil was purified by prep TLC (SiO$_2$, 20×20 cm, 1000 microns, 3 plates; hexane-EtOAc, 3:1) to afford the title compound (26 mg). LC/MS: m/e 482.9 (M+H)$^+$. $^1$H NMR (500 MHz, CDCl$_3$) δ 6.94 (t, J=55.85 Hz, 1H), 7.24 (t, J=8.55 Hz, 2H), 7.3 (m, 4H), 8.01 (d, J=8.5 Hz, 1H), 8.22 (m, 2H), 8.36 (s, 1H), 8.52 (d, J=8.5 Hz, 1H), 9.06 (s, 1H), 9.1 (s, 1H).

Example 135

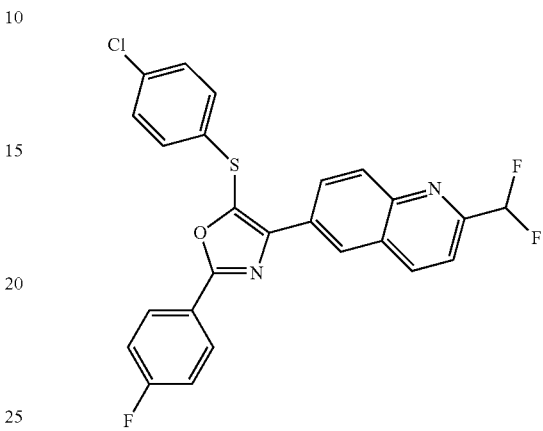

6-{5-[(4-Chlorophenyl)sulfanyl]-2-(4-fluorophenyl)-1,3-oxazol-4-yl}-2-(difluoromethyl)quinoline The title compound was prepared in an analogous manner to Example 12 starting with Intermediate 90. LC/MS: m/e 483.1 (M+H)$^+$. $^1$H NMR (500 MHz, CDCl$_3$) δ 6.84 (t, J=55.35, 1H), 7.25 (t, J=8.6 Hz, 2H), 7.3 (m, 4H), 7.8 (d, J=8.5 Hz, 1H), 8.22 (m, 3H), 8.42 (d, J=8.7 Hz, 1H), 8.69 (dd, J=1.8, 8.9 Hz, 1H), 8.72 (s, 1H).

Example 136

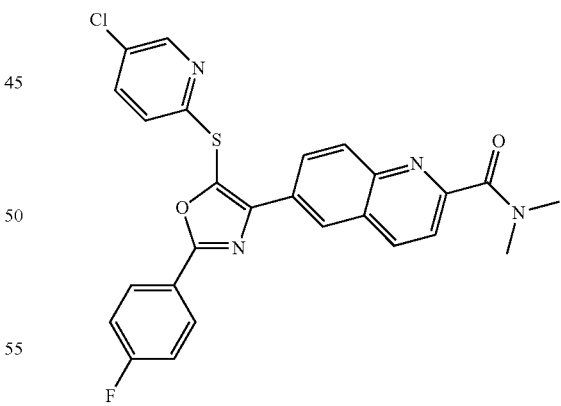

6-{5-[(5-Chloropyridin-2-yl)sulfanyl]-2-(4-fluorophenyl)-1,3-oxazol-4-yl}-N,N-dimethylquinoline-2-carboxamide The target compound was prepared in an analogous manner to Example 12 starting with Intermediate 93. LC/MS: m/e 505.1 (M+H)$^+$. $^1$H NMR (500 MHz, CDCl3) δ 3.21 (s, 3H), 3.24 (s, 3H), 7.085 (d, J=8.7 Hz, 1H), 7.25 (t, J=8.2 Hz, 2H), 7.56 (d, J=9.1 Hz, 1H), 7.77 (d, J=8.3 Hz, 1H), 8.19 (d, J=8.4 Hz, 1H), 8.24 (m, 2H), 8.35 (d, J=8.8 Hz, 1H), 8.45 (s, 1H), 8.6 (d, J=9.2 Hz, 1H), 8.69 (s, 1H).

Example 137

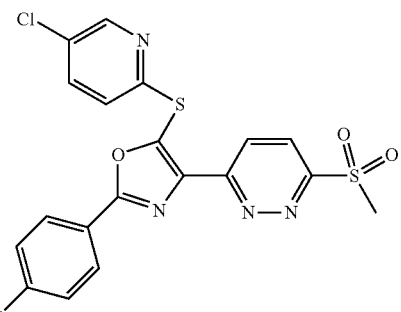

3-{5-[(5-Chloropyridin-2-yl)sulfanyl]-2-(4-fluorophenyl)-1,3-oxazol-4-yl}-6-(methylsulfonyl)pyridazine The target compound was prepared in an analogous manner to the Example 12 starting with Intermediate 97. LC/MS: m/e 462.8 (M+H)+. 1H NMR (500 MHz, CDCl3) δ 3.50 (s, 3H), 7.23 (m, 2H), 7.33 (d, J=8.7 Hz, 1H), 7.63 (dd, J=2.1, 8.5 Hz, 1H), 8.15 (m, 2H), 8.3 (d, J=8.8 Hz, 1H), 8.42 (s, 1H), 8.58 (t, J=8.7 Hz, 1H).

Example 138

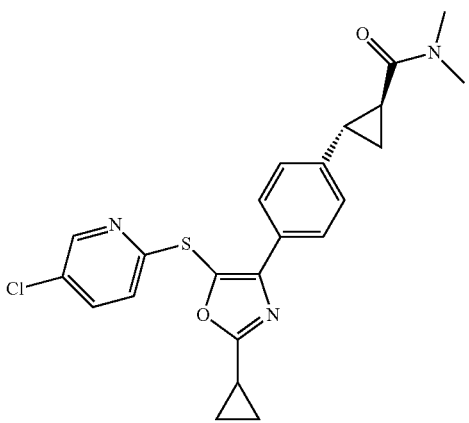 [SMILES: CN(C)C(=O)[C@H]1C[C@@H]1c1ccc(-c2nc(C3CC3)oc2Sc2ccc(Cl)cn2)cc1]

(1S,2S)-2-(4-{5-[(5-chloropyridin-2-yl)thio]-2-cyclopropyl-1,3-oxazol-4-yl}phenyl-N,N-dimethylcyclopropanecarbozamide Step A A solution of Intermediate 24 (478 mg, 1.858 mmol), PdCl2 (dppf)-CH2Cl2 Adduct (68 mg, 0.093 mmol), dppf (51 mg, 0.093 mmol), KOAc (oven dried) (547 mg, 5.57 mmol), bis(pinacolato)diboron (613 mg, 2.415 mmol) in dioxane (4.3 mL) was placed under an atmosphere of nitrogen and heated at 150° C. for 20 min via microwave irradiation. To this mixture was added Intermediate 98 (500 mg, 1.858 mmol), bis(triphenylphosphine)palladium (II) chloride (130 mg, 0.186 mmol), sodium carbonate (1 mL of 1 M aqueous solution). The mixture was heated at 150° C. for 45 min via microwave irradiation. Water was added and the mixture was extracted with ethyl acetate. The organics were dried (MgSO4) and concentrated. The residue was subject to silica column (0-30% EtOAc in hexanes) to afford ethyl (1S,2S)-2-[4-(2-cyclopropyl-1,3-oxazol-4-yl)phenyl]cyclopropanecarboxylate (239 mg, 43%). LC/MS: m/z 298.1 (M+H)+.

Step B

A solution of the product from the previous step (400 mg, 1.345 mmol) and NBS (311 mg, 1.749 mmol) in CH2Cl2 (4.5 mL) was stirred at rt for 3 h. Upon completion of the reaction, the solution was diluted with sat aq NaS2O3 solution. The organic layer was removed, dried over MgSO4, filtered and concentrated giving rise to an oil. The oil was purified on silica gel to afford the ethyl (1S,2S)-2-[4-(5-bromo-2-cyclopropyl-1,3-oxazol-4-yl)phenyl]cyclopropanecarboxylate (335 mg, 66%). LC/MS: m/z 376.2 (M+H)+.

Step C

A solution of 5-chloropyridine-2-thiol (201 mg, 1.382 mmol) dissolved in 2 mL of NMP was treated with NaH (55 mg, 1.382 mmol). The resulting solution was stirred for 30 min at rt before the product from the previous step (260 mg, 0.691 mmol) and CuI (132 mg, 0.691 mmol) were added. The resulting dark solution was heated to 120° C. for 16 h. After which point, the solution was poured into a rapidly stirred solution of 9:1 NH4Cl:NH4OH and EtOAc. Upon clarification of the organic layer, removal of the organic layer was followed by drying over MgSO4, filtration and concentration giving rise to an oil. The oil was purified on silica gel to afford ethyl (1S,2S)-2-(4-{5-[(5-chloropyridin-2-yl)thio]-2-cyclopropyl-1,3-oxazol-4-yl}phenyl)cyclopropanecarboxylate. LC/MS: m/z 441.1 (M+H)+.

Step D

The product from the previous step (140 mg, 0.318 mmol) was dissolved in 1 mL of acetonitrile, to which was added 1 mL of water, followed by excess KOH pellets. The reaction was stirred at 80° C. for 3 h. After it was cooled to rt, the pH of the reaction mixture was adjusted to 6 with concentrated HCl. EtOAc was added, and the mixture was washed with water and brine, dried, and concentrated to dryness to afford (1S,2S)-2-(4-({5-[(5-chloropyridin-2-yl)thio]-2-cyclopropyl-1,3-oxazol-4-yl}phenyl)cyclopropanecarboxylic acid which was used in the next step with out further purification. LC/MS: m/z 413.1 (M+H)+.

Step E

The product from the previous step (30 mg, 0.073 mmol), HOBT (28 mg, 0.182 mmol), and EDC (35 mg, 0.182 mmol) were dissolved in 1 ml of DMF, to which were added Hunig's base (0.075 mL, 0.436 mmol) and dimethyl amine (2 M THF solution, 0.363 mL, 0.727 mmol). The reaction was heated at 75° C. for 45 min. Upon cooling to rt, the reaction was diluted with EtOAc and the reaction mixture was washed with water and brine, dried, and concentrated to dryness. The title compound was crystallized by dissolving in hot methanol then slowly cooling to −20° C. LC/MS: m/z 440.1 (M+H)+. 1H NMR (500 MHz, CD3OD): δ 8.39 (s, 1H), 7.84 (d, 2H), 7.71

(d, 1H), 7.20 (d, 2H), 7.06 (d, 1H), 3.16 (s, 3H), 2.97 (s, 3H), 4.22 (m, 1H), 2.4-2.2 (br, 2H), 1.6-1.1 (br, 2H).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A method for treating a FAAH-mediated disease selected from the group consisting of osteoarthritis and pain, in a warm-blooded animal selected from the group consisting of a mouse, a rat, a horse, cattle, a sheep, a dog, and a cat, comprising administering to the warm-blooded animal an effective amount of a compound of Formula I

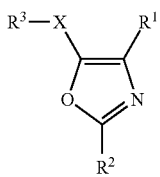

or a pharmaceutically acceptable salt thereof wherein:
X is S or SO;
n is 0, 1 or 2;
$R^1$ is selected from the group consisting of:
(1) aryl, and
(2) $HET^1$, wherein $R^1$ is optionally mono or di-substituted with substituents $R^4$ and $R^5$; and wherein $R^4$ and $R^5$ are independently selected from the group consisting of:
(a) halo,
(b) —CN,
(c) mono, di or tri-halo $C_{1-4}$ alkyl,
(d) mono, di or tri-halo $OC_{1-4}$ alkyl,
(d) —$OC_{1-4}$ alkyl, optionally substituted with hydroxyl, halo or amino,
(e) —$C_{1-4}$alkyl optionally substituted with one or two substituents selected from hydroxyl, CN, —$CHF_2$ and —$CF_3$,
(f) —$C_{1-2}$alkyl-$C_{3-6}$cycloalkyl optionally substituted with hydroxy, halo or CN,
(g) —$S(O)_nC_{1-4}$alkyl,
(h) —$S(O)_nNR^6R^7$,
(i) —C(O)—NH—$NR^8R^9$,
(j) —C(O)—OH,
(k) —C(O)—$OC_{1-4}$alkyl, optionally substituted with halo or hydroxy,
(l) —C(O)—$NR^{10}R^{11}$,
(m) —C(O)—$C_{1-4}$alkyl optionally mono, di or tri substituted with halo,
(o) —$C(NR^{12})$—$NR^{13}R^{14}$,
(p) $HET^4$,
(q) aryl,
(r) —C(O)—NH—NH—C(O)H,
(s) —$CH_2$—C(O)—O—$C_{1-4}$alkyl, whereas the $CH_2$ may be optionally substituted with $C_{1-4}$-alkyl or OH (t) —CH$_2$—C(O)NR$^{15}$R$^{16}$, whereas the CH$_2$ may be optionally substituted with C$_{1-4}$-alkyl or OH, and
(u) —NR$^{17}$R$^{18}$,
wherein choices (p) and (q) are each optionally mono or di-substituted with substituents selected from
(1) halo,
(2) —CN,
(3) —OH,
(4) —C$_{1-4}$alkyl optionally substituted with hydroxy, halo or cyano,
(5) —CF$_3$,
(6) —OC$_{1-4}$alkyl optionally substituted with hydroxyl or halo,
(7) —C(O)OH, and
(8) —C(O)O—C$_{1-3}$ alkyl;
(9) —C(O)—NR$^{19}$R$^{20}$,
(10) —NH$_2$,
(11) Oxo,
(12) =S,
with the proviso that the substituent on choice (q) is other than oxo or =S,
wherein R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$ and R$^{20}$, are each independently selected from H and C$_{1-4}$alkyl, or
R$^6$ and R$^7$ or R$^8$ and R$^9$ or R$^{10}$ and R$^{11}$ or R$^{13}$ and R$^{14}$ or R$^{15}$ and R$^{16}$ or R$^{17}$ and R$^{18}$ or R$^{19}$ and R$^{20}$ are joined together to form a ring with the atoms to which they are attached there is formed a 5-membered heterocyclic ring of 4 to 7 atoms, said ring containing 1, 2, 3 or 4 heteroatoms selected from N, O and S, said ring being optionally mono or di-substituted with substituents independently selected from halo, hydroxyl, oxo, C$_{1-4}$alkyl, hydroxyC$_{1-4}$alkyl, haloC$_{1-4}$alkyl, —C(O)—C$_{1-4}$alkyl and —S(O)$_n$C$_{1-4}$alkyl;
R$^2$ is selected from the group consisting of:
(1) aryl,
(2) HET$^3$,
(3) —CH$_2$-aryl,
(4) —CH$_2$-HET$^3$, and
(5) —C$_{3-6}$cycloalkyl,
wherein R$^2$ is optionally mono or di-substituted with substituents independently selected from the group consisting of
(a) halo,
(b) —CN,
(c) —OH,
(d) —C$_{1-4}$alkyl optionally substituted with hydroxy, halo or cyano,
(e) —CF$_3$,
(f) —OC$_{1-4}$alkyl optionally substituted with hydroxyl or halo,
(g) —C(O)O—C$_{1-3}$ alkyl and
(h) —S-aryl, optionally substituted with halo, C$_{1-4}$alkyl or —OC$_{1-4}$alkyl;
R$^3$ is selected from the group consisting of
(1) HET$^5$, and
(2) C$_{3-6}$cycloalkyl,
wherein R$^3$ is optionally mono or di-substituted with substituents independently selected from the group consisting of
(a) hydroxy,
(b) halo,
(c) —C$_{3-6}$cycloalkyl,
(d) —OC$_{3-5}$cycloalkyl,
(e) —OC$_{1-4}$alkyl,
(f) —C(O)CH$_3$
(g) mono, di or tri-halo C$_{1-4}$ alkyl,
(h) mono, di or tri-halo —OC$_{1-4}$ alkyl, and
(i) —S(O)$_n$—C$_{1-4}$ alkyl;
wherein HET$^1$, HET$^2$, HET$^3$, HET$^4$ and HET$^5$ are each independently a 5 to 10-membered aromatic, partially aromatic or non-aromatic mono- or bicyclic ring, or N-oxide thereof, said containing 1 to 4 heteroatoms selected from O, S and N, and optionally substituted with 1 to 2 oxo groups.

2. The method of claim 1
wherein:
R$^1$ is selected from the group consisting of:
(1) phenyl,
(2) pyridyl,
(3) pyridazinyl,
(4) pyrimidyl,
(5) pyrazinyl,
(6) thiazolyl,
(7) thienyl,
(8) pyrrolyl,
(9) oxazolyl, and
(10) oxadiazole;
wherein R$^1$ is optionally mono or di-substituted with substituents R$^4$ and R$^5$, wherein R$^4$ and R5 are independently selected from the group consisting of:
(a) halo,
(b) —CN,
(c) mono, di or tri-halo C$_{1-4}$ alkyl,
(d) —O—C$_{1-4}$ alkyl, optionally substituted with hydroxyl, halo or amino
(e) —C$_{1-4}$alkyl optionally substituted with hydroxyl or CN,
(f) —C$_{1-2}$alkyl-C$_{3-6}$cycloalkyl optionally substituted with hydroxy,
(h) —S(O)$_n$C$_{1-4}$alkyl wherein n is 0, 1 or 2,
(i) —S(O)$_n$NR$^6$R$^7$,
(j) —C(O)—NR$^{10}$R$^{11}$,
(k) HET$^4$,
(l) aryl, and
wherein choices (k) and (l) are each optionally mono or di-substituted with substituents selected from
(1) halo,
(2) —CN,
(3) —OH,
(4) —C$_{1-4}$alkyl optionally substituted with hydroxy, halo or cyano,
(5) —CF$_3$,
(6) —OC$_{1-4}$alkyl optionally substituted with hydroxyl or halo,
(7) —C(O)OH,
(8) —C(O)O—C$_{1-3}$ alkyl, and
(9) —C(O)—NR$^{19}$R$^{20}$,
wherein R$^6$, R$^7$, R$^{10}$, R$^{11}$, R$^{19}$ and R$^{20}$ are each independently selected from H and C$_{1-4}$ alkyl.

3. The method of claim 2
wherein:
R$^1$ is selected from the group consisting of:
(1) phenyl,
(2) pyridyl,
(3) pyrimidyl,
(4) pyrazinyl,
(5) pyridazinyl,
(6) 1,2,4-oxadiazolyl, and
(7) 1,3,4-oxadiazolyl,
optionally mono or di-substituted with substituents R$^4$ and R$^5$, which are independently selected from the group consisting of (a) —$C_{1-4}$alkyl optionally substituted with hydroxy,
(b) —$S(O)_nC_{1-4}$alkyl,
(c) —$C(O)$—$NR^{10}R^{11}$,
(d) $HET^4$, and
(e) halo,
wherein $HET^4$ is optionally mono or di-substituted with substituents selected from:
(1) halo,
(2) —CN,
(3) —OH,
(4) —$C_{1-4}$alkyl optionally substituted with hydroxy, halo or cyano,
(5) —$CF_3$,
(6) —$OC_{1-4}$alkyl optionally substituted with hydroxyl or halo,
(7) —C(O)OH, and
(8) —C(O)O—$C_{1-3}$ alkyl, and
(9) —$C(O)$—$NR^{19}R^{20}$,
wherein $R^{10}$, $R^{11}$, $R^{19}$ and $R^{20}$ are each independently selected from H and $C_{1-4}$ alkyl.

4. The method of claim 1
wherein:
$R^2$ is selected from the group consisting of:
(1) aryl,
(2) $HET^3$,
(3) —$CH_2$aryl, and
(4) —$CH_2HET^3$,
wherein $R^2$ is optionally mono or di-substituted with substituents independently selected from the group consisting of:
(a) halo,
(b) —CN,
(c) —OH,
(d) —Hydroxy $C_{1-4}$alkyl,
(e) —$C_{1-4}$alkyl,
(f) —$C_{1-4}$haloalkyl, and
(g) —$OC_{1-4}$alkyl, optionally substituted with halo or hydroxyl.

5. The method of claim 4
wherein:
$R^2$ is selected from the group consisting of:
(1) aryl, and
(2) $HET^3$,
wherein $R^2$ is optionally mono or di-substituted with substituents independently selected from the group consisting of
(a) halo,
(b) —CN,
(c) —OH,
(d) -hydroxy $C_{1-4}$alkyl,
(e) —$CH_3$,
(f) —$CF_3$, and
(g) —$OCH_3$.

6. The method of claim 5
wherein:
$R^2$ is selected from the group consisting of:
(1) phenyl,
(2) pyridyl,
(3) pyridazinyl,
(4) pyrimidyl,
(5) pyrazinyl,
(6) thiazolyl,
(7) oxazolyl,
(8) pyrazolyl,
(9) 1,2,4-oxadiazolyl, and
(10) 1,3,4-oxadiazolyl,
wherein $R^2$ is optionally mono or di-substituted with halo, $OC_{1-4}$alkyl optionally substituted with halogen, —$C_{1-4}$ haloalkyl, hydroxyl and CN.

7. The method of claim 1,
wherein $R^3$ is $HET^5$, and wherein $HET^5$ is optionally mono or di-substituted with substituents independently selected from the group consisting of:
(a) halo,
(b) —$C_{3-6}$cycloalkyl,
(c) —$OC_{1-4}$ alkyl,
(d) mono, di or tri-halo $C_{1-4}$ alkyl, and
(e) mono, di or tri-halo —$OC_{1-4}$ alkyl.

8. The method of claim 7,
wherein $R^3$ is selected from the group consisting of:
(1) pyrimidinyl, and
(2) pyridyl,
wherein $R^3$ is optionally mono or di-substituted with halo, halo$C_{1-4}$alkyl, or —$OC_{1-4}$alkyl optionally substituted with halo.

9. The method of claim 1 wherein X is S.

10. The method of claim 1, comprising administering a compound of Formula Ia

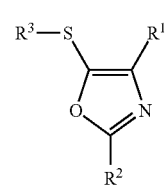

wherein
$R^1$ is selected from the group consisting of:
(1) phenyl,
(2) pyridyl,
(3) pyridazinyl,
(4) pyrimidyl,
(5) pyrazinyl,
(6) thiazolyl,
(7) thienyl,
(8) pyrrolyl,
(9) oxazolyl, and
(10) oxadiazole;
wherein $R^1$ is optionally mono or di-substituted with substituents $R^4$ and $R^5$, which are independently selected from the group consisting of
(a) halo,
(b) —CN,
(c) mono, di or tri-halo $C_{1-4}$ alkyl,
(d) —O—$C_{1-4}$alkyl, optionally substituted with hydroxyl, halo or amino
(e) —$C_{1-4}$alkyl optionally substituted with hydroxyl or CN,
(f) —$C_{1-2}$alkyl-$C_{3-6}$cycloalkyl optionally substituted with hydroxy,
(h) —$S(O)_nC_{1-4}$alkyl wherein n is 0, 1 or 2,
(i) —$S(O)_nNR^6R^7$,
(j) —$C(O)$—$NR^{10}R^{11}$,
(k) $HET^4$, and
(l) aryl,
wherein choices (k) and (l) are each optionally mono or di-substituted with substituents selected from
(1) halo,
(2) —CN,
(3) —OH, (4) —C$_{1-4}$alkyl optionally substituted with hydroxy, halo or cyano,
(5) —CF$_3$,
(6) —OC$_{1-4}$alkyl optionally substituted with hydroxyl or halo,
(7) —C(O)OH,
(8) —C(O)O—C$_{1-3}$ alkyl, and
(9) —C(O)—NR$^{19}$R$^{20}$,
wherein R$^6$, R$^7$, R$^{10}$, R$^{11}$, R$^{19}$ and R$^{20}$, are each independently selected from H and C$_{1-4}$ alkyl;
R$^2$ is selected from the group consisting of:
(1) aryl,
(2) HET$^3$, and
(3) —C$_{3-6}$cycloalkyl,
wherein choice R$^2$ is optionally mono or di-substituted with substituents independently selected from the group consisting of
(a) halo,
(b) —CN,
(c) —OH,
(d) -hydroxy C$_{1-4}$ alkyl,
(e) —C$_{1-4}$ alkyl,
(f) —C$_{1-4}$haloalkyl, and
(g) —OC$_{1-4}$alkyl, optionally substituted with halo or hydroxyl; and
R$^3$ is HET$^5$, wherein HET$^5$ is optionally mono or di-substituted with substituents independently selected from the group consisting of
(a) halo,
(b) —C$_{3-6}$cycloalkyl,
(c) —OC$_{1-4}$ alkyl,
(d) mono, di or tri-halo C$_{1-4}$ alkyl, and
(e) mono, di or tri-halo —OC$_{1-4}$ alkyl.

11. The method of claim 10 wherein
R$^1$ is selected from the group consisting of:
(1) phenyl,
(2) pyridyl,
(3) pyrimidyl,
(4) pyrazinyl,
(5) pyridazinyl,
(6) 1,2,4-oxadiazolyl, and
(7) 1,3,4-oxadiazolyl,
optionally mono or di-substituted with substituents R$^4$ and R$^5$, which are independently selected from the group consisting of
(a) —C$_{1-4}$alkyl optionally substituted with hydroxy,
(b) —S(O)$_n$C$_{1-4}$alkyl,
(c) —C(O)—NR$^{10}$R$^{11}$,
(d) HET$^4$, and
(e) halo,
wherein HET$^4$ is optionally mono or di-substituted with substituents selected from:
(1) halo,
(2) —CN,
(3) —OH,
(4) —C$_{1-4}$alkyl optionally substituted with hydroxy, halo or cyano,
(5) —CF$_3$,
(6) —OC$_{1-4}$alkyl optionally substituted with hydroxyl or halo,
(7) —C(O)OH, and
(8) —C(O)O—C$_{1-3}$ alkyl, and
(9) —C(O)—NR$^{19}$R$^{20}$,
wherein R$^{10}$, R$^{11}$, R$^{19}$ and R$^{20}$ are each independently selected from H and C$_{1-4}$alkyl, R$^2$ is selected from the group consisting of:
(1) phenyl,
(2) pyridyl,
(3) pyridazinyl,
(4) pyrimidyl,
(5) pyrazinyl,
(6) thiazolyl,
(7) oxazolyl,
(8) pyrazolyl,
(9) 1,2,4-oxadiazolyl, and
(10) 1,3,4-oxadiazolyl,
wherein R$^2$ is optionally mono or di-substituted with halo, OC$_{1-4}$alkyl optionally substituted with halogen, —C$_{1-4}$haloalkyl, hydroxyl and CN; and
R$^3$ is selected from the group consisting of:
(1) pyrimidyl, and
(2) pyridyl,
wherein R$^3$ is optionally mono or di-substituted with halo, haloC$_{1-4}$alkyl, or —OC$_{1-4}$alkyl optionally substituted with halo.

12. The method of claim 1, comprising administering a compound of Formula Ia

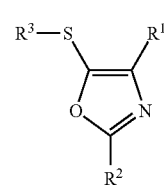

Ia wherein:
R$^1$ is selected from the group consisting of:
(1) phenyl,
(2) pyridyl,
(3) pyridazinyl,
(4) pyrimidyl,
(5) pyrazinyl,
wherein R$^1$ is optionally mono or di-substituted with substituents R$^4$ and R$^5$, which are independently selected from the group consisting of:
(a) halo,
(b) —CN,
(c) mono, di or tri-halo C$_{1-4}$ alkyl,
(d) —O—C$_{1-4}$alkyl, optionally substituted with hydroxyl, halo or amino
(e) —C(CH$_3$)$_2$—OH;
R$^2$ is selected from the group consisting of:
(1) phenyl,
(2) pyridyl,
(3) pyridazinyl,
(4) pyrimidyl,
(5) pyrazinyl,
(6) pyrazolyl,
wherein R$^2$ is optionally mono or di-substituted with halo, OC$_{1-4}$alkyl optionally substituted with halogen, —C$_{1-4}$haloalkyl, hydroxyl and CN; and
R$^3$ is selected from the group consisting of:
(1) pyrimidyl, and
(2) pyridyl,
wherein R$^3$ is optionally mono or di-substituted with halo, haloC$_{1-4}$alkyl, or —OC$_{1-4}$alkyl optionally substituted with halo.

13. The method of claim 12 wherein:
$R^1$ is selected from the group consisting of:
(1) phenyl,
(2) pyridyl,
(3) pyrazinyl,
wherein $R^1$ is optionally mono or di-substituted with substituents $R^4$ and $R^5$, which are independently selected from the group consisting of:
(a) halo,
(b) —CN,
(c) mono, di or tri-halo $C_{1-4}$ alkyl,
(d) —O—$C_{1-4}$alkyl, optionally substituted with hydroxyl, halo or amino
(e) —C(CH$_3$)$_2$—OH;
$R^2$ is selected from the group consisting of:
(1) phenyl,
(2) pyridyl,
wherein $R^2$ is optionally mono or di-substituted with halo, $OC_{1-4}$alkyl optionally substituted with halogen, —$C_{1-4}$ haloalkyl, hydroxyl and CN; and
$R^3$ is selected from the group consisting of:
(1) pyrimidyl, and
(2) pyridyl,
wherein $R^3$ is optionally mono or di-substituted with halo, halo$C_{1-4}$alkyl, or —$OC_{1-4}$alkyl optionally substituted with halo.

14. The method according to claim 1 wherein the compound is selected from the group consisting of:
(1) Methyl-5-[5-[(5-chloropyridin-2-yl)thio]-2-(4-fluorophenyl)-1,3-oxazol-4-yl]pyrazine-2-carboxylate,
(2) Methyl 5-[5-[(5-chloropyridin-2-yl)thio]-2-(3-fluorophenyl)-1,3-oxazol-4-yl]pyrazine-2-carboxylate,
(3) 2-{5-[5-[(5-Chloropyridin-2-yl)thio]-2-(4-fluorophenyl)-1,3-oxazol-4-yl]pyrazin-2-yl}propan-2-ol,
(4) 2-{5-[5-[(4-Chlorophenyl)thio]-2-(4-fluorophenyl)-1,3-oxazol-4-yl]pyrazin-2-yl}propan-2-ol,
(5) 2-(5-{2-(4-Fluorophenyl)-5-[(4-methoxyphenyl)thio]-1,3-oxazol-4-yl}pyrazin-2-yl)propan-2-ol,
(6) 2-{5-[5-[(4-Chlorophenyl)thio]-2-(3-fluorophenyl)-1,3-oxazol-4-yl]pyrazin-2-yl}propan-2-ol,
(7) 2-(5-{2-(3-Fluorophenyl)-5-[(4-methoxyphenyl)thio]-1,3-oxazol-4-yl}pyrazin-2-yl)propan-2-ol,
(8) 2-{5-[5-[(5-Chloropyridin-2-yl)thio]-2-(3-fluorophenyl)-1,3-oxazol-4-yl]pyrazin-2-yl}propan-2-ol,
(9) 2-[5-[(4-Chlorophenyl)thio]-2-(4-fluorophenyl)-1,3-oxazol-4-yl]-5-methylpyrazine,
(10) 2-{2-(3-Fluorophenyl)-5-[(4-methoxyphenyl)thio]-1,3-oxazol-4-yl}-5-methylpyrazine,
(11) 2-[5-[(4-Chlorophenyl)thio]-2-(3-fluorophenyl)-1,3-oxazol-4-yl]-5-methylpyrazine,
(12) 2-{5-[5-[(5-Chloropyridin-2-yl)thio]-2-(4-fluorophenyl)-1,3-oxazol-4-yl]pyrazin-2-yl}propan-2-ol,
(13) 2-{5-[5-[(4-Chlorophenyl)thio]-2-(4-fluorophenyl)-1,3-oxazol-4-yl]pyridin-2-yl}propan-2-ol,
(14) 2-(5-{2-(4-Fluorophenyl)-5-[(4-methoxyphenyl)thio]-1,3-oxazol-4-yl}pyridin-2-yl)propan-2-ol,
(15) 2-{5-[5-[(2,4-Difluorophenyl)thio]-2-(4-fluorophenyl)-1,3-oxazol-4-yl]pyridin-2-yl}propan-2-ol,
(16) 2-{5-[5-[(4-Chloro-2-fluorophenyl)thio]-2-(4-fluorophenyl)-1,3-oxazol-4-yl]pyridin-2-yl}propan-2-ol,
(17) 2-{5-[5-[(3,4-Difluorophenyl)thio]-2-(4-fluorophenyl)-1,3-oxazol-4-yl]pyridin-2-yl}propan-2-ol,
(18) 2-{5-[5-[(3-Fluoro-4-methoxyphenyl)thio]-2-(4-fluorophenyl)-1,3-oxazol-4-yl]pyridin-2-yl}propan-2-ol,
(19) 2-(5-{2-(4-Fluorophenyl)-5-[(5-fluoropyridin-2-yl)thio]-1,3-oxazol-4-yl}pyridin-2-yl)propan-2-ol,
(20) 2-{5-[5-[(5-Chloropyrimidin-2-yl)thio]-2-(4-fluorophenyl)-1,3-oxazol-4-yl]pyridin-2-yl}propan-2-ol,
(21) 2-(5-{2-(4-Fluorophenyl)-5-[(6-methoxypyridin-3-yl)thio]-1,3-oxazol-4-yl}pyridin-2-yl)propan-2-ol,
(22) 2-(5-{2-(4-Fluorophenyl)-5-[(5-fluoropyrimidin-2-yl)thio]-1,3-oxazol-4-yl}pyridin-2-yl)propan-2-ol,
(23) 2-(5-{2-(4-Fluorophenyl)-5-[(5-methoxypyrimidin-2-yl)thio]-1,3-oxazol-4-yl}pyridin-2-yl)propan-2-ol,
(24) 2-(5-{2-(4-Fluorophenyl)-5-[(2-methoxypyrimidin-5-yl)thio]-1,3-oxazol-4-yl}pyridin-2-yl)propan-2-ol,
(25) 2-(5-{2-(4-Fluorophenyl)-5-[(5-methylpyridin-2-yl)thio]-1,3-oxazol-4-yl}pyridin-2-yl)propan-2-ol,
(26) 2-{5-[5-[(5-Cyclopropylpyridin-2-yl)thio]-2-(4-fluorophenyl)-1,3-oxazol-4-yl]pyridin-2-yl}propan-2-ol,
(27) 2-(5-{2-(4-Fluorophenyl)-5-[(2,4,5-trifluorophenyl)thio]-1,3-oxazol-4-yl}pyridin-2-yl)propan-2-ol,
(28) 2-{5-[5-[(4-Chloro-3-fluorophenyl)thio]-2-(4-fluorophenyl)-1,3-oxazol-4-yl]pyridin-2-yl}propan-2-ol,
(29) 2-{5-[5-[(4-Chlorophenyl)thio]-2-(3-fluorophenyl)-1,3-oxazol-4-yl]pyridin-2-yl}propan-2-ol,
(30) 2-(5-{2-(3-Fluorophenyl)-5-[(4-methoxyphenyl)thio]-1,3-oxazol-4-yl}pyridin-2-yl)propan-2-ol,
(31) 2-{5-[5-[(5-Chloropyridin-2-yl)thio]-2-(3-fluorophenyl)-1,3-oxazol-4-yl]pyridin-2-yl}propan-2-ol,
(32) 2-{5-[5-[(5-Chloropyridin-2-yl)thio]-2-(3,5-difluorophenyl)-1,3-oxazol-4-yl]pyridin-2-yl}propan-2-ol,
(33) 2-(5-{2-(3,4-Difluorophenyl)-5-[(4-methoxyphenyl)thio]-1,3-oxazol-4-yl}pyridin-2-yl)propan-2-ol,
(34) 2-{5-[5-[(4-Chlorophenyl)thio]-2-(3,4-difluorophenyl)-1,3-oxazol-4-yl]pyridin-2-yl}propan-2-ol,
(35) 2-{5-[5-[(5-Chloropyridin-2-yl)thio]-2-(3,4-difluorophenyl)-1,3-oxazol-4-yl]pyridin-2-yl}propan-2-ol,
(36) 2-{5-[5-[(5-Chloropyrimidin-2-yl)thio]-2-(3,4-difluorophenyl)-1,3-oxazol-4-yl]pyridin-2-yl}propan-2-ol,
(37) 2-{5-[5-[(5-Chloropyridin-2-yl)thio]-2-(4-fluoro-2-methylphenyl)-1,3-oxazol-4-yl]pyridin-2-yl}propan-2-ol,
(38) 2-(5-{2-(4-Chlorophenyl)-5-[(5-chloropyridin-2-yl)thio]-1,3-oxazol-4-yl}pyridin-2-yl)propan-2-ol,
(39) 2-(5-{2-(4-Chlorophenyl)-5-[(5-fluoropyridin-2-yl)thio]-1,3-oxazol-4-yl}pyridin-2-yl)propan-2-ol,
(40) 2-(5-{2-(4-Chlorophenyl)-5-[(5-chloropyrimidin-2-yl)thio]-1,3-oxazol-4-yl}pyridin-2-yl)propan-2-ol,
(41) 2-(5-{2-(4-chloro-3-fluorophenyl)-5-[(4-chlorophenyl)thio]-1,3-oxazol-4-yl}pyridin-2-yl)propan-2-ol,
(42) 2-(5-{2-(4-chloro-3-fluorophenyl)-5-[(5-chloropyridin-2-yl)thio]-1,3-oxazol-4-yl}pyridin-2-yl)propan-2-ol,
(43) 2-(5-{2-(3-chloro-4-fluorophenyl)-5-[(4-chlorophenyl)thio]-1,3-oxazol-4-yl}pyridin-2-yl)propan-2-ol,
(44) 2-(5-{2-(3-chloro-4-fluorophenyl)-5-[(5-chloropyridin-2-yl)thio]-1,3-oxazol-4-yl}pyridin-2-yl)propan-2-ol,
(45) 2-{6-[5-[(5-Chloropyridin-2-yl)thio]-2-(4-fluorophenyl)-1,3-oxazol-4-yl]pyridin-3-yl}propan-2-ol,
(46) 2-{6-[5-[(4-chlorophenyl)thio]-2-(4-fluorophenyl)-1,3-oxazol-4-yl]pyridin-3-yl}propan-2-ol,
(47) 4-[5-[(4-Chlorophenyl)thio]-2-(4-fluorophenyl)-1,3-oxazol-4-yl]benzonitrile,
(48) 3-{4-[5-[(4-Chlorophenyl)thio]-2-(4-fluorophenyl)-1,3-oxazol-4-yl]phenyl}-1,2,4-oxadiazole,
(49) 4-{5-[(5-Chloropyridin-2-yl)thio]-4-[6-(1-hydroxy-1-methylethyl)pyridin-3-yl]-1,3-oxazol-2-yl}benzonitrile,
(50) 2-(5-{5-[(4-chlorophenyl)thio]-2-pyridin-2-yl-1,3-oxazol-4-yl}pyridin-2-yl)propan-2-ol,

(51) 2-(5-{5-[(5-chloropyridin-2-yl)thio]-2-pyridin-2-yl-1,3-oxazol-4-yl}pyridin-2-yl)propan-2-ol,
(52) 3-(4-{5-[(4-Chlorophenyl)thio]-2-phenyl-1,3oxazol-4-yl}phenyl)-1,2,4oxadiazole,
(53) 2-(4-{5-[(4-Chlorophenyl)thio]-2-phenyl-1,3oxazol-4-yl}phenyl)-1,3,4oxadiazole,
(54) 5-[(4-chlorophenyl)thio]-4-[4-(methylsulfonyl)phenyl]-2-phenyl-1,3-oxazole, and
(55) 2-{5-[(4-chlorophenyl)thio]-4-[4-(methylsulfonyl)phenyl]-1,3-oxazol-2-yl}pyridine, and
(56) 2-{5-[5-[(5-Chloropyridin-2-yl)thio]-2-(4-fluorophenyl)-1,3-oxazol-4-yl]pyridin-2-yl}propan-2-ol;
or a pharmaceutically acceptable salt thereof.

15. The method according to claim 1, wherein the compound is selected from the group consisting of (1) 5-Chloro-2-({2-(4-fluorophenyl)-4-[6-(1,2,4-oxadiazol-3-yl)pyridin-3-yl]-1,3-oxazol-5-yl}sulfanyl)pyridine,
(2) 5-{5-[(5-Chloropyridin-2-yl)sulfanyl]-2-(4-fluorophenyl)-1,3-oxazol-4-yl}pyrimidine-2-carbonitrile,
(3) 1-(5-{5-[(5-Chloropyridin-2-yl)sulfanyl]-2-(4-fluorophenyl)-1,3-oxazol-4-yl}pyrimidin-2-yl)ethanone,
(4) 2-(5-{5-[(5-Chloropyridin-2-yl)sulfanyl]-2-(4-fluorophenyl)-1,3-oxazol-4-yl}pyrimidin-2-yl)propan-2-ol,
(5) 5-Chloro-2-({2-(4-fluorophenyl)-4-[4-(methylsulfonyl)phenyl]-1,3-oxazol-5-yl}sulfanyl)pyridine,
(6) Methyl-4-{5-[(5-chloropyridin-2-yl)sulfanyl]-2-(4-fluorophenyl)-1,3-oxazol-4-yl}benzoate,
(7) 2-(4-{5-[(5-Chloropyridin-2-yl)sulfanyl]-2-(4-fluorophenyl)-1,3-oxazol-4-yl}phenyl)propan-2-ol,
(8) 4-{5-[(5-Chloropyridin-2-yl)sulfanyl]-2-(4-fluorophenyl)-1,3-oxazol-4-yl}-1-(methylsulfonyl)piperidinium trifluoroacetate,
(9) Methyl 2-(5-{5-[(5-chloropyridin-2-yl)sulfanyl]-2-(4-fluorophenyl)-1,3-oxazol-4-yl}pyridin-2-yl)-2-methylpropanoate,
(10) 3-(5-{5-[(5-chloropyridin-2-yl)sulfanyl]-2-(4-fluorophenyl)-1,3-oxazol-4-yl}pyridin-2-yl)-2,3-dimethylbutan-2-ol
(11) 2-(5-{5-[(5-chloropyridin-2-yl)sulfanyl]-2-(4-fluorophenyl)-1,3-oxazol-4-yl}pyridin-2-yl)-2-methylpropan-1-ol,
(12) Methyl 5-{5-[(5-chloropyridin-2-yl)sulfanyl]-2-cyclopropyl-1,3-oxazol-4-yl}pyridine-2-carboxylate,
(13) 1-(5-{5-[(5-Chloropyridin-2-yl)sulfanyl]-2-cyclopropyl-1,3-oxazol-4-yl}pyridin-2-yl)ethanone,
(14) 2-(5-{5-[(5-Chloropyridin-2-yl)sulfanyl]-2-cyclopropyl-1,3-oxazol-4-yl}pyridin-2-yl)propan-2-ol,
(15) 2-(6-{5-[(5-Chloropyridin-2-yl)sulfanyl]-2-(4-fluorophenyl)-1,3-oxazol-4-yl}pyridazin-3-yl)propan-2-ol,
(16) Ethyl 5-{5-[(5-chloropyridin-2-yl)sulfanyl]-2-(4-fluorophenyl)-1,3-oxazol-4-yl} isoxazole-3-carboxylate,
(17) 2-(5-{5-[(5-Chloropyridin-2-yl)sulfanyl]-2-(4-fluorophenyl)-1,3-oxazol-4-yl}isoxazol-3-yl)propan-2-ol,
(18) Methyl 2-{5-[(5-chloropyridin-2-yl)sulfanyl]-2-(4-fluorophenyl)-1,3-oxazol-4-yl}-1,3-thiazole-4-carboxylate,
(18) 2-(2-{5-[(5-Chloropyridin-2-yl)sulfanyl]-2-(4-fluorophenyl)-1,3-oxazol-4-yl}-1,3-thiazol-4-yl)propan-2-ol,
(19) 5-Chloro-2-({2-cyclopropyl-4-[6-(methylsulfonyl)pyridin-3-yl]-1,3-oxazol-5-yl}sulfanyl)pyridine,
(20) 5-Chloro-2-({2-(4-fluorophenyl)-4-[6-(methylsulfonyl)pyridin-3-yl]-1,3-oxazol-5-yl}sulfanyl)pyridine,
(21) 5-Chloro-2-({2-(4-fluorophenyl)-4-[6-(methylsulfonyl)pyridin-3-yl]-1,3-oxazol-5-yl}sulfanyl)pyrimidine,
(22) (R)-5-Chloro-2-({2-(4-fluorophenyl)-4-[6-(methylsulfinyl)pyridin-3-yl]-1,3-oxazol-5-yl}sulfanyl)pyridine,
(23) (S)-5-Chloro-2-({2-(4-fluorophenyl)-4-[6-(methylsulfinyl)pyridin-3-yl]-1,3-oxazol-5-yl}sulfanyl)pyridine,
(24) (R)-5-Fluoro-2-({2-(4-fluorophenyl)-4-[6-(methylsulfinyl)pyridin-3-yl]-1,3-oxazol-5-yl}sulfanyl)pyridine,
(25) (S)-5-Fluoro-2-({2-(4-fluorophenyl)-4-[6-(methylsulfinyl)pyridin-3-yl]-1,3-oxazol-5-yl}sulfanyl)pyridine,
(26) Methyl 5-(5-[(4-chlorophenyl)sulfanyl]-2-(1-ethyl-1H-pyrazol-4-yl)-1,3-oxazol-4-yl)pyridine-2-carboxylate,
(27) 2-(5-{5-[(4-chlorophenyl)sulfanyl]-2-(1-ethyl-1H-pyrazol-4-yl)-1,3-oxazol-4-yl)pyridin-2-yl}propan-2-ol,
(28) Methyl 5-{5-[(5-chloropyridin-2-yl)sulfanyl]-2-(1-ethyl-1H-pyrazol-4-yl}-1,3-oxazol-4-yl)pyridine-2-carboxylate,
(29) 2-(5-{5-[(5-chloropyridin-2-yl)sulfanyl]-2-(1-ethyl-1H-pyrazol-4-yl)-1,3-oxazol-4-yl}pyridin-2-yl}propan-2-ol,
(30) 5-Chloro-2-({2-(4-fluorophenyl)-4-[6-(methylsulfanyl)pyridin-3-yl]-1,3-oxazol-5-yl}sulfanyl)pyridine,
(31) Methyl 5-{5-[(5-chloropyridin-2-yl)sulfanyl]-2-cyclobutyl-1,3-oxazol-4-yl}pyridine-2-carboxylate,
(32) 2-(5-{5-[(5-Chloropyridin-2-yl)sulfanyl]-2-cyclobutyl-1,3-oxazol-4-yl}pyridin-2-yl)propan-2-ol,
(33) 1-(5-{5-[(5-Chloropyridin-2-yl)sulfanyl]-2-cyclobutyl-1,3-oxazol-4-yl}pyridin-2-yl)ethanone,
(34) (R)-1-(5-{5-[(5-Chloropyridin-2-yl)sulfanyl]-2-cyclobutyl-1,3-oxazol-4-yl}pyridin-2-yl)ethanol,
(35) (S)-1-(5-{5-[(5-Chloropyridin-2-yl)sulfanyl]-2-cyclobutyl-1,3-oxazol-4-yl}pyridin-2-yl)ethanol,
(36) Methyl 5-{2-(5-chloropyridin-3-yl)-5-[(5-chloropyridin-2-yl)sulfanyl]-1,3-oxazol-4-yl}pyridine-2-carboxylate,
(37) 2-(5-{2-(5-Chloropyridin-3-yl)-5-[(5-chloropyridin-2-yl)sulfanyl]-1,3-oxazol-4-yl}pyridin-2-yl)propan-2-ol,
(38) 1-(5-{2-(5-Chloropyridin-3-yl)-5-[(5-chloropyridin-2-yl)sulfanyl]-1,3-oxazol-4-yl}pyridin-2-yl)ethanone,
(39) (5-{5-[(5-Chloropyridin-2-yl)sulfanyl]-2-(4-fluorophenyl)-1,3-oxazol-4-yl}pyridin-2-yl)acetonitrile,
(40) 1-(5-{5-[(5-Chloropyridin-2-yl)sulfanyl]-2-(4-fluorophenyl)-1,3-oxazol-4-yl}pyridin-2-yl)-3-hydroxycyclobutanecarbonitrile,
(41) 2-(5-{5-[(5-Chloropyridin-2-yl)sulfanyl]-2-(4-fluorobenzyl)-1,3-oxazol-4-yl}pyridin-2-yl)propan-2-ol,
(42) Methyl 2-{5-[(5-chloropyridin-2-yl)sulfanyl]-2-(4-fluorophenyl)-1,3-oxazol-4-yl}pyrimidine-5-carboxylate,
(43) 6-{5-[(4-Chlorophenyl)sulfanyl]-2-(4-fluorophenyl)-1,3-oxazol-4-yl}-3,4-dihydroisoquinolin-1(2H)-one,
(44) 7-{5-[(4-Chlorophenyl)sulfanyl]-2-(4-fluorophenyl)-1,3-oxazol-4-yl}-3-(difluoromethyl)quinoline,
(45) 6-{5-[(4-Chlorophenyl)sulfanyl]-2-(4-fluorophenyl)-1,3-oxazol-4-yl}-2-(difluoromethyl)quinoline,
(46) 6-{5-[(5-Chloropyridin-2-yl)sulfanyl]-2-(4-fluorophenyl)-1,3-oxazol-4-yl}-N,N-dimethylquinoline-2-carboxamide,

(47) 3-{5-[(5-Chloropyridin-2-yl)sulfanyl]-2-(4-fluorophenyl)-1,3-oxazol-4-yl}-6-(methylsulfonyl)pyridazine, and

(48) (1S,2S)-2-(4-{5-[(5-chloropyridin-2-yl)thio]-2-cyclopropyl-1,3-oxazol-4-yl}phenyl)-N,N-dimethylcyclopropanecarboxamide, and

(49) 2-{5-[5-[(5-Chloropyridin-2-yl)thio]-2-(4-fluorophenyl)-1,3-oxazol-4-yl]pyridin-2-yl}propan-2-ol, or a pharmaceutically acceptable salt thereof.

16. The method of claim 1, wherein the compound is selected from a compound having the formula

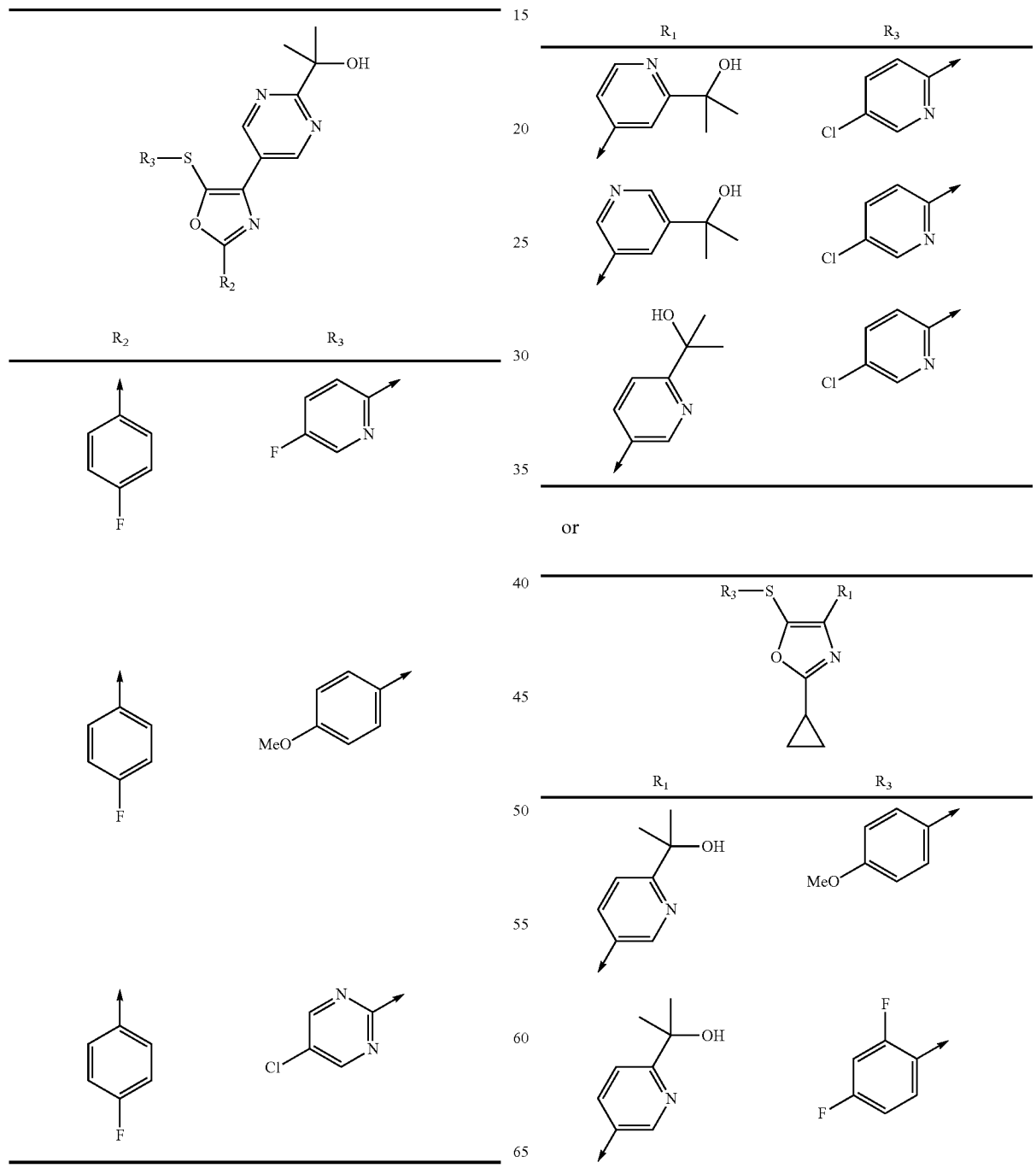

-continued

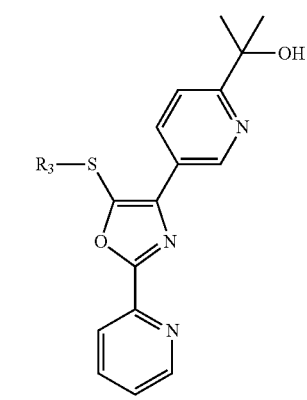
R₃
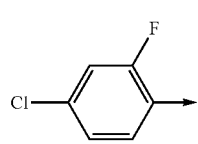
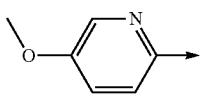
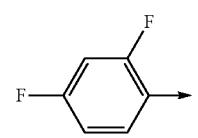
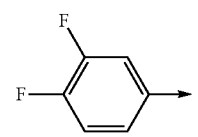
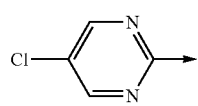
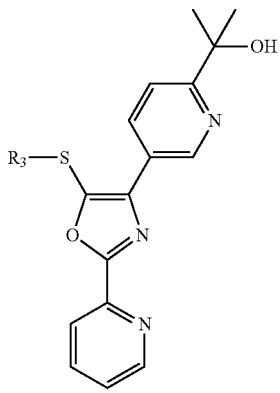
R₃
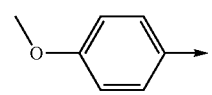
or a pharmaceutically acceptable salt thereof.
17. The method of claim 1 wherein the compound is
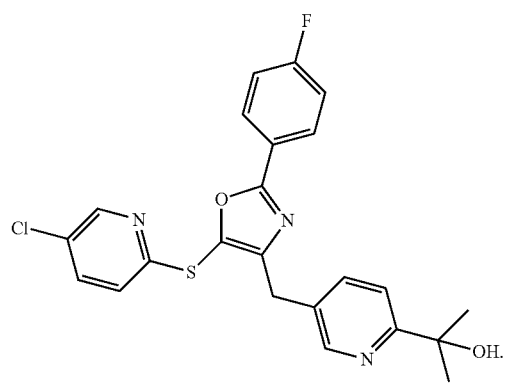 [SMILES: CC(C)(O)c1ccc(Cc2nc(-c3ccc(F)cc3)oc2Sc2ccc(Cl)cn2)cn1]
or a pharmaceutically acceptable salt thereof.
18. The method of claim 1, wherein the pain is skeletomuscular pain or acute pain.
19. The method of claim 1, wherein the warm-blooded animal is a dog.
* * * * *

SEQUENCE LISTING

```
<160> NUMBER OF SEQ ID NOS: 3

<210> SEQ ID NO 1
<211> LENGTH: 36
<212> TYPE: DNA
<213> ORGANISM: Unknown
<220> FEATURE:
<223> OTHER INFORMATION: Primer

<400> SEQUENCE: 1
caaggtaccg ccaccatggt gctgagcgaa gtgtgg                                   36

<210> SEQ ID NO 2
<211> LENGTH: 30
<212> TYPE: DNA
<213> ORGANISM: Unknown
<220> FEATURE:
<223> OTHER INFORMATION: Primer

<400> SEQUENCE: 2
ccggaattct caagatggcc gcttttcagg                                          30

<210> SEQ ID NO 3
<211> LENGTH: 30
<212> TYPE: DNA
<213> ORGANISM: Unknown
<220> FEATURE:
<223> OTHER INFORMATION: Primer

<400> SEQUENCE: 3
ccggaattct cacgatggct gcttttgagg                                          30
```